US012310804B2

(12) United States Patent
Eyre et al.

(10) Patent No.: US 12,310,804 B2
(45) Date of Patent: *May 27, 2025

(54) SURGICAL PLATFORM WITH ADJUSTABLE ARM SUPPORTS

(71) Applicant: Auris Health, Inc., Redwood City, CA (US)

(72) Inventors: Nicholas J. Eyre, Sunnyvale, CA (US); Colin Allen Wilson, Burlingame, CA (US); Andrew F. O'Rourke, Los Angeles, CA (US); Travis C. Covington, Campbell, CA (US); Sven Wehrmann, Redwood City, CA (US)

(73) Assignee: Auris Health Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/359,710

(22) Filed: Jul. 26, 2023

(65) Prior Publication Data

US 2023/0372056 A1    Nov. 23, 2023

Related U.S. Application Data

(63) Continuation of application No. 16/730,543, filed on Dec. 30, 2019, now Pat. No. 11,744,670, which is a
(Continued)

(51) Int. Cl.
*A61B 17/00* (2006.01)
*A61B 1/00* (2006.01)
(Continued)

(52) U.S. Cl.
CPC .......... *A61B 90/50* (2016.02); *A61B 1/00149* (2013.01); *A61B 34/30* (2016.02);
(Continued)

(58) Field of Classification Search
CPC ............. A61B 34/30; A61B 2034/301; A61B 2034/302; A61B 2034/304;
(Continued)

(56) References Cited

U.S. PATENT DOCUMENTS 3,997,926 A   12/1976  England
4,878,494 A   11/1989  Phillips et al.
(Continued)

FOREIGN PATENT DOCUMENTS

CN    202314134 U    7/2012
CN    104783900 A    7/2015
(Continued)

OTHER PUBLICATIONS

International search report and written opinion dated Mar. 4, 2019 for PCT/US2018/067984.
(Continued)

*Primary Examiner* — Tuan V Nguyen
(74) *Attorney, Agent, or Firm* — Frost Brown Todd LLP

(57) ABSTRACT

A robotic surgical system can include one or more adjustable arm supports that support one or more robotic arms. The adjustable arm supports can be configured to attach to either a table, a column support of the table, or a base of the table to deploy the adjustable arm supports and robotic arms from a position below the table. In some examples, the adjustable arm supports include at least four degrees of freedom that allow for adjustment of the position of a bar or rail to which the robotic arms are mounted. One of the degrees of freedom can allow the adjustable arm support to be adjusted vertically relative to the table.

20 Claims, 42 Drawing Sheets

Related U.S. Application Data continuation of application No. 16/234,975, filed on Dec. 28, 2018, now Pat. No. 10,517,692.

(60) Provisional application No. 62/618,489, filed on Jan. 17, 2018.

(51) Int. Cl.
  *A61B 17/04* (2006.01)
  *A61B 34/30* (2016.01)
  *A61B 90/50* (2016.01)
  *A61B 34/37* (2016.01)
  *A61B 90/00* (2016.01)
  *A61B 90/57* (2016.01)

(52) U.S. Cl.
  CPC ... *A61B 2034/301* (2016.02); *A61B 2034/302* (2016.02); *A61B 2034/304* (2016.02); *A61B 2034/305* (2016.02); *A61B 34/37* (2016.02); *A61B 2090/064* (2016.02); *A61B 2090/066* (2016.02); *A61B 90/37* (2016.02); *A61B 2090/376* (2016.02); *A61B 2090/571* (2016.02)

(58) Field of Classification Search
  CPC .............. A61B 2034/305; A61B 90/50; A61B 2090/571; A61B 1/00149
  See application file for complete search history.

(56) References Cited

U.S. PATENT DOCUMENTS

| | | |
|---|---|---|
| 5,013,018 A | 5/1991 | Sicek |
| 5,160,106 A | 11/1992 | Monick |
| 5,199,417 A | 4/1993 | Muller et al. |
| 5,259,365 A | 11/1993 | Nishikori |
| 5,405,604 A | 4/1995 | Has et al. |
| 5,555,897 A | 9/1996 | Lathrop, Jr. et al. |
| 5,571,072 A | 11/1996 | Kronner |
| 5,597,146 A | 1/1997 | Putman |
| 5,762,458 A | 6/1998 | Wang et al. |
| 5,814,038 A | 9/1998 | Jensen et al. |
| 5,855,583 A | 1/1999 | Wang |
| 5,876,325 A | 3/1999 | Mizuno et al. |
| 5,926,875 A | 7/1999 | Okamoto et al. |
| 5,944,476 A | 8/1999 | Bacchi et al. |
| 6,170,102 B1 | 1/2001 | Kreuzer |
| 6,202,230 B1 | 3/2001 | Borders |
| 6,351,678 B1 | 2/2002 | Borders |
| 6,620,174 B2 | 9/2003 | Jensen et al. |
| 6,640,363 B1 | 11/2003 | Pattee et al. |
| 6,676,669 B2 | 1/2004 | Charles et al. |
| 6,788,018 B1 | 9/2004 | Blumenkranz |
| 6,804,581 B2 | 10/2004 | Wang |
| 7,025,761 B2 | 4/2006 | Wang et al. |
| 7,027,892 B2 | 4/2006 | Wang |
| 7,074,179 B2 | 7/2006 | Wang et al. |
| 7,607,440 B2 | 10/2009 | Coste-Maniere et al. |
| 7,695,481 B2 | 4/2010 | Wang et al. |
| 7,763,015 B2 | 7/2010 | Cooper et al. |
| 7,789,874 B2 | 9/2010 | Yu et al. |
| 7,850,642 B2 | 12/2010 | Moll et al. |
| 7,963,288 B2 | 6/2011 | Rosenberg et al. |
| 8,005,537 B2 | 6/2011 | Hlavka et al. |
| 7,972,298 B2 | 7/2011 | Wallace et al. |
| 7,974,681 B2 | 7/2011 | Wallace et al. |
| 7,976,539 B2 | 7/2011 | Hlavka et al. |
| 7,979,157 B2 | 7/2011 | Anvari |
| 7,996,110 B2 | 8/2011 | Lipow et al. |
| 8,021,326 B2 | 9/2011 | Moll et al. |
| 8,052,636 B2 | 11/2011 | Moll et al. |
| 8,108,069 B2 | 1/2012 | Stahler et al. |
| 8,142,420 B2 | 3/2012 | Schena |
| 8,146,874 B2 | 4/2012 | Yu |
| 8,172,747 B2 | 5/2012 | Wallace et al. |
| 8,190,238 B2 | 5/2012 | Moll et al. |
| 8,230,863 B2 | 7/2012 | Ravikumar et al. |
| 8,257,303 B2 | 9/2012 | Moll et al. |
| 8,311,626 B2 | 11/2012 | Hlavka et al. |
| 8,343,096 B2 | 1/2013 | Kirschenman et al. |
| 8,348,931 B2 | 1/2013 | Cooper et al. |
| 8,394,054 B2 | 3/2013 | Wallace et al. |
| 8,400,094 B2 | 3/2013 | Schena |
| 8,409,136 B2 | 4/2013 | Wallace et al. |
| 8,409,172 B2 | 4/2013 | Moll et al. |
| 8,414,598 B2 | 4/2013 | Brock et al. |
| 8,425,404 B2 | 4/2013 | Wilson et al. |
| 8,469,945 B2 | 6/2013 | Schena |
| 8,498,691 B2 | 7/2013 | Moll et al. |
| 8,506,556 B2 | 8/2013 | Schena |
| 8,512,353 B2 | 8/2013 | Rosielle et al. |
| 8,515,576 B2 | 8/2013 | Lipow et al. |
| 8,617,102 B2 | 12/2013 | Moll et al. |
| 8,641,698 B2 | 2/2014 | Sanchez et al. |
| 8,652,030 B2 | 2/2014 | Matsuura et al. |
| 8,801,661 B2 | 8/2014 | Moll et al. |
| 8,897,920 B2 | 11/2014 | Wang et al. |
| 8,911,429 B2 | 12/2014 | Olds et al. |
| 8,926,603 B2 | 1/2015 | Hlavka et al. |
| 8,960,622 B2 | 2/2015 | von Pechmann et al. |
| 8,968,333 B2 | 3/2015 | Yu et al. |
| 8,974,408 B2 | 3/2015 | Wallace et al. |
| 9,023,060 B2 | 5/2015 | Cooper et al. |
| 9,078,686 B2 | 7/2015 | Schena |
| 9,119,653 B2 | 9/2015 | Amat Girbau |
| 9,119,655 B2 | 9/2015 | Bowling |
| 9,259,281 B2 | 2/2016 | Griffiths et al. |
| 9,314,306 B2 | 4/2016 | Yu |
| 9,326,822 B2 | 5/2016 | Lewis et al. |
| 9,358,076 B2 | 6/2016 | Moll et al. |
| 9,408,669 B2 | 8/2016 | Kokish et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,554,865 B2 | 1/2017 | Olds et al. |
| 9,561,083 B2 | 2/2017 | Yu et al. |
| 9,566,201 B2 | 2/2017 | Yu |
| 9,579,088 B2 | 2/2017 | Farritor |
| 9,615,889 B2 | 4/2017 | Jensen |
| 9,622,827 B2 | 4/2017 | Yu et al. |
| 9,629,682 B2 | 4/2017 | Wallace et al. |
| 9,636,184 B2 | 5/2017 | Lee et al. |
| 9,668,768 B2 | 6/2017 | Piron et al. |
| 9,713,499 B2 | 7/2017 | Bar et al. |
| 9,713,509 B2 | 7/2017 | Schuh et al. |
| 9,717,563 B2 | 8/2017 | Tognaccini |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,795,454 B2 | 10/2017 | Seeber et al. |
| 9,820,819 B2 | 11/2017 | Olson |
| 9,844,412 B2 | 12/2017 | Bogusky et al. |
| 9,850,924 B2 | 12/2017 | Vogtherr et al. |
| 9,867,635 B2 | 1/2018 | Alvarez et al. |
| 9,907,458 B2 | 3/2018 | Schena |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 9,999,476 B2 | 6/2018 | Griffiths |
| 10,016,900 B1 | 7/2018 | Meyer et al. |
| 10,022,192 B1 | 7/2018 | Ummalaneni |
| 10,080,576 B2 | 9/2018 | Romo et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni et al. |

(56) References Cited

U.S. PATENT DOCUMENTS

| | | |
|---|---|---|
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,350,390 B2 | 7/2019 | Moll et al. |
| 10,368,951 B2 | 8/2019 | Moll et al. |
| 10,376,672 B2 | 8/2019 | Yu |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,454,347 B2 | 10/2019 | Covington et al. |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,539,478 B2 | 1/2020 | Lin |
| 10,543,047 B2 | 1/2020 | Yu |
| 10,543,048 B2 | 1/2020 | Noonan et al. |
| 10,555,778 B2 | 2/2020 | Ummalaneni et al. |
| 10,556,092 B2 | 2/2020 | Yu et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,871 B2 | 6/2020 | Romo et al. |
| 10,667,875 B2 | 6/2020 | DeFonzo |
| 10,682,189 B2 | 6/2020 | Schuh et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,765,487 B2 | 9/2020 | Ho |
| 10,814,101 B2 | 10/2020 | Jiang |
| 10,820,947 B2 | 11/2020 | Julian |
| 10,820,954 B2 | 11/2020 | Marsot et al. |
| 10,828,118 B2 | 11/2020 | Schuh et al. |
| 10,881,280 B2 | 1/2021 | Baez |
| 2002/0082612 A1 | 6/2002 | Moll et al. |
| 2002/0162926 A1 | 11/2002 | Nguyen |
| 2002/0165524 A1 | 11/2002 | Sanchez et al. |
| 2002/0170116 A1 | 11/2002 | Borders |
| 2003/0181809 A1 | 9/2003 | Hall et al. |
| 2003/0191455 A1 | 10/2003 | Sanchez et al. |
| 2004/0243147 A1 | 12/2004 | Lipow |
| 2004/0261179 A1 | 12/2004 | Blumenkranz |
| 2005/0222554 A1 | 10/2005 | Wallace et al. |
| 2006/0069383 A1 | 3/2006 | Bogaerts |
| 2006/0149418 A1 | 7/2006 | Anvari |
| 2006/0161136 A1 | 7/2006 | Anderson |
| 2006/0178556 A1 | 8/2006 | Hasser et al. |
| 2006/0200026 A1 | 9/2006 | Wallace et al. |
| 2007/0137371 A1 | 6/2007 | Devengenzo |
| 2007/0293734 A1 | 12/2007 | Coste-Maniere |
| 2008/0027464 A1 | 1/2008 | Moll et al. |
| 2008/0039867 A1 | 2/2008 | Feussner |
| 2008/0082109 A1 | 4/2008 | Moll et al. |
| 2008/0147089 A1 | 6/2008 | Loh |
| 2008/0167750 A1 | 7/2008 | Stahler |
| 2008/0195081 A1 | 8/2008 | Moll et al. |
| 2008/0218770 A1 | 9/2008 | Moll et al. |
| 2008/0245946 A1 | 10/2008 | Yu |
| 2009/0005768 A1 | 1/2009 | Sharareh |
| 2009/0036900 A1 | 2/2009 | Moll |
| 2009/0041565 A1 | 2/2009 | Rodriguez Y Baena |
| 2009/0048611 A1 | 2/2009 | Funda |
| 2009/0062602 A1 | 3/2009 | Rosenberg et al. |
| 2009/0163928 A1 | 6/2009 | Schena |
| 2009/0326318 A1 | 12/2009 | Tognaccini |
| 2010/0100045 A1 | 4/2010 | Pravongviengkham et al. |
| 2010/0185211 A1 | 7/2010 | Herman |
| 2010/0204713 A1 | 8/2010 | Ruiz |
| 2010/0234857 A1 | 9/2010 | Itkowitz |
| 2010/0286712 A1 | 11/2010 | Won et al. |
| 2011/0028894 A1 | 2/2011 | Foley et al. |
| 2011/0238083 A1 | 9/2011 | Moll et al. |
| 2011/0257786 A1 | 10/2011 | Caron |
| 2011/0270273 A1 | 11/2011 | Moll et al. |
| 2011/0277775 A1 | 11/2011 | Holop et al. |
| 2011/0282359 A1 | 11/2011 | Duval |
| 2012/0136372 A1 | 5/2012 | Amat Girbau et al. |
| 2012/0191079 A1 | 7/2012 | Moll et al. |
| 2012/0191083 A1 | 7/2012 | Moll et al. |
| 2012/0191086 A1 | 7/2012 | Moll et al. |
| 2012/0241576 A1 | 9/2012 | Yu |
| 2012/0253332 A1 | 10/2012 | Moll |
| 2012/0266379 A1 | 10/2012 | Hushek |
| 2012/0277764 A1 | 11/2012 | Cooper |
| 2012/0283747 A1 | 11/2012 | Popovic |
| 2012/0296161 A1 | 11/2012 | Wallace et al. |
| 2012/0302869 A1 | 11/2012 | Koyrakh |
| 2013/0041219 A1* | 2/2013 | Hasegawa ............. A61B 34/76 600/109 |
| 2013/0053866 A1 | 2/2013 | Leung et al. |
| 2013/0096576 A1 | 5/2013 | Cooper |
| 2013/0131695 A1 | 5/2013 | Scarfogliero et al. |
| 2013/0190741 A1 | 7/2013 | Moll et al. |
| 2013/0204091 A1 | 8/2013 | Menendez et al. |
| 2013/0255425 A1 | 10/2013 | Schena |
| 2013/0310639 A1 | 11/2013 | Omori |
| 2013/0317519 A1 | 11/2013 | Romo et al. |
| 2013/0338679 A1 | 12/2013 | Rosielle et al. |
| 2014/0018960 A1 | 1/2014 | Itkowitz |
| 2014/0051049 A1 | 2/2014 | Jarc |
| 2014/0051987 A1 | 2/2014 | Kowshik |
| 2014/0142591 A1 | 5/2014 | Alvarez et al. |
| 2014/0180309 A1 | 6/2014 | Seeber et al. |
| 2014/0188132 A1 | 7/2014 | Kang |
| 2014/0243801 A1 | 8/2014 | Fanelli et al. |
| 2014/0249546 A1 | 9/2014 | Shvartsberg et al. |
| 2014/0276594 A1 | 9/2014 | Tanner et al. |
| 2014/0276647 A1 | 9/2014 | Yu |
| 2014/0276935 A1 | 9/2014 | Yu |
| 2014/0277333 A1 | 9/2014 | Lewis et al. |
| 2014/0277334 A1 | 9/2014 | Yu et al. |
| 2014/0316436 A1 | 10/2014 | Bar et al. |
| 2014/0357984 A1 | 12/2014 | Wallace et al. |
| 2014/0364870 A1 | 12/2014 | Alvarez et al. |
| 2015/0025549 A1 | 1/2015 | Kilroy et al. |
| 2015/0038981 A1 | 2/2015 | Kilroy et al. |
| 2015/0045675 A1 | 2/2015 | Chernomorsky |
| 2015/0119637 A1 | 4/2015 | Alvarez |
| 2015/0142013 A1 | 5/2015 | Tanner et al. |
| 2015/0239082 A1 | 8/2015 | Krouglicof |
| 2015/0297299 A1 | 10/2015 | Yeung |
| 2015/0305650 A1 | 10/2015 | Hunter |
| 2015/0335389 A1 | 11/2015 | Greenberg |
| 2016/0001038 A1 | 1/2016 | Romo et al. |
| 2016/0100896 A1 | 4/2016 | Yu |
| 2016/0157942 A1 | 6/2016 | Gombert |
| 2016/0220324 A1 | 8/2016 | Tesar |
| 2016/0270865 A1 | 9/2016 | Landey et al. |
| 2016/0287279 A1 | 10/2016 | Bovay et al. |
| 2016/0296294 A1 | 10/2016 | Moll et al. |
| 2016/0302871 A1 | 10/2016 | Gregerson |
| 2016/0331477 A1* | 11/2016 | Yu ..................... A61B 1/00149 |
| 2016/0338783 A1 | 11/2016 | Romo et al. |
| 2016/0338785 A1 | 11/2016 | Kokish et al. |
| 2016/0346052 A1 | 12/2016 | Rosielle et al. |
| 2016/0374590 A1 | 12/2016 | Wong et al. |
| 2016/0374771 A1 | 12/2016 | Mirbagheri |
| 2017/0007337 A1 | 1/2017 | Dan |

(56) References Cited

U.S. PATENT DOCUMENTS

| | | |
|---|---|---|
| 2017/0007343 A1 | 1/2017 | Yu |
| 2017/0045807 A1 | 2/2017 | Ye |
| 2017/0071456 A1 | 3/2017 | Ratnakar |
| 2017/0071692 A1 | 3/2017 | Taylor et al. |
| 2017/0071693 A1 | 3/2017 | Taylor et al. |
| 2017/0119481 A1 | 5/2017 | Romo et al. |
| 2017/0135710 A1 | 5/2017 | Hasegawa et al. |
| 2017/0135771 A1 | 5/2017 | Auld et al. |
| 2017/0143442 A1 | 5/2017 | Tesar |
| 2017/0165011 A1 | 6/2017 | Bovay et al. |
| 2017/0172673 A1 | 6/2017 | Yu et al. |
| 2017/0189118 A1 | 7/2017 | Chopra |
| 2017/0189131 A1 | 7/2017 | Weir |
| 2017/0202627 A1 | 7/2017 | Sramek et al. |
| 2017/0209073 A1 | 7/2017 | Sramek et al. |
| 2017/0209217 A1 | 7/2017 | Jensen |
| 2017/0215976 A1 | 8/2017 | Nowlin et al. |
| 2017/0215978 A1 | 8/2017 | Wallace et al. |
| 2017/0290631 A1 | 10/2017 | Lee et al. |
| 2017/0304021 A1 | 10/2017 | Hathaway |
| 2017/0325906 A1 | 11/2017 | Piecuch et al. |
| 2017/0340353 A1 | 11/2017 | Ahluwalia et al. |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0065252 A1 | 3/2018 | Tabandeh |
| 2018/0078439 A1 | 3/2018 | Cagle et al. |
| 2018/0078440 A1 | 3/2018 | Koenig et al. |
| 2018/0079090 A1 | 3/2018 | Koenig et al. |
| 2018/0098817 A1 | 4/2018 | Nichogi et al. |
| 2018/0116758 A1 | 5/2018 | Schlosser |
| 2018/0177470 A1 | 6/2018 | Suga |
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0289445 A1 | 10/2018 | Krinninger |
| 2018/0296285 A1 | 10/2018 | Simi et al. |
| 2018/0325499 A1 | 11/2018 | Landey et al. |
| 2018/0333044 A1 | 11/2018 | Jenkins |
| 2018/0338799 A1 | 11/2018 | Hladio et al. |
| 2018/0360435 A1 | 12/2018 | Romo |
| 2018/0368920 A1 | 12/2018 | Ummalaneni |
| 2018/0369035 A1 | 12/2018 | Bhimavarapu |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0255359 A1 | 8/2019 | Benali |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0375678 A1 | 12/2020 | Wallace |
| 2020/0405317 A1 | 12/2020 | Wallace |
| 2020/0405411 A1 | 12/2020 | Draper et al. |
| 2020/0405419 A1 | 12/2020 | Mao |
| 2020/0405420 A1 | 12/2020 | Purohit |
| 2020/0405423 A1 | 12/2020 | Schuh |
| 2020/0405424 A1 | 12/2020 | Schuh |
| 2020/0405434 A1 | 12/2020 | Schuh |
| 2020/0406002 A1 | 12/2020 | Romo |
| 2021/0007819 A1 | 1/2021 | Schuh |
| 2021/0008341 A1 | 1/2021 | Landey et al. |

FOREIGN PATENT DOCUMENTS

| | | |
|---|---|---|
| CN | 106456259 A | 2/2017 |
| GB | 810956 | 3/1959 |
| JP | 2012-005557 | 1/2012 |
| KR | 101448201 | 10/2014 |
| WO | WO 10/068005 | 6/2010 |

(56) References Cited

FOREIGN PATENT DOCUMENTS

WO  WO 11/005335   1/2011
WO  WO 15/010788   1/2015

OTHER PUBLICATIONS

Extended European Search Report from European Patent Application No. 18901740.3, dated Sep. 30, 2021, 8 pages.
International search report and written opinion dated Jul. 13, 2016 for PCT/US2016/026783.
Darwone, 2015, Operative technique and early experience for robotic assisted laparoscopic nephroureterectomy (RALNU) using da Vinci XI, SpringerPlus, 4:298.
Sasaki, 2017, Laparoscopic hernicolectomy for a patient with situs inversus lotalis: a case report, Int. J. Surg. Case Rep. 41:93-96.
International Search Report and Written Opinion, Application No. PCT/US16/32505, Sep. 23, 2016, 10 pages.
Invitation to Pay Additional Fees, Application No. PCT/US16/32505, Jul. 19, 2016, 2 pages.
Office Action, U.S. Appl. No. 15/154,762, Oct. 18, 2016, 7 pages.
U.S. Appl. No. 16/730,543, filed Dec. 30, 2019.
U.S. Appl. No. 16/234,975, filed Dec. 28, 2018.

\* cited by examiner

SURGICAL PLATFORM WITH ADJUSTABLE ARM SUPPORTS

CROSS-REFERENCE TO RELATED APPLICATIONS

This present application is a continuation of U.S. patent application Ser. No. 16/730,543 filed Dec. 30, 2019, now U.S. Pat. No. 11,744,670, which is a continuation of U.S. patent application Ser. No. 16/234,975 filed Dec. 28, 2018, now U.S. Pat. No. 10,517,692, which claims priority to U.S. Provisional Patent Application No. 62/618,489 filed Jan. 17, 2018, all of which are incorporated herein by reference in their entirety for all purposes.

BACKGROUND

Field

This description generally relates to medical systems, and particularly to a surgical or medical platform, table, or bed with adjustable arm supports.

Description

Robotic technologies have a range of applications. In particular, robotic arms help complete tasks that a human would normally perform. For example, factories use robotic arms to manufacture automobiles and consumer electronics products. Additionally, scientific facilities use robotic arms to automate laboratory procedures such as transporting microplates. Recently, physicians have started using robotic arms to help perform surgical procedures. For instance, physicians use robotic arms to control surgical instruments inside a patient. However, existing medical systems including robotic arms have a high capital cost and are typically specialized to perform limited types of surgical procedures. Thus, physicians or their assistants may need to obtain multiple robotic arm systems to accommodate a range of surgical procedures. Manually reconfiguring a robotic arm system for each surgical procedure is also time-consuming and physically demanding for the physicians.

SUMMARY

A surgical (or medical) robotics system with robotic arms is configurable to perform a variety of surgical (or medical) procedures. A robotic surgical system can include one or more adjustable arm supports that support one or more robotic arms. The adjustable arm supports can be configured to attach to either a table, a column support of the table, or a base of the table to deploy the adjustable arm supports and robotic arms from a position below the table. In some examples, the adjustable arm supports include at least four degrees of freedom that allow for adjustment of the position of a bar or rail to which the robotic arms are mounted. One of the degrees of freedom can allow the adjustable arm support to be adjusted vertically relative to the table. A robotic surgical system can include two adjustable arm supports, each supporting one or more robotic arms. The two adjustable arm supports can be independently adjusted. For example, each arm support can be adjusted to a different height relative to the table.

In a first aspect, a system can include a table configured to support a patient. The system can also include a column extending along a first axis between a first end and a second end. The first end can be coupled to the table. A base can be coupled to the second end of the column. The system can include a first arm support coupled to at least one of the table, column or the base by at least a first joint configured to allow adjustment along the first axis relative to the table. The first arm support can include a first bar having a proximal portion and a distal portion extending along a second axis different from the first axis. The first bar can be configured to support at least one robotic arm.

The system can include one or more of the following features in any combination: (a) wherein the first axis is a vertical axis and the first joint is configured to allow adjustment of the first bar in a vertical direction; (b) wherein the first joint comprises a motorized linear joint configured to move along the first axis; (c) a first robotic arm mounted to the first bar, the first robotic arm configured to translate along the second axis; (d) a second robotic arm mounted to the first bar, the second robotic arm configured to translate along the second axis; (e) wherein the second robotic arm is configured to translate along the second axis independently of the first robotic arm; (f) a third robotic arm mounted to the first bar; (g) wherein at least one of the first robotic arm, second robotic arm or third robotic arm holds a camera; (h) wherein at least one of the first robotic arm, second robotic arm or third robotic arm can be stowed under the table; (i) wherein the first arm support comprises a second joint configured to adjust a tilt angle of the first bar; (j) wherein the second joint comprises a motorized rotational joint configured to rotate around a third axis that is different than the first axis; (k) wherein the first arm support comprises a third joint and a bar connector, the bar connector mechanically coupling the first bar with the third joint; (l) wherein the third joint comprises a motorized rotational joint configured to pivot the bar connector about a fourth axis that is different than the first axis; (m) wherein the third joint is configured to pivot the bar connector to adjust a positioning of the first bar relative to the column; (n) wherein: the third joint is positioned at a first end of the bar connector, the first end of the bar connector coupled to the column, an additional joint is positioned at a second end of the bar connector, the second end of the bar connector coupled to the first bar, and the additional joint is mechanically constrained to the third joint such that the additional joint and the third joint rotate together; (o) wherein the additional joint is mechanically constrained to the third joint via a four-bar linkage; (p) wherein the additional joint is mechanically constrained to the third joint such that an orientation of the first bar does not change as the bar connector pivots; (q) wherein the first bar is capable of translation along a length of the table such that the first bar can extend beyond an end of the table; (r) wherein the first bar is further coupled to the column by at least one fourth joint configured to allow translation of the first bar relative to the column along the second axis; (s) wherein the first arm support is configured to be positioned on a first side of the table, and wherein the system further comprises a second arm support coupled to at least one of the table, column or base and configured to be positioned on a second side of the table; (t) wherein the second side is opposite the first side; (u) wherein the second arm support comprises a second bar extending along a fifth axis by at least a first joint configured to allow adjustment of the second along the first axis; (v) wherein the first arm support and the second arm support are configured to be independently adjustable, such that the first arm support can be moved to a first height and the second arm support can be independently moved to a second height different than the first height; (x) wherein the first arm support is configured to be stored below the table; and/or (y) wherein the base comprises one or more wheels configured such that the system is mobile.

In another aspect, a system can include a table configured to support a patient. The system can include a column extending along a first axis between a first end and a second end. The first end can be coupled to the table. A base can be coupled to the second end of the column. The system can include a first arm support comprising a first bar having a proximal portion and a distal portion extending along a second axis, the first bar coupled to at least one of the table, column or base by at least a first joint configured to allow adjustment of the first bar along the first axis, the first arm support configured to support at least one robotic arm. The system can also include a second arm support comprising a second bar having a proximal portion and a distal portion extending along a third axis coupled to the column by at least a second joint configured to allow adjustment of the second bar along the first axis, the second arm support configured to support at least another robotic arm. In some embodiments, the first arm support and the second arm support are configured such that the position of the first bar and the second bar along the first axis can be adjusted independently.

The system can include one or more of the following features in any combination: (a) wherein the first axis is a vertical axis, the first joint is configured to allow adjustment of the first bar in a vertical direction, the second joint is configured to allow adjustment of the second bar in the vertical direction, and wherein the first bar and the second bar can be adjusted to different heights; (b) wherein the first arm support is configured to be positioned on a first side of the table, and the second arm support is configured to be positioned on a second side of the table; (c) wherein the second side is opposite the first side; (d) wherein: the first arm support comprises a third joint configured to adjust a tilt angle of the second axis of the first bar relative to the surface of the table, and the second arm support comprises a fourth joint configured to adjust a tilt angle of the third axis of the second bar relative to the surface of the table; (e) wherein the tilt angle of the first bar axis and the tilt angle of the second bar axis can be adjusted independently; (f) wherein the first arm support further comprises a first bar connector that is pivotally coupled to the column by at least a fifth joint, and the second arm support further comprises a second bar connector that is pivotally coupled to the column by at least a sixth joint; (g) wherein the first bar connector and the second bar connector can be pivoted independently; (h) wherein the first further comprises a seventh joint configured to allow translation of the first bar relative to the column along the second axis, and the second arm support further comprises an eighth joint configured to allow translation of the second bar relative to the column along the third axis; (i) wherein the translation of the first bar along the first bar axis and the translation of the second bar along the second bar axis can be adjusted independently; (j) wherein the first and second arm supports are configured to be stored below the table; (k) wherein one or more of the first joint and the second joint are motorized or controlled by hydraulics; (l) wherein the first arm supports at least two robotic arms that are linearly translatable relative to one another; and/or (m) multiple robotic arms on the first arm support and multiple robotic arms on the second arm support, wherein the number of arms on the first arm support is equal to the number of arms on the second arm support.

In another aspect, an arm support is disclosed. The arm support can include a bar extending along a first axis. The bar can be configured to support at least one robotic arm such that the at least one robotic arm can translate along the first axis. The bar can be configured to couple to a column supporting a table. The arm support can include a first joint configured to facilitate adjusting a vertical position of the bar along a second axis of the column, a second joint configured to facilitate adjusting a tilt angle of the first axis relative to a surface of the table, a bar connector configured to pivotally couple to the column by at least a third joint, and a fourth joint configured to facilitate translation of the bar along the first axis.

The arm support can include one or more of the following features in any combination: (a) wherein one or more of the first joint, second joint, third joint and fourth joint are motorized or controlled by hydraulics; (b) wherein the second axis is a vertical axis and the first joint is configured to allow adjustment of the bar in a vertical direction; (c) wherein the first joint comprises a linear joint configured to move along the second axis; (d) wherein the second joint comprises a rotational joint configured to rotate around a third axis that is different than the second axis; (e) wherein the third joint comprises a rotational joint configured to pivot the bar connector about a fourth axis that is different than the first axis; (f) wherein the third joint is configured to pivot the bar connector to adjust a positioning of the bar relative to the column; (g) wherein the third joint is positioned at a first end of the bar connector, the first end of the bar connector configured to couple to the column, and wherein an additional joint is positioned at a second end of the bar connector, the second end of the bar connector coupled to the bar, and wherein the additional joint is mechanically constrained to the third joint such that the additional joint and the third joint rotate together; (h) wherein the additional joint is mechanically constrained to the third motorized joint via a four-bar linkage; (i) wherein the additional joint is mechanically constrained to the third motorized joint such that an orientation of the bar does not change as the bar connector pivots; and/or (j) wherein the fourth joint comprises a linear joint.

In another aspect, disclosed is a system that can include a table configured to support a patient positioned on a surface of the table. The system can include a column extending along a first axis between a first end and a second end. The first end can be coupled to the table. A base can be coupled to the second end of the column. The system can include an arm support comprising a bar extending along a second axis. The bar can be coupled to at least one of the table, column, or base by a first joint configured to allow adjustment of the bar along the first axis. The arm support can be configured to support at least one robotic arm. The system can also include at least one computer-readable memory having stored thereon executable instructions, and at least one processor in communication with the at least one computer-readable memory and configured to execute the instructions to cause the system to at least adjust a position of the bar along the first axis in response to receiving a command.

The system can include one or more of the following features in any combination: (a) wherein the command comprises a command to adjust a position of a robotic medical tool coupled to a robotic arm coupled to the arm support; (b) wherein the at least one processor is further configured to execute the instructions to cause the system to at least adjust a position of the bar in response to a clinician selected procedure; (c) wherein the at least one processor is further configured to execute the instructions to cause the system to at least adjust a position of the bar to avoid a collision between the robotic arm and at least one of: the table, a patient, an additional robotic arm, and a medical imaging device; and/or (d) one or more of: a second joint configured to allow the bar to tilt to adjust an angle of the bar axis relative to a surface of the table, a bar connector configured to pivotally couple to the column by at least a third joint, a fourth joint configured to allow translation of the bar relative to the column along the bar axis, and wherein the least one processor is further configured to execute the instructions to cause the system to at least control at least one of the second joint, the third joint, and the fourth joint to adjust the position of the bar.

In another aspect, disclosed is a method that can include providing a table configured to support a patient positioned on a surface of the table; providing a column extending along a first axis between a first end and a second end, the first end coupled to the table; providing a base coupled to the second end of the column; providing an arm support comprising a bar extending along a bar axis coupled to at least one of the table, column or base by at least a first joint configured to allow adjustment of the bar along the first axis, the arm support configured to support at least one robotic arm; and actuating the first joint to adjust a position of the bar along the first axis.

The method can include one or more of the following features in any combination: (a) providing a first robotic arm mounted to the first bar; and translating the first robotic arm the second axis; (b) providing a second robotic arm mounted to the first bar, and translating the second robotic arm the second axis; (c) wherein the second robotic arm is configured to translate along the second axis independently of the first robotic arm; (d) providing a third robotic arm mounted to the first bar; (e) wherein at least one of the first robotic arm, second robotic arm or third robotic arm holds a camera; (f) wherein at least one of the first robotic arm, the second robotic arm, or the third robotic arm can be stowed under the table; (g) wherein the first arm support comprises a second joint configured to adjust a tilt angle of the first bar, and wherein the method further comprises adjusting the tilt angle of the bar by actuating the second joint; (h) wherein the second joint comprises a motorized rotational joint configured to rotate around a third axis that is different than the first axis; (i) wherein the first arm support comprises a third joint and a bar connector, the bar connector mechanically coupling the first bar with the third joint; (j) actuating the third joint to pivot the bar connector to adjust a positioning of the first bar relative to the column; (k) wherein the first bar is capable of translation along a length of the table such that the first bar can extend beyond an end of the table; (l) wherein the first bar is further coupled to the column by at least one fourth joint configured to allow translation of the first bar relative to the column along the second axis, and wherein the method further comprise translating the first bar relative to the column along the second axis; (m) providing a second arm support coupled to at least one of the table, column or base and configured to be positioned on a second side of the table; and/or (n) moving the first arm support to a first height, and moving the second arm support to a second height different than the first height.

In another aspect, disclosed is a method that includes: receiving a command regarding positioning of at least one of: a first robotic arm; a medical instrument coupled to an end effector of the robotic first arm; and an arm support coupled to a base of the first robotic arm and to a column supporting a patient-support table, wherein the arm support comprises at least one joint and a bar configured to support the first robotic arm; and actuating, based on the received command, the at least one joint to adjust a position of the arm support along a vertical axis of the column.

The method may include one or more of the following features in any combination: (a) wherein a first command actuates the at least one joint to adjust the position of the arm support along a vertical axis of the column, a second command actuates a second joint for pivoting up the arm support, a third command actuates a third joint for tilting the arm support and a fourth command causes longitudinal translation of the arm support; (b) wherein a second robotic arm is coupled to the bar of the arm support; (c) raising the arm support, the first robotic arm, and the second robotic arm from a stowed position below the table; positioning the arm support, the first robotic arm and the second robotic arm adjacent the table; adjusting a position of the arm support relative to the table via at least one of the first command, second command, third command, or fourth command; and adjusting a position of the first robotic arm relative to the second robotic arm along the bar of the support joint in preparation for a surgical procedure; (d) wherein the arm support is positioned below an upper surface of the table; and/or (e) a controller for executing one or more commands based on a kinematics model, wherein the one or more commands control the positioning of one or more of the first robotic arm; the medical instrument coupled to an end effector of the robotic first arm; and an arm support coupled to a base of the first robotic arm and to a column supporting a patient-support table, wherein the arm support comprises at least one joint and a bar configured to support the first robotic arm.

In another aspect, disclose is a system that can include a table configured to support a patient positioned on a surface of the table, one or more supports for the table, and an arm support for holding one or more arms adjustable relative to the table, wherein a height of the arm support is adjustable relative to the table.

Reference will now be made in detail to several embodiments, examples of which are illustrated in the accompanying figures. It is noted that wherever practicable similar or like reference numbers may be used in the figures and may indicate similar or like functionality. The figures depict embodiments of the described system (or method) for purposes of illustration only. One skilled in the art will readily recognize from the following description that alternative embodiments of the structures and methods illustrated herein may be employed without departing from the principles described herein.

DETAILED DESCRIPTION

I. System Overview

Figure 1:
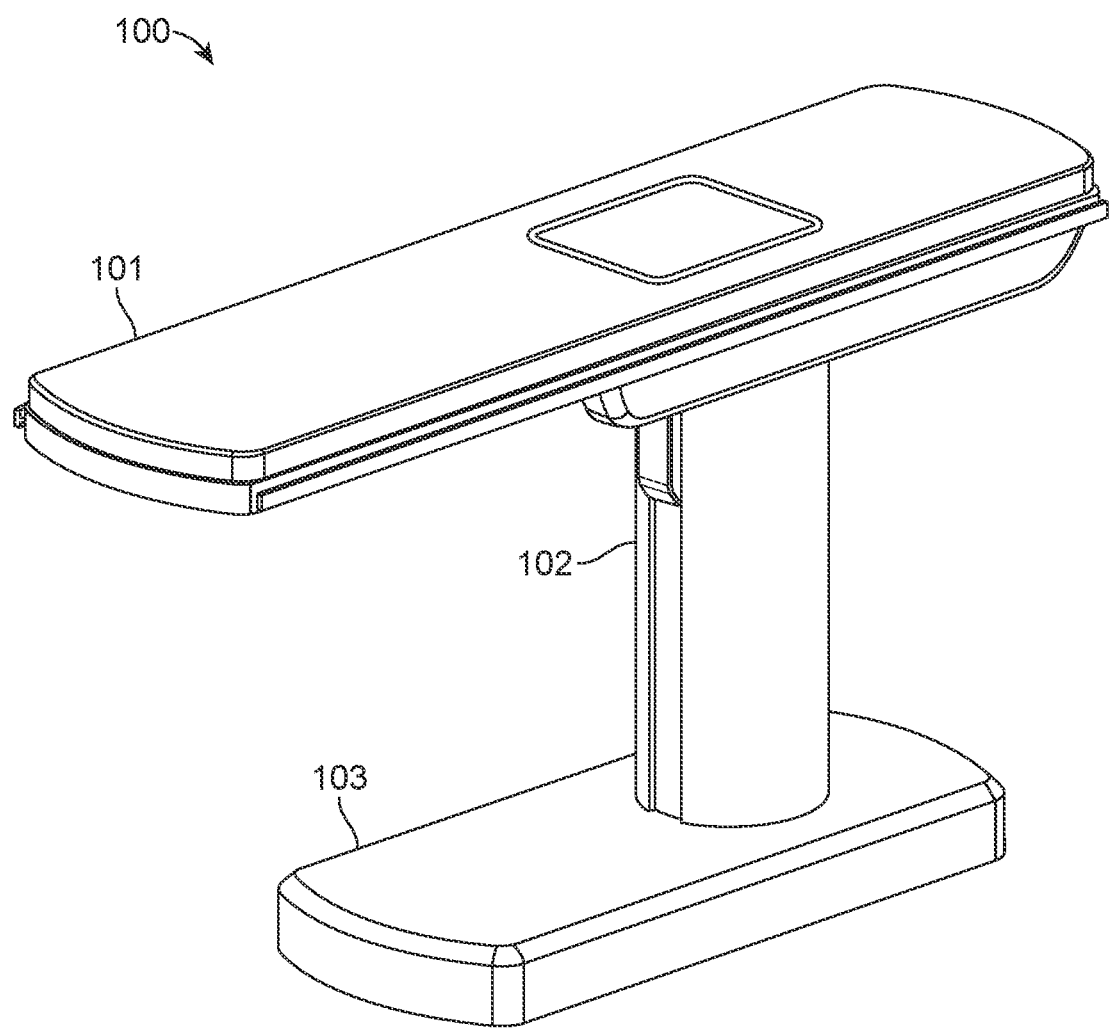
FIG. 1 is an isometric view of a surgical robotics system according to an embodiment.

FIG. 1 is an isometric view of a surgical robotics system 100 according to an embodiment. A user, e.g., a physician or assistant, uses the surgical robotics system 100 to perform robotically-assisted surgery on a patient. The surgical robotics system 100 includes a table 101, column 102, and base 103 physically coupled together. Although not shown in FIG. 1, the table 101, column 102, and/or base 103 may house, connect to, or use electronics, fluidics, pneumatics, aspiration, or other electrical and mechanical components that support the function of the surgical robotics system 100.

The table 101 provides support for a patient undergoing surgery using the surgical robotics system 100. Generally, the table 101 is parallel to the ground, though the table 101 may change its orientation and configuration to facilitate a variety of surgical procedures. The table 101 is further described with reference to FIGS. 2A-I in Section II. Table.

The column 102 is coupled to the table 101 on one end and coupled to the base 103 on the other end. Generally, the column 102 is cylindrically shaped to accommodate column rings coupled to the column 102, which are further described with reference to FIGS. 5A-E in Section V. Column Ring, however the column 102 may have other shapes such as oval or rectangular. The column 102 is further described with reference to FIGS. 3A-B in Section III. Column.

The base 103 is parallel to the ground and provides support for the column 102 and the table 101. The base 103 may include wheels, treads, or other means of positioning or transporting the surgical robotics system 100. The base 103 is further described with reference to FIGS. 8A-E in Section VIII. Base.

Alternative views and embodiments of the surgical robotics system 100 including the above mentioned components are further illustrated and described at least in U.S. Provisional Application No. 62/162,486 filed May 15, 2015 and U.S. Provisional Application No. 62/162,467 filed May 15, 2015.

II. Table

Figure 2A:
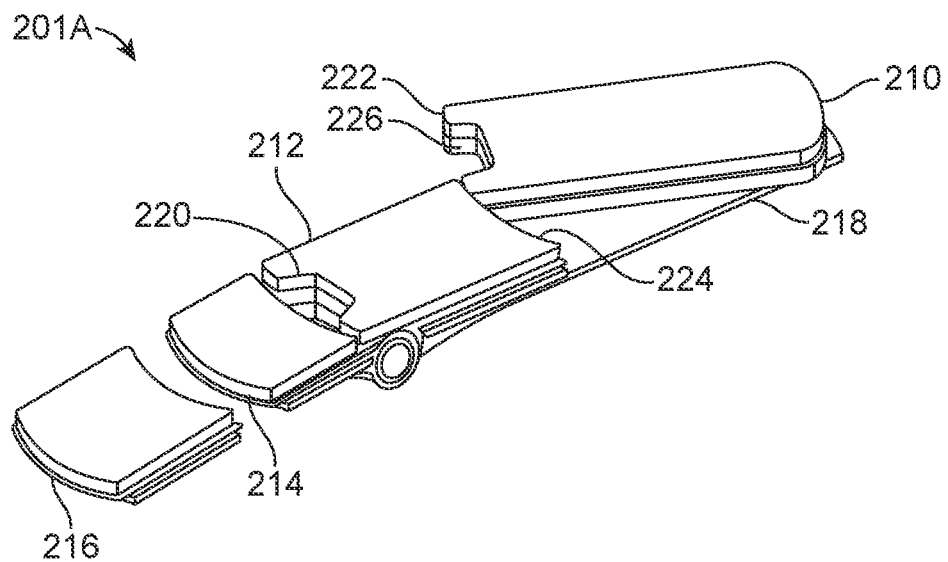
FIG. 2A is an isometric view of a table of the surgical robotics system according to one embodiment.

FIG. 2A is an isometric view of a table 201A of the surgical robotics system 100 according to one embodiment.

The table 201A is an embodiment of the table 101 in FIG. 1. The table 201A includes a set of one or more segments. Generally, a user changes the configuration of the table 201A by configuring the set of segments. The surgical robotics system 100 may also configure the segments automatically, for example, by using a motor to reposition a segment of the set of segments. An example set of segments is shown in FIG. 2A, and includes a swivel segment 210, center segment 212, foldable segment 214, detachable segment 216, and table base 218. The swivel segment 210, center segment 212, and foldable segment 214 are coupled to the table base 218. FIG. 2A shows the detachable segment 216 separated from the table base 218, though the detachable segment 216 may also be coupled to the table base 218. In various implementations, additional or fewer segments may be used.

An advantage of configuring the set of segments of the table 201A is that a configured table 201A may provide greater access to a patient on the table 201A. For instance, the surgical robotics system 100 performs a surgical procedure on the patient that requires access to the groin area of the patient. When a patient is laying face-up on a typical surgical bed, there is more access to the patient's head, arms, and legs than to the patient's groin area. Since the groin area is located toward the center of the patient's body, the legs often obstruct access to the groin area. The detachable segment 216 is detachable from the table 201A. The table 201A without the detachable segment 216 provides greater access to the groin area of a patient lying on the table 201A with the patient's head toward the side of the table 201A with the swivel segment 210. In particular, removing the detachable segment 216 opens more space, for example, to insert a surgical instrument into the groin area. If additional space is required to access the groin area, the foldable segment 214 may be folded down, away from the patient (further described in FIG. 2H). The center segment 212 includes a cutout section 220, which also provides greater access to the groin area.

The swivel segment 210 pivots laterally relative to the table 201A. The swivel segment 210 includes an arcuate edge 222 and the center segment 212 also includes in arcuate edge 224. Due to the arcuate edges, there is minimal gap between the swivel segment 210 and the center segment 212 as the swivel segment 210 pivots away from or toward the table 201A. A configuration of the table 201A with the swivel segment 210 pivoted away from the table 201A provides greater access to the groin area because the other segments of the table 201A are not obstructing the groin area. An example of this configuration is further described with respect to FIGS. 7C-D in Section VII. A. Lower Body Surgery. Additionally, the swivel segment 210 also includes a cutout section 226, which provides yet greater access to the groin area.

Figure 2B:
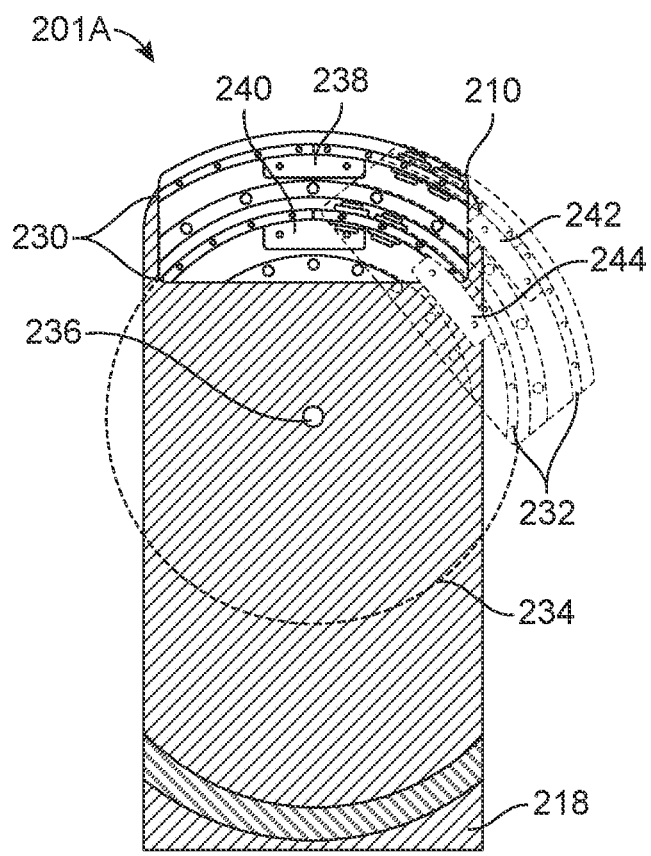
FIG. 2B is a top view of the table according to one embodiment.

FIG. 2B is a top view of the table 201A according to one embodiment. Specifically, FIG. 2B shows the table base 218 with a partial cutaway view and a portion of the swivel segment 210. Components inside the swivel segment 210 are exposed for purposes of illustration. The table base 218 includes double curved rails 230, that is, two curved linear rails (also referred to as a first bearing subassembly). The swivel segment 210 also includes double curved rails 232 (also referred to as a second bearing subassembly). The first bearing assembly coupled to the second bearing assembly may be referred to as a bearing mechanism. The double curved rails 230 of the table base 218 engage with the double curved rails 232 of the swivel segment 210. Both double curved rails are concentric to a virtual circle 234. The swivel segment 210 pivots about an axis passing through a point 236 at the center of the virtual circle 234 perpendicular to the plane of the table base 218. The double curved rails 230 of the table base 218 include a first carriage 238 and a second carriage 240. Similarly, the double curved rails 232 of the swivel segment 210 include a first carriage 242 and a second carriage 244. The carriages provide structural support and negate moment loads, which enables the double curved rails to support high cantilevered loads up to at least 500 pounds. For instance, pivoting a patient away from the table 201A generates a high cantilevered load on the double curved rails supporting the patient's weight. The table base 218 and swivel segment 210 may include additional load-sharing components such as rollers, cam followers, and bearings. In some embodiments, the swivel segment 210 and table base 218 each include a single curved rail instead of double curved rails. Further, each curved rail may include additional or fewer carriages.

Figure 2C:
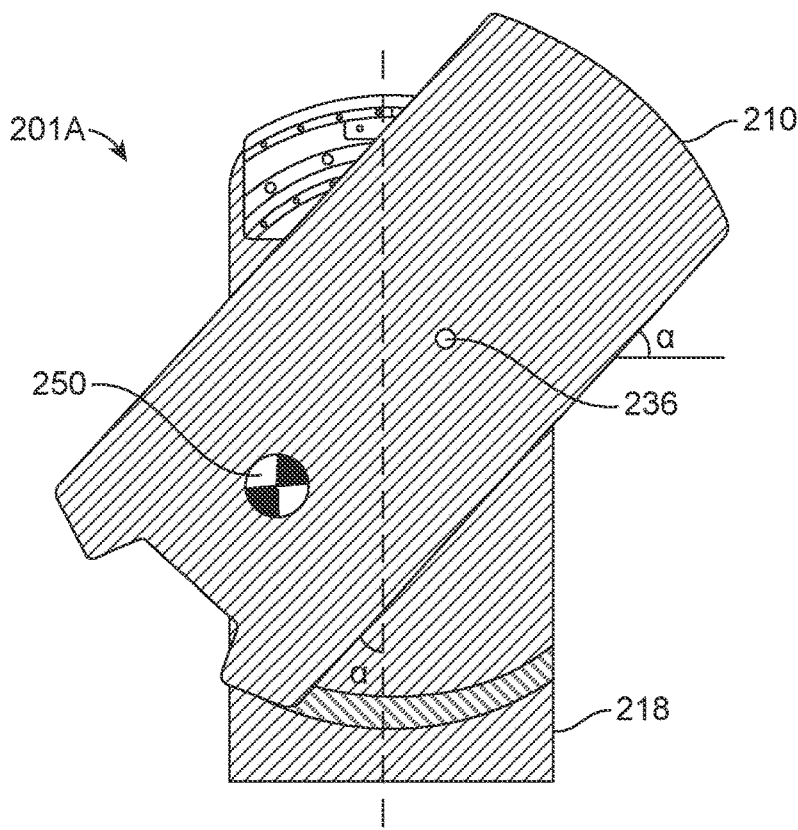
FIG. 2C is a top view of a swivel segment of a table according to one embodiment.
Figure 2D:
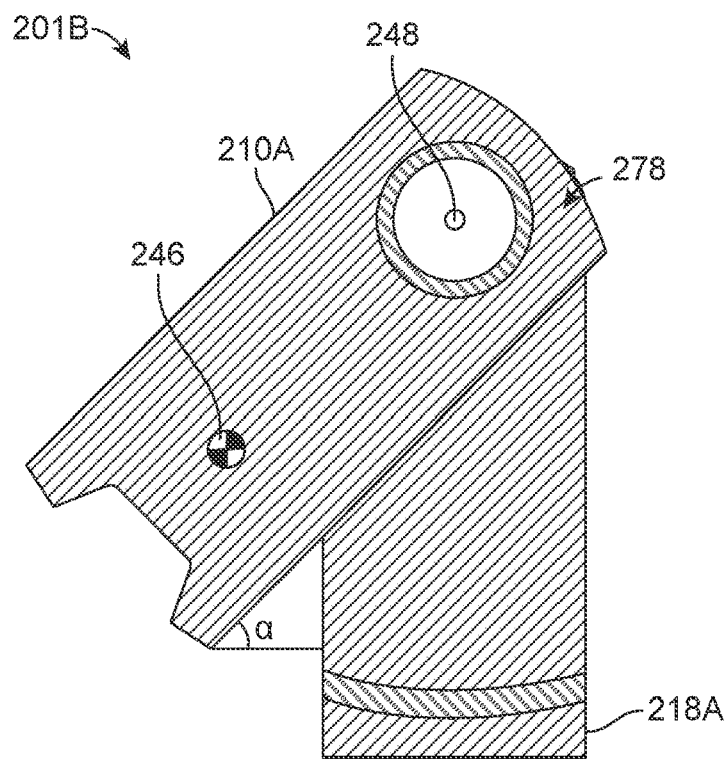
FIG. 2D is a top view of a swivel segment of the table according to one embodiment.

FIG. 2C is a top view of the swivel segment 210 of the table 201A according to one embodiment. The center of mass 250 illustrates the center of mass of the swivel segment 210 and a patient (not shown) lying on the swivel segment 210. The swivel segment 210 is pivoted at an angle α about the axis 236. Compared to the center of mass 246 shown in FIG. 2D, the center of mass 250 is closer toward the table base 218 (corresponding to table base 218B in FIG. 2D), even though the swivel segments in both FIG. 2C and FIG. 2D are each pivoted at the same angle α. Keeping the center of mass 250 close toward the table 218 helps the swivel segment 210 support greater cantilever loads—due to the patient—without tipping over the surgical robotics system. In some embodiments, the swivel segment 210 may be rotated up to an angle of 30 degrees or 45 degrees relative to table base 218, while keeping the center of mass of the swivel segment 210 above the table 201A.

FIG. 2D is a top view of a swivel segment 210A of a table 201B according to one embodiment. Specifically, the table 201B includes a table base 218A and a swivel segment 210A. The table 201B does not include double curved rails, but instead includes a swivel mechanism 278 that is further described below with reference to FIGS. 2E-G. The center of mass 246 illustrates the center of mass of the swivel segment 210A and a patient (not shown) lying on the swivel segment 210A. The swivel segment 210A is pivoted at an angle α about an axis 248. Accordingly, the center of mass 246 is positioned off of the table base 218A.

Figure 2E:
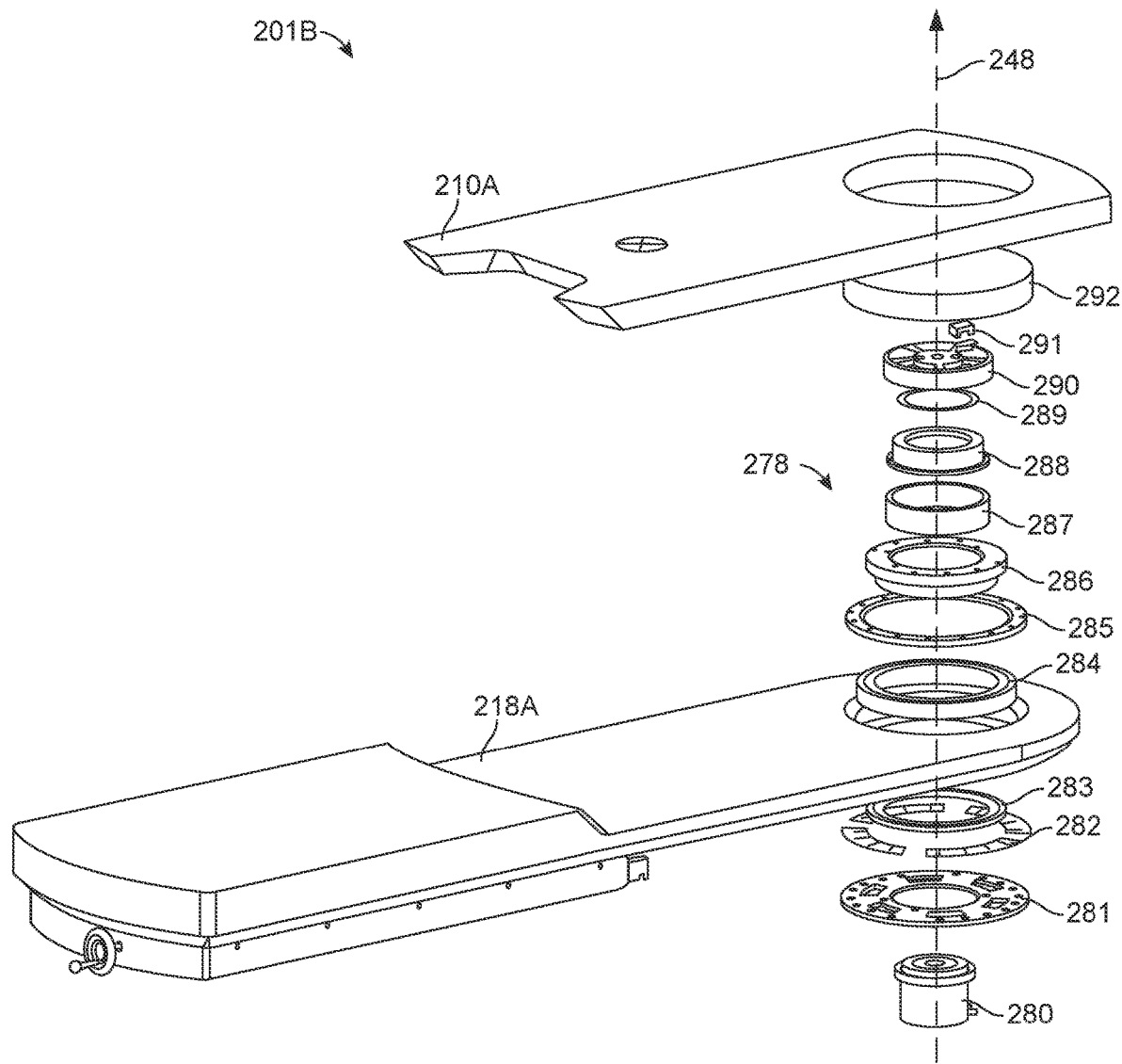
FIG. 2E is an isometric exploded view of components of a swivel mechanism according to one embodiment.

FIG. 2E is an isometric exploded view of components of a swivel mechanism 278 (which can also be referred to as a bearing mechanism) of the table 201B according to one embodiment. The swivel mechanism 278 includes a first bearing subassembly coupled to a second bearing subassembly. In particular, the swivel mechanism 278 includes a harmonic drive motor 280, static plate 281, shim 282, inner bearing race 283, bearing 284, outer bearing race cleat 285, inner bearing race support 286, static ring 287, motor housing mount 288, encoder strip 289, drive plate 290, encoder sensor 291, and swivel insert 292. The motor housing mount 288 is stationary relative to the table base 218A. The harmonic drive motor 280 rotates the swivel segment 210A about the axis 248. The first bearing subassembly includes the components described above that are coupled to the table base 218A. The second bearing subassembly includes the components described above that are coupled to the swivel segment 210A.

Figure 2F:
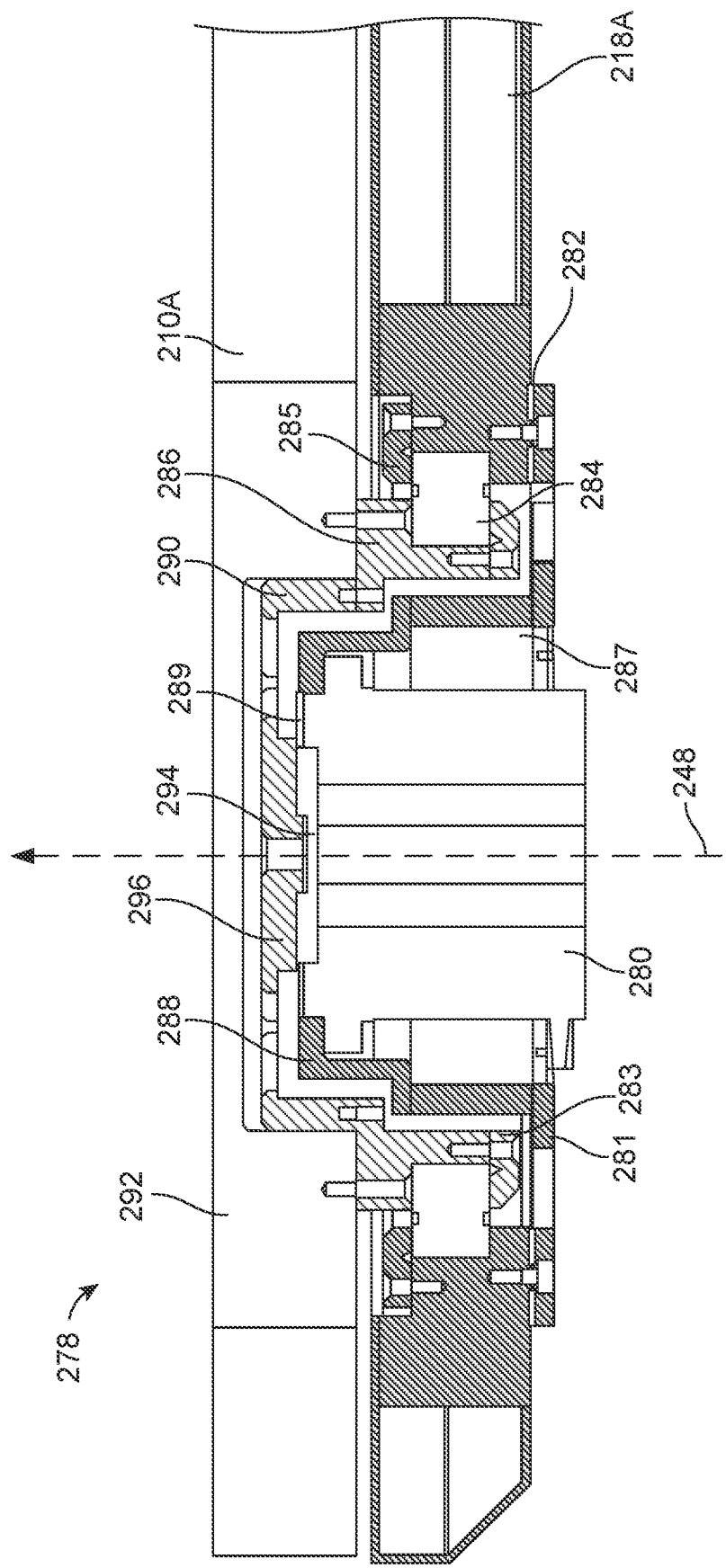
FIG. 2F is a cross sectional view of the swivel mechanism shown in FIG. 2E according to one embodiment.

FIG. 2F is a cross sectional view of the swivel mechanism 278 shown in FIG. 2E according to one embodiment. The harmonic drive motor 280 is coupled to the motor housing mount 288. The motor housing mount 288 is coupled to the static ring 287 and the static plate 281. The static plate 281 is coupled to the table base 218A using the shim 282 such that the harmonic drive motor 280 is also stationary relative to the table base 218A.

The harmonic drive motor 280 includes a driving axle 294 coupled to a driving face 296 such that the driving axle 294 and driving face 296 rotate together. The driving face 296 is coupled to the drive plate 290. The drive plate 290 is coupled to the inner bearing race support 286. The inner bearing race support 286 is coupled to the swivel insert 292 and the inner bearing race cleat 283. The inner bearing race support 286 is movably coupled to the table base 218A by the bearing 284 (e.g., a cross roller bearing). The swivel insert 292 is coupled to the swivel segment 210A such that rotating the driving axle 294 and driving face 296 causes the swivel segment 210A to rotate in the same direction. Though not shown in FIG. 2F, the swivel mechanism 278 may include additional components between the static plate 281 and the inner bearing race cleat 283 to provide additional stability, e.g., in the form of a physical hard stop. Further, though not shown in FIG. 2F, the encoder sensor 291 is coupled to the motor housing mount 288 by the encoder strip 289. The encoder sensor 291 records information about the rotation of the swivel segment 210A, e.g., the position of the swivel segment 210A up to an accuracy of 0.1 degrees at 0.01 degree resolution. FIG. 2F shows several screws (or bolts) that are used to couple components of the swivel mechanism, though it should be noted that the components may be coupled using other methods, e.g., welding, press fit, gluing, etc.

The swivel mechanism 278 allows the harmonic drive motor 280 to rotate the swivel segment 210A with precise control, while supporting a load of up to 500 pounds, e.g., from a patient lying on the swivel segment 210A. In particular, the harmonic drive motor 280 may rotate the swivel segment 210A up to a rotational velocity of 10 degrees per second, and up to 45 degrees in either direction about the axis 248. Further, the swivel segment 210A is rotated such that the maximum velocity of the center of mass of the patient is 100 millimeters per second, and the time to the maximum velocity is 0.5 seconds. In some embodiments, one of the bearings of the swivel mechanism is a cross roller bearing—e.g., with ball bearings with a bearing friction coefficient of approximately 0.0025—that helps further provide stability to allow the precise rotation of the swivel segment 210A, while maintaining cantilever loads from the patient's weight. The harmonic drive motor 280 can generate up to 33 Newton meters of torque to rotate the swivel segment 210A with the weight of the patient. In some embodiments, the harmonic drive motor 280 includes an internal brake with a holding torque of at least 40 Newton meters.

Figure 2G:
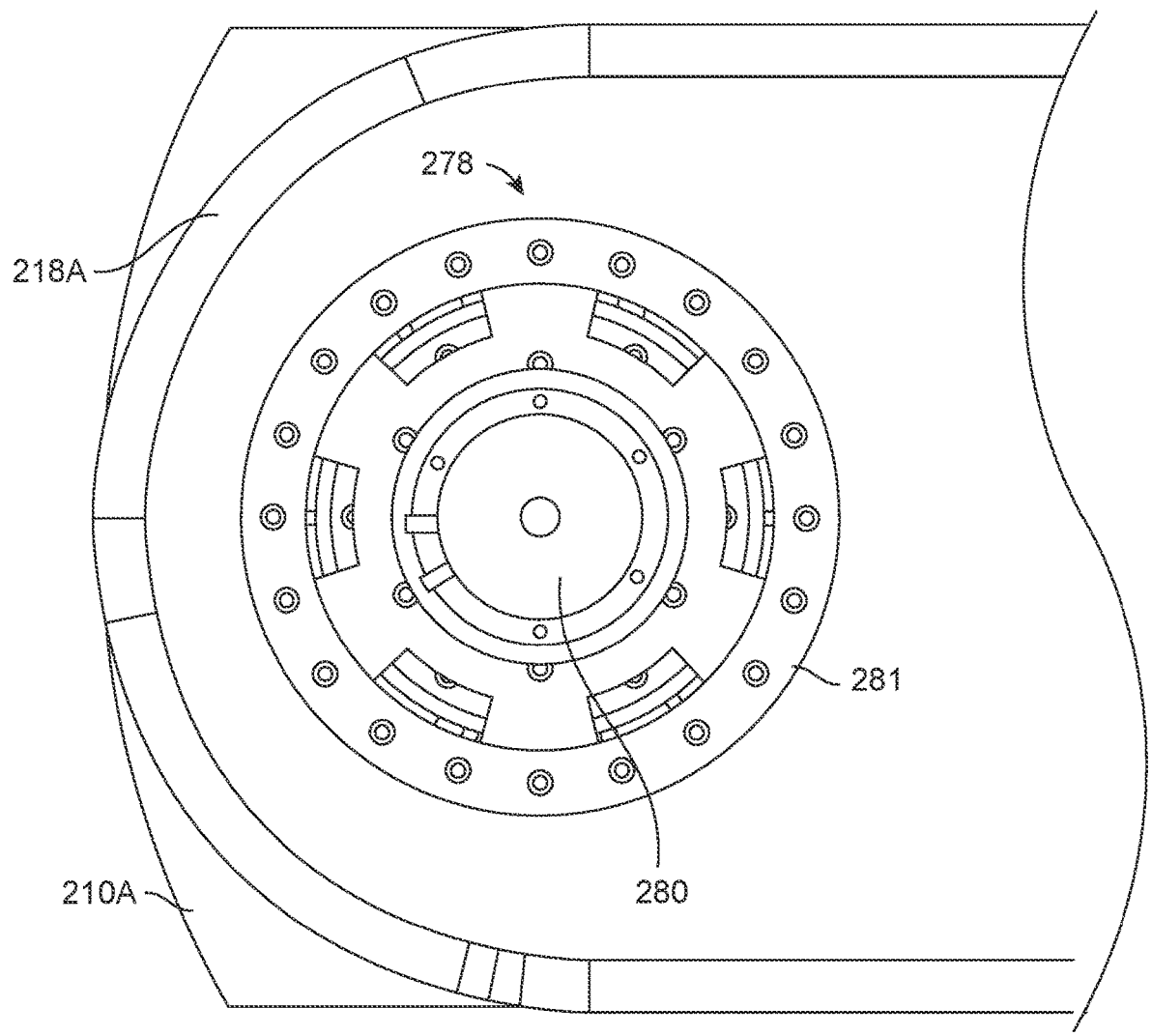
FIG. 2G is a bottom view of the swivel mechanism shown in FIG. 2E according to one embodiment.

FIG. 2G is a bottom view of the swivel mechanism shown in FIG. 2E according to one embodiment. The harmonic drive motor 280 is exposed such that electrical wires, e.g., from a column of the surgical robotics system, may be coupled to the harmonic drive motor 280 to provide control signals to the harmonic drive motor 280.

Figure 2H:
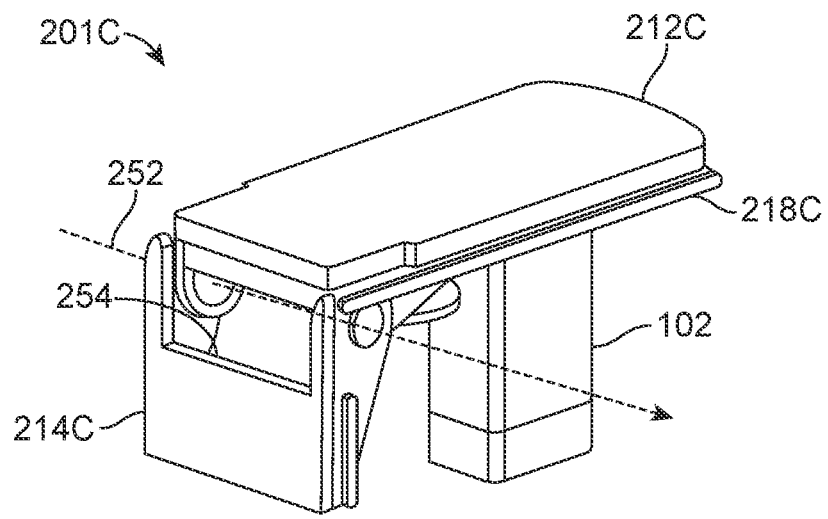
FIG. 2H is an isometric view of a folding segment of the table according to one embodiment.

FIG. 2H is an isometric view of a foldable segment 214C of a table 201C according to one embodiment. The table 201C is an embodiment of table 201A in FIG. 2A. The table 201C also includes a center segment 212C coupled to a table base 218C. The foldable segment 214C rotates using bearings about an axis 252 parallel to the table base 218C. The foldable segment 214C is rotated such that the foldable segment 214C is orthogonal to the table base 218C and the center segment 212C. In other embodiments, the foldable segment 214C may be rotated to other angles relative to the table base 218C and the center segment 212C. The foldable segment 214C includes a cutout section 254, for example, to provide greater access to a patient lying on the table 201C. In other embodiments, the foldable segment 214C does not include a cutout section.

Figure 2I:
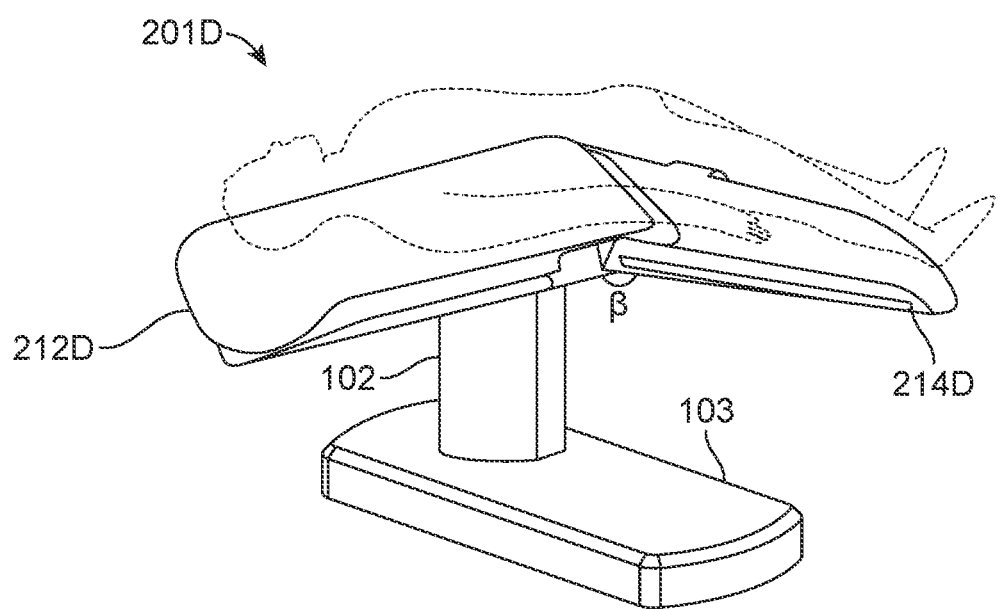
FIG. 2I is another isometric view of a folding segment of the table according to one embodiment.

FIG. 2I is another isometric view of a foldable segment 214D of a table 201D according to one embodiment. The table 201D is an embodiment of table 201A in FIG. 2A. The foldable segment 214D is rotated such that the foldable segment 214D and the table base 218D is positioned at an angle β relative to each other. The table 201D includes a mechanism for the foldable segment 214D and the center segment 212D to maintain the rotated position while supporting the weight of a patient on the table 201D. For example, the mechanism is a friction brake at the joint of the foldable segment 214D and the center segment 212D that holds the two segments at the angle β. Alternatively, the foldable segment 214D rotates about the center segment 212D using a shaft and the mechanism is a clutch that locks the shaft, and thus keeps the two segments at a fixed position. Though not shown in FIG. 2I, the table 201D may include motors or other actuators to automatically rotate and lock the foldable segment 214D to a certain angle relative to the center segment 212D. Rotating the foldable segment 214D is advantageous, for example, because the corresponding configuration of the table 201D provides greater access to the area around the abdomen of a patient lying on the table 201D.

Figure 2J:
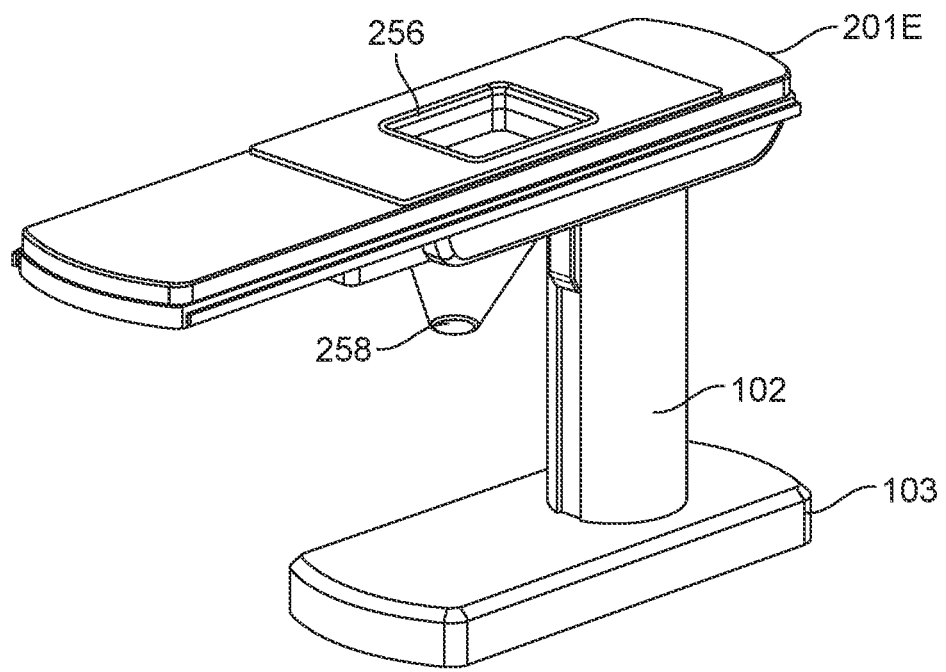
FIG. 2J is an isometric view of a trapdoor of the table according to one embodiment.

FIG. 2J is an isometric view of a trapdoor 256 of a table 201E according to one embodiment. The table 201E is an embodiment of table 201A in FIG. 2A. Specifically, the table 201E includes the trapdoor 256 and a drainage component 258 positioned below the trapdoor 256. The trapdoor 256 and drainage component 258 collect waste materials such as fluid (e.g., urine), debris (e.g., feces) that are secreted or released by a patient lying on the table during a surgical procedure. A container (not shown) may be positioned below the drainage component 258 to collect and store the waste materials. The trapdoor 256 and drainage component 258 are advantageous because they prevent waste materials from soiling or de-sterilizing equipment such as other components of the surgical robotic system 100 or other surgical tools in an operating room with the surgical robotic system 100.

Figure 2K:
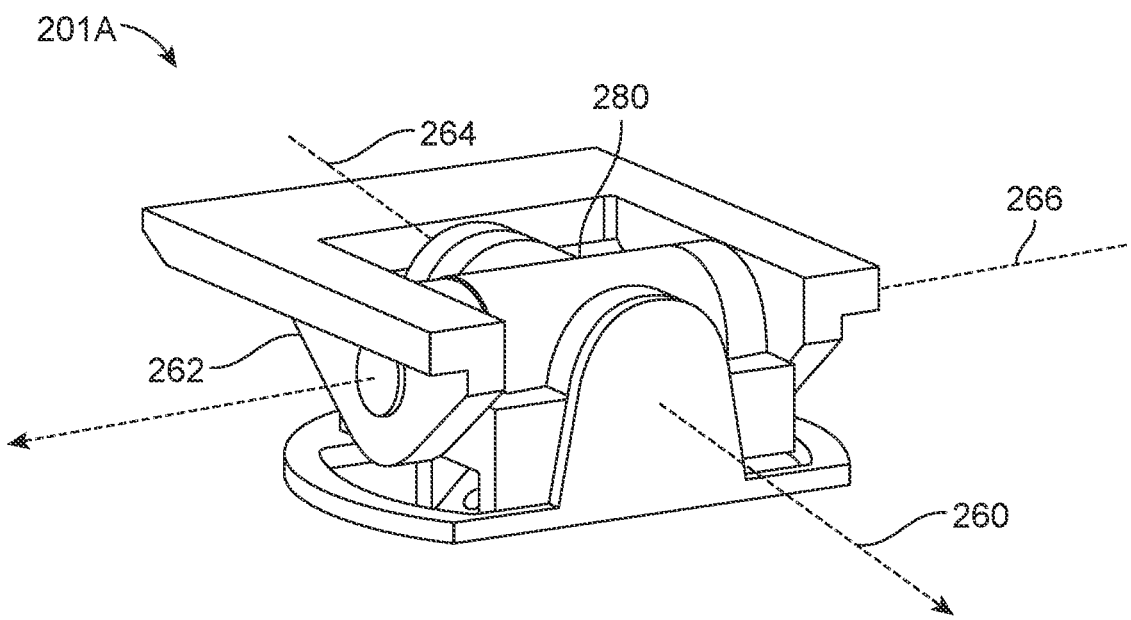
FIG. 2K is an isometric view of pivots of the table according to one embodiment.

FIG. 2K is an isometric view of pivots of the table 201A according to one embodiment. Specifically, the table 201A includes a first pivot 260 and a second pivot 262. The table 201A rotates about a first axis 264. A user, e.g., a physician, may rotate the table 201A about the first axis 264 or the second axis 266 manually or assisted by the surgical robotics system 100. The surgical robotics system 100 may also rotate the table 201A automatically, for example, by using control signals to operate a motor coupled to the first pivot 260 or the second pivot 262. The motor 280 is coupled to the first pivot 260. Rotation of the table 201A may provide greater access to certain areas of a patient lying on the table 201A during a surgical procedure. Specifically, the table 201A is configured to orient a patient lying on the table 201A in a Trendelenburg position by rotating about the first axis 264. Rotation of the table 201A is further described in FIGS. 2L-M.

Figure 2L:
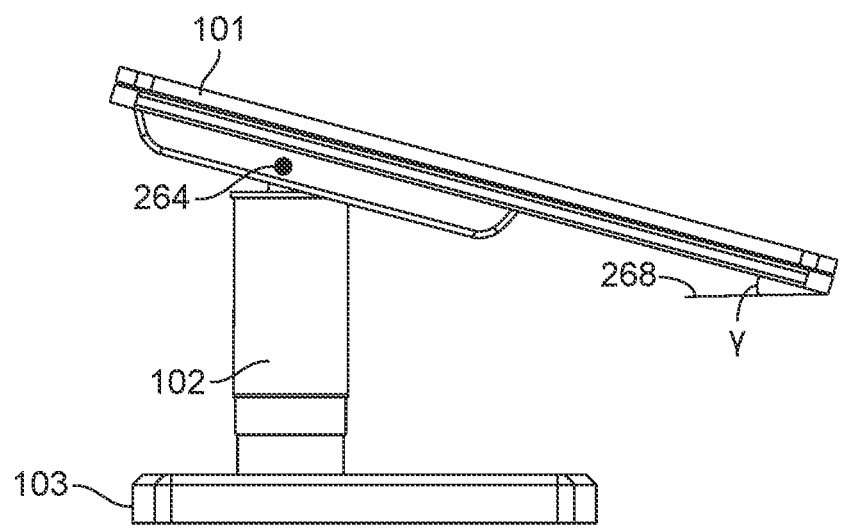
FIG. 2L is a side view of the table rotated about an axis of pitch according to one embodiment.

FIG. 2L is a side view of the table 201A rotated about the axis of pitch 264 according to one embodiment. Specifically, the table 201A is rotated to an angle γ relative to a plane 268 parallel to the ground.

Figure 2M:
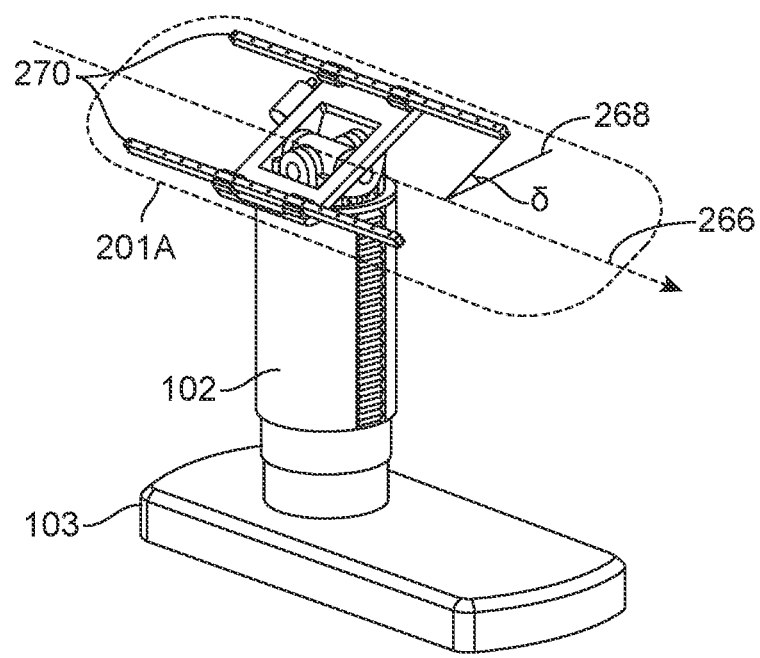
FIG. 2M is an isometric view of the table rotated about an axis of row according to one embodiment.

FIG. 2M is an isometric view of the table 201A rotated about the axis of row 266 according to one embodiment. Specifically, the table 201A is rotated to an angle δ relative to the plane 268 parallel to the ground. The table 201A is illustrated as transparent to expose components underneath the table 201A. The table includes a set of rails 270. The table 201A may translate laterally along an axis 266 parallel to the set of rails 270. The surgical robotics system 100 translates the table 201A laterally using, for example, a motor or other means of actuation (not shown). A user of the surgical robotics system 100 may also manually translate the table 201A, or with assistance from the surgical robotics system 100.

Alternative views and embodiments of the table 201A including the above mentioned components are further illustrated and described at least in U.S. Provisional Application No. 62/235,394 filed Sep. 30, 2015.

III. Column

Figure 3A:
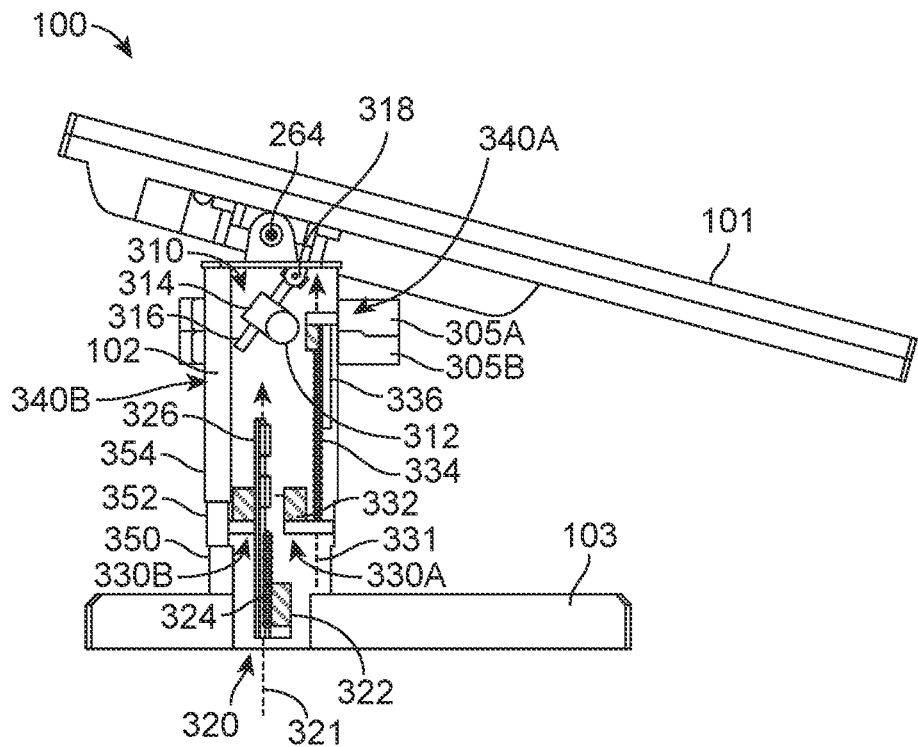
FIG. 3A is a side cutaway view of a column of the surgical robotics system according to one embodiment.

FIG. 3A is a side cutaway view of the column 102 of the surgical robotics system 100 according to one embodiment. The column 102 includes electrical and mechanical and other types of components to perform functions of the surgical robotics system 100. The column 102 includes a pitch rotation mechanism 310, column telescoping mechanism 320, ring telescoping mechanisms 330A and 330B, and ring rotation mechanisms 340A and 340B. The ring rotation mechanisms 340A and 340B are further described in FIG. 3B.

The surgical robotics system 100 rotates the table 101 about the axis of pitch 264 (also illustrated previously in FIGS. 2K-L) using the pitch rotation mechanism 310. The pitch rotation mechanism 310 includes a pitch rotation motor 312, right angle gearbox 314, pitch rotation lead screw 316, and pitch rotation bracket 318. The pitch rotation motor 312 is coupled to the right angle gearbox 314. The pitch rotation motor 312 is orthogonal to the pitch rotation lead screw 316. The pitch rotation lead screw 316 is movably coupled to the pitch rotation bracket 318. The right angle gearbox 314 is coupled to the pitch rotation lead screw 316. Output rotation of the pitch rotation motor 312 causes translational motion of the pitch rotation lead screw along an axis 311. Accordingly, translational motion of the pitch rotation lead screw 318 causes the table 101 to rotate about the axis of pitch 264.

The surgical robotics system 100 translates the table vertically using the column telescoping mechanism 320. The column telescoping mechanism 320 includes a column telescoping motor 322, column telescoping lead screw 324, and column telescoping rail 326. The column telescoping motor 322 is coupled to the column telescoping lead screw 324. The column telescoping motor 322 and the column telescoping lead screw 324 are stationary relative to the base 103. The column telescoping lead screw 324 is engaged with the column telescoping rail 326. Output rotation of the column telescoping motor 322 causes the column telescoping rail 326 to translate along a vertical axis 321 along the column telescoping lead screw 324. As the column telescoping rail 326 translates in the positive direction along the vertical axis 321, the height of the column 102 and the table 101 increases.

The column 102 also includes a lower column segment 350, middle column segment 352, and upper column segment 354. The lower column segment 350 is coupled to the base 103 and stationary relative to the base 103. The middle column segment 352 is movably coupled to the lower column segment 350. The upper column segment 354 is movably coupled to the middle column segment 352. In other embodiments, a column 102 may include additional or fewer column segments.

The upper column segment 354 and/or the middle column segment 352 also translate along the vertical axis 321 to extend the height of the column 102. Similarly, as the column telescoping rail 326 translates in the negative direction along the vertical axis 321, the height of the column 102 and the table 101 decreases. Further, the upper column segment 354 and/or the middle column segment 352 also translate along the vertical axis 321, collapsing over the lower column segment 350. A table 101 with adjustable height is advantageous because the table 101 facilitates a variety of surgical procedures. Specifically, one surgical procedure requires a patient lying on the table 101 to be positioned at a height lower than the height of a patient lying on the table 101 for a different surgical procedure. In some embodiments, the column telescoping mechanism 320 uses other means of actuation such as hydraulics or pneumatics instead of—or in addition to—motors.

The surgical robotics system 100 translates column rings 305A and 305B vertically using the ring telescoping mechanisms 330A and 330B. The ring telescoping mechanism 330A includes a ring telescoping motor 332, ring telescoping lead screw 334, and ring telescoping rail 336. Column rings are further described with reference to FIGS. 5A-E in Section V. Column Ring. Column rings 305A and 305B are movably coupled to the column 102 and translate along a vertical axis 331. Generally, a column 102 includes a ring telescoping mechanism for each column ring of the column 102. Specifically, the column 102 includes ring telescoping mechanism 330A and second ring telescoping mechanism 330B. The ring telescoping motor 332 is coupled to the ring telescoping lead screw 334. The ring telescoping motor 332 and the ring telescoping lead screw 334 are stationary relative to the base 103. The ring telescoping lead screw 334 is engaged with the ring telescoping rail 336. The ring telescoping rail 336 is coupled to the column ring 305A. Output rotation of the ring telescoping motor 332 causes the ring telescoping rail 336 to translate along the vertical axis 331 and along the ring telescoping lead screw 334. As the ring telescoping rail 336 translates in the positive direction or negative direction along the vertical axis 331, the height of a corresponding column ring increases or decreases, respectively.

Figure 3B:
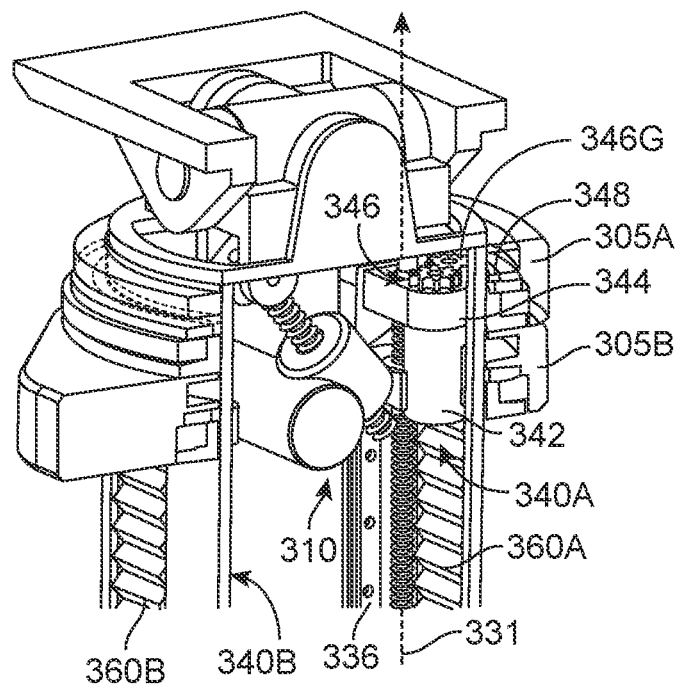
FIG. 3B is an isometric cutaway view of the column according to one embodiment.

FIG. 3B is an isometric cutaway view of the column 102 according to one embodiment. The column 102 includes a first accordion panel 360A and a second accordion panel 360B. The accordion panels 360A and 360B extend or fold as the surgical robotics system 100 translates column rings 305A and 305B in the positive direction or negative direction along the vertical axis 331, respectively. The accordion panels 360A and 360B are advantageous because they protect electrical and mechanical and other types of components inside the column 102 (e.g., the pitch rotation mechanism 310, column telescoping mechanism 320, ring telescoping mechanisms 330A and 330B, and ring rotation mechanisms 340A and 340B) from becoming soiled or de-sterilized by fluid waste and other hazards. FIG. 3B shows an isometric view of the ring rotation mechanism 340A, while the ring rotation mechanism 340B is obscured by the column 102.

The surgical robotics system 100 rotates column rings 305A and 305B using the ring rotation mechanisms 340A and 340B, respectively. The ring telescoping rail 336 is coupled to the ring rotation motor 342 by a ring rotation bracket 344. The ring rotation motor 342 is coupled to a set of gears 346. The set of gears 346 includes a driving gear 346G. The driving gear 346G is engaged with a column ring rail 348 of the column ring 305A. Output rotation of the ring rotation motor 342 causes the set of gears 346 and the driving gear 346G to rotate. Accordingly, the rotation of the driving gear 346G causes the column ring 305A to rotate about a vertical axis 341 concentric to the column 102. The column 102 includes another ring rotation mechanism 340B corresponding to the column ring 305B. Generally, both ring rotation mechanisms 340A and 340B and column rings 305A and 305B will be substantially the same, however in other implementations they may be constructed using different mechanisms.

Figure 3C:
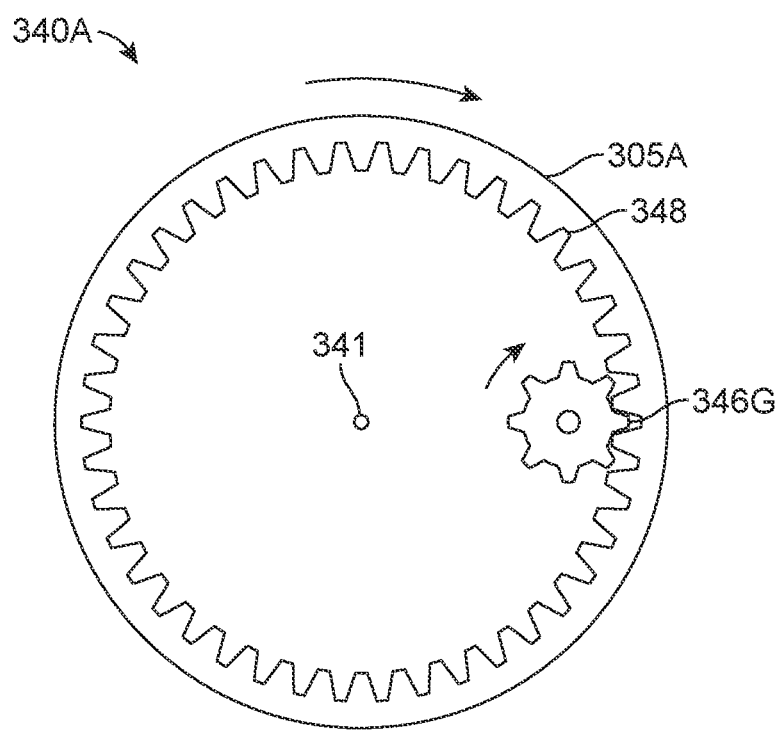
FIG. 3C is a top view of the column according to one embodiment.

FIG. 3C is a top view of the ring rotation mechanism 340A according to one embodiment. For purposes of clarity, FIG. 3C only shows the driving gear 346G, the column ring 305A, and the column ring rail 348 of the ring rotation mechanism 340A. In an example use case, the surgical robotics system 100 rotates the driving gear 346G clockwise to rotate the column ring rail 348—and thus, the column ring 305A—clockwise about the vertical axis 341.

Alternative views and embodiments of the column 103 including the above mentioned components are further illustrated and described at least in U.S. Provisional Application No. 62/162,486 filed May 15, 2015 and U.S. Provisional Application No. 62/162,467 filed May 15, 2015.

IV. Column-Mounted Robotic Arms

Figure 4A:
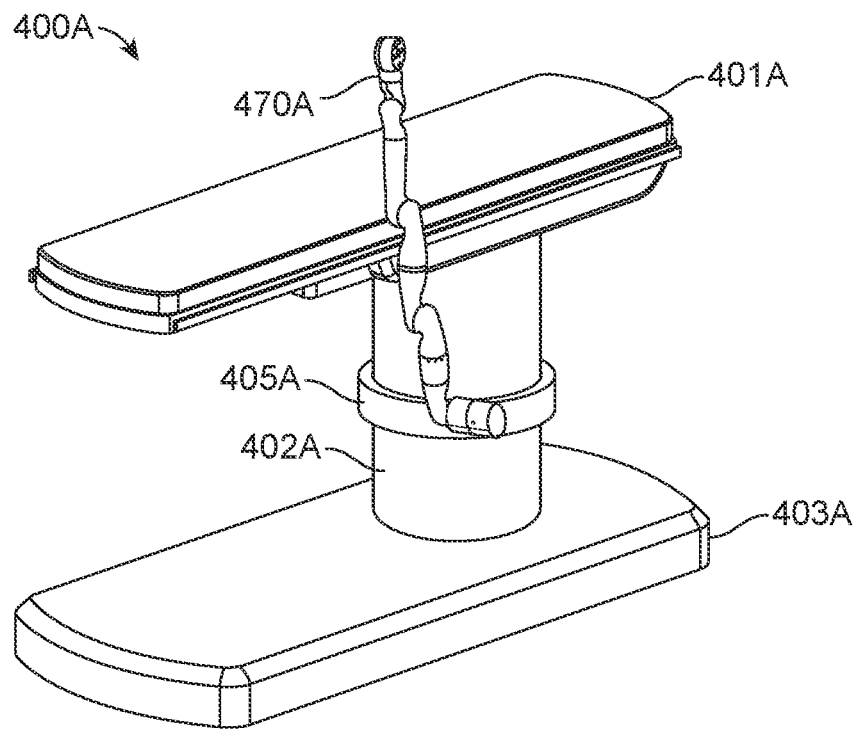
FIG. 4A is an isometric view of a surgical robotics system with a column-mounted robotic arm according to one embodiment.

FIG. 4A is an isometric view of a surgical robotics system 400A with a column-mounted robotic arm 470A according to one embodiment. The surgical robotics system 400A includes a set of robotic arms, a set of column rings, table 401A, column 402A, and base 403A. The surgical robotics system 400A is an embodiment of the surgical robotics system 100 shown in FIG. 1. Generally, the set of robotics arms includes one or more robotic arms, such as robotic arm 470A, where the robotic arms are coupled to one or more column rings, such as column ring 405A. Column rings are described in more detail with respect to FIGS. 5A-E in Section V. Column Ring below. Robotic arms are described in more detail with respect to FIGS. 6A-C in Section VI. Robotic Arm below. Column rings 405A are movably coupled to the column 402A. Thus, a robotic arm 470A attached to a column 405A may be referred to as a column-mounted robotic arm 470A. As introduced above, the surgical robotics system 400A uses robotic arms 470A to perform surgical procedures on a patient lying on the table 401A.

Figure 4B:
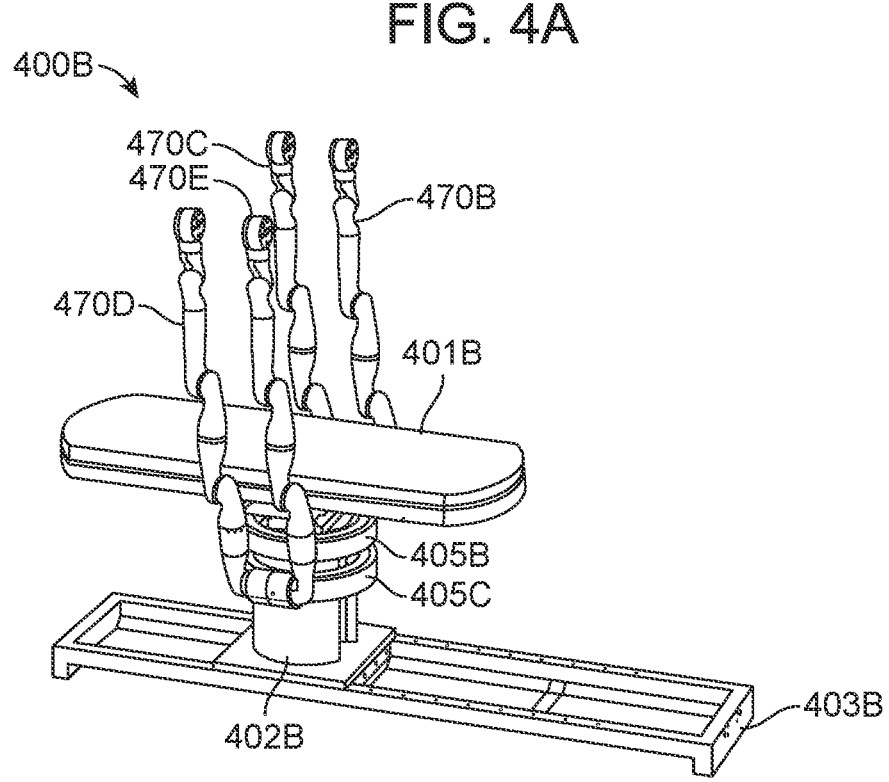
FIG. 4B is an isometric view of a surgical robotics system with column-mounted robotic arms according to one embodiment.

FIG. 4B is an isometric view of a surgical robotics system 400B with column-mounted robotic arms according to one embodiment. The surgical robotics system 400B is an embodiment of the surgical robotics system 400A shown in FIG. 4A. The surgical robotics system 400B includes multiple robotic arms, i.e., a first robotic arm 470B, second robotic arm 470C, third robotic arm 470D, and fourth robotic arm 470E, as well as multiple column rings, i.e., a first column ring 405B and second column ring 405C. In other embodiments, the surgical robotics system 400B may include additional or fewer robotic arms and/or column rings. Further, the robotic arms may be coupled to column rings in various configurations. For example, three robotic arms may be coupled to a column ring. Additionally, the surgical robotics system 400B may include three column rings each coupled to two robotic arms.

Alternative views and embodiments of the surgical robotics system 400B including the above mentioned components with column-mounted robotic arms are further illustrated and described at least in U.S. Provisional Application No. 62/162,486 filed May 15, 2015 and U.S. Provisional Application No. 62/162,467 filed May 15, 2015.

V. Column Ring

Figure 5A:
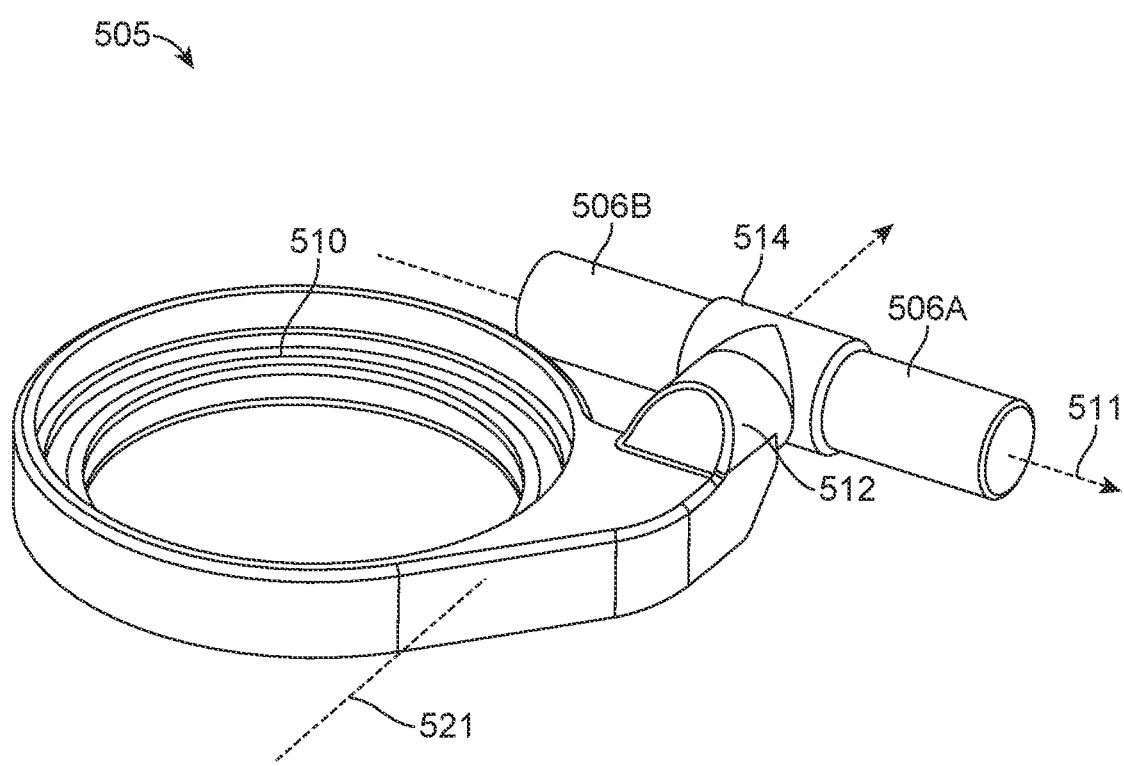
FIG. 5A is an isometric view of a column ring of the surgical robotics system according to one embodiment.

FIG. 5A is an isometric view of a column ring 505 of a surgical robotics system—for example, surgical robotics system 100, 400A, or 400B—according to one embodiment.

The column ring 505 includes a column ring rail 510, arm mount pivot 512, arm mount base 514, and a set of arm mounts. The set of arm mounts includes one or more arm mounts. Specifically, the set of arm mounts in FIG. 5A includes a first arm mount 506A and a second arm mount 506B. Generally, each arm mount of the set of arm mounts and the arm mount base 514 are cylindrically shaped.

The first arm mount 506A and the second arm mount 506B are movably coupled the arm mount base 514. The first arm mount 506A and the second arm 506B mount may rotate—together or independently—about the axis 511 concentric to the arm mount base 514. For example, the surgical robotics system 400B rotates the first arm mount 506A and the second arm mount 506B using a motor or other means of actuation (not shown) inside the arm mount base 514 or arm mounts. In some embodiments, the first arm mount 506A and the second arm mount 506B rotate at predetermined increments, e.g., increments of 15 degrees.

The arm mount base 514 is coupled to the arm mount pivot 512. The arm mount pivot 512 uses a motor or other means of actuation (not shown) inside the arm mount pivot 512 to rotate the arm mount base 514 about the axis 521 orthogonal to the axis 511. The arm mount pivot 512 is coupled to, and stationary relative to, the column ring rail 510. Rotating the arm mount base 514 is advantageous because robotic arms (and arm mounts) coupled to the arm mount base 514 may be reoriented in response to rotation of the table 401B. Accordingly, robotic arms coupled to the arm mounts of the arm mount base 514 have greater access to a patient lying on the table 401B.

Figure 5B:
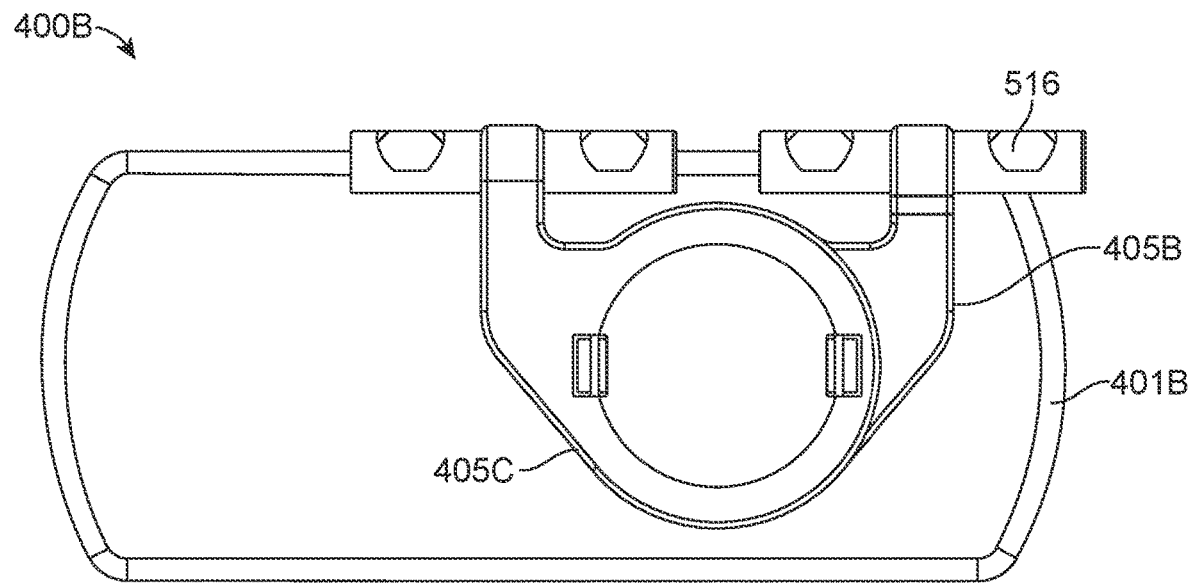
FIG. 5B is a bottom view of a set of column rings underneath a table according to one embodiment.

FIG. 5B is a bottom view of the set of column rings underneath the table 401B of FIG. 4B according to one embodiment. The set of column rings includes the first column ring 405B and the second column ring 405C. Note that FIG. 5B shows the first column ring 405B and the second column ring 405C aligned such that the arm mounts are on the same side of the table 401B, while FIG. 4B shows the first column ring 405B and the second column ring 405C positioned such that the arm mounts are on opposite sides of the table 401B. The surgical robotics system 400B may rotate the column rings 405B and 405C to position the arm mounts in other configurations. For example, two arm mounts are positioned on one side of the table 401B and two arm mounts are positioned on an opposite side of the table 401B. By rotating column rings independently from each other around the column, the surgical robotics system 400B may configure the arm mounts—and thus, robotic arms mounted to the arm mounts—in a greater number of possible positions. Due to this configurability, the surgical robotics system 400B accommodates a variety of surgical procedures because the robotic arms can access any area (e.g., upper body, core body, or lower body) of the body of a patient lying on the table 401B. In some embodiments, each arm mount of the column rings include a notch 516 which facilitates the attachment of a robotic arm to the arm mount.

Figure 5C:
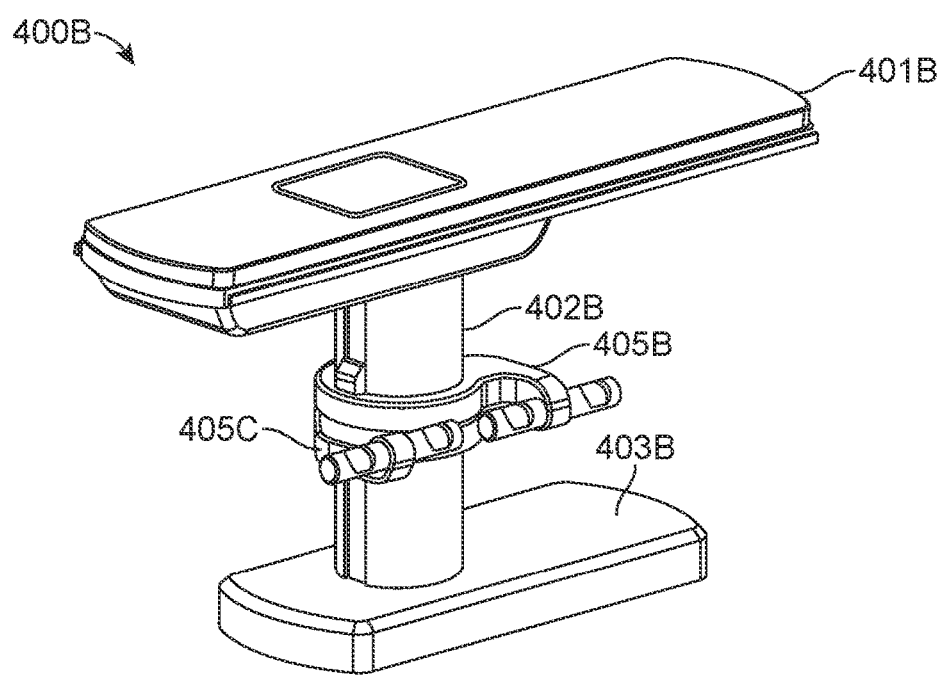
FIG. 5C is an isometric view of the set of column rings mounted to a column according to one embodiment.

FIG. 5C is an isometric view of the set of column rings mounted to the column 402B of FIG. 4B according to one embodiment. Similarly to FIG. 5B, FIG. 5C shows all the arm mounts aligned on the same side of the surgical robotics system 400B.

Figure 5D:
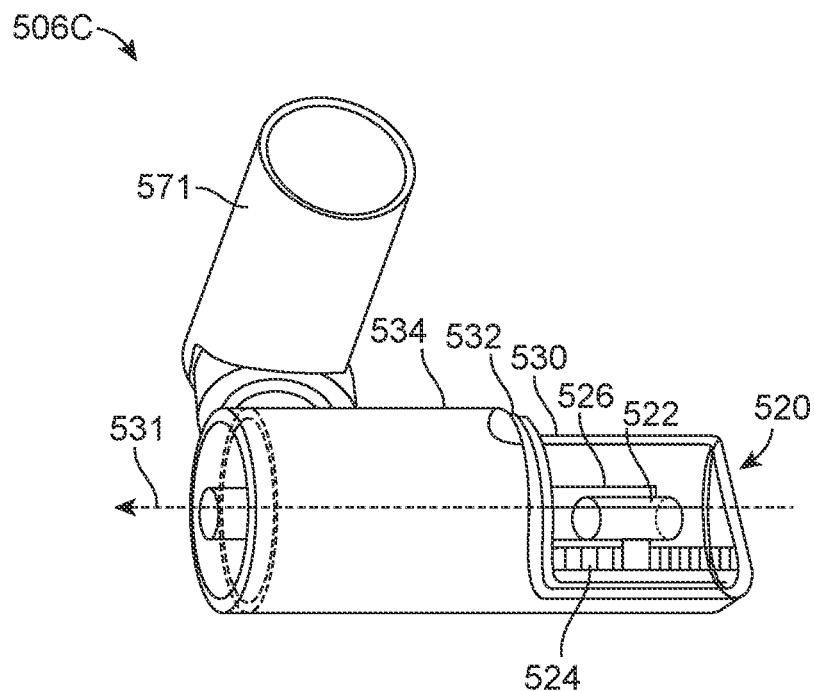
FIG. 5D is an isometric cutaway view of an arm mount of a column ring according to one embodiment.

FIG. 5D is an isometric cutaway view of an arm mount 506C of a column ring according to one embodiment. The arm mount 506C includes an arm mount telescoping mechanism 520 and a set of arm mount segments. The arm mount telescoping mechanism 520 includes an arm mount telescoping motor 522, arm mount telescoping lead screw 524, and arm mount telescoping rail 526. Generally, the set of arm mount segments includes one or more arm mount segments. Specifically, the set of arm mount segments in FIG. 5D includes a lower arm mount segment 530, middle arm mount segment 532, and upper arm mount segment 534. A robotic arm segment 571 (e.g., of the robotic arm 470B in FIG. 4B) is coupled to the upper arm mount segment 534. The middle arm mount segment 532 and the upper arm mount segment 534 are movably coupled to the lower arm mount segment 530. The lower arm mount segment 530 is coupled to an arm mount base (e.g., arm mount base 514 in FIG. 5A).

The surgical robotics system 400B translates the arm mount 506C along an axis 531 using the arm mount telescoping mechanism 520. In FIG. 5D, the axis 531 is in a horizontal orientation, though it should be noted that, in other embodiments, the axis 531 is in a vertical or any other orientation. The arm mount telescoping motor 522 is coupled to the arm mount telescoping rail 526. The arm mount telescoping rail 526 is engaged with the arm mount telescoping lead screw 524. The arm mount telescoping lead screw 524 is stationary relative to the lower arm mount segment 530. Output rotation of the arm mount telescoping motor 522 causes the arm mount telescoping rail 526 to translate along the vertical axis 531. Translation of the arm mount 506C is advantageous because, if the arm mount 506C is extended, a robotic arm mounted to the arm mount 506C may have greater access to a patient lying on the table 401B during a surgical procedure.

Figure 5E:
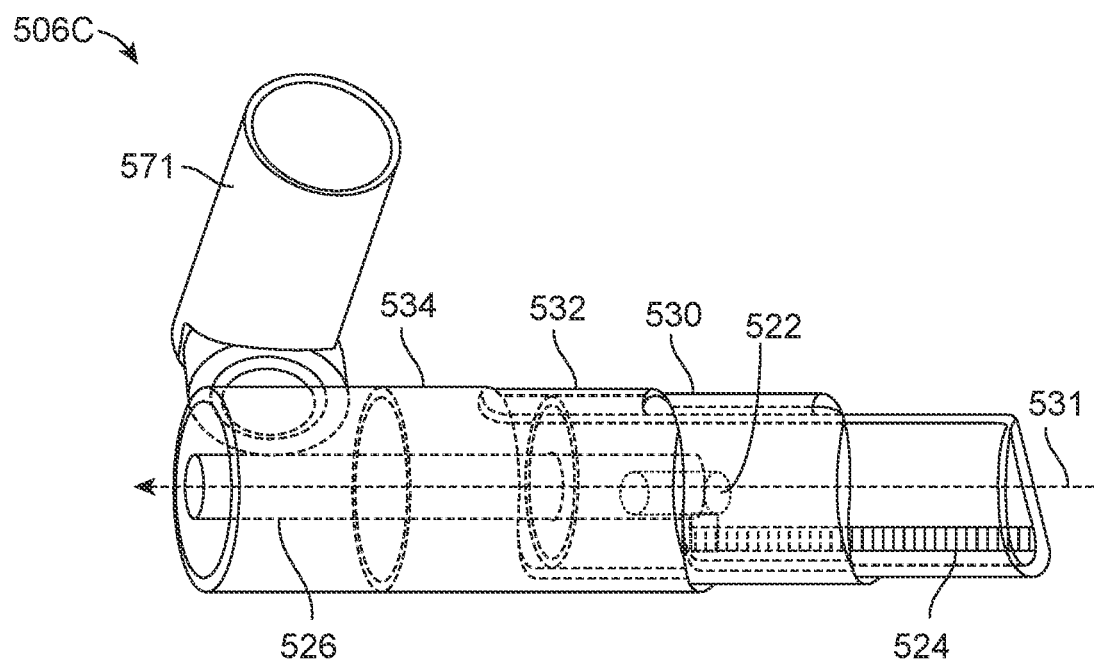
FIG. 5E is an isometric cutaway view of the arm mount in a telescoped configuration according to one embodiment.

FIG. 5E is an isometric cutaway view of the arm mount 506C in a telescoped configuration according to one embodiment. In the telescoped configuration, the upper arm mount segment 534 and the middle arm mount segment 532 extend in the positive axis 531 direction to facilitate extension of the arm mount 506C.

Alternative views and embodiments of the column ring 505 including the above mentioned components are further illustrated and described at least in U.S. Provisional Application No. 62/162,486 filed May 15, 2015 and U.S. Provisional Application No. 62/162,467 filed May 15, 2015.

VI. Robotic Arm

Figure 6A:
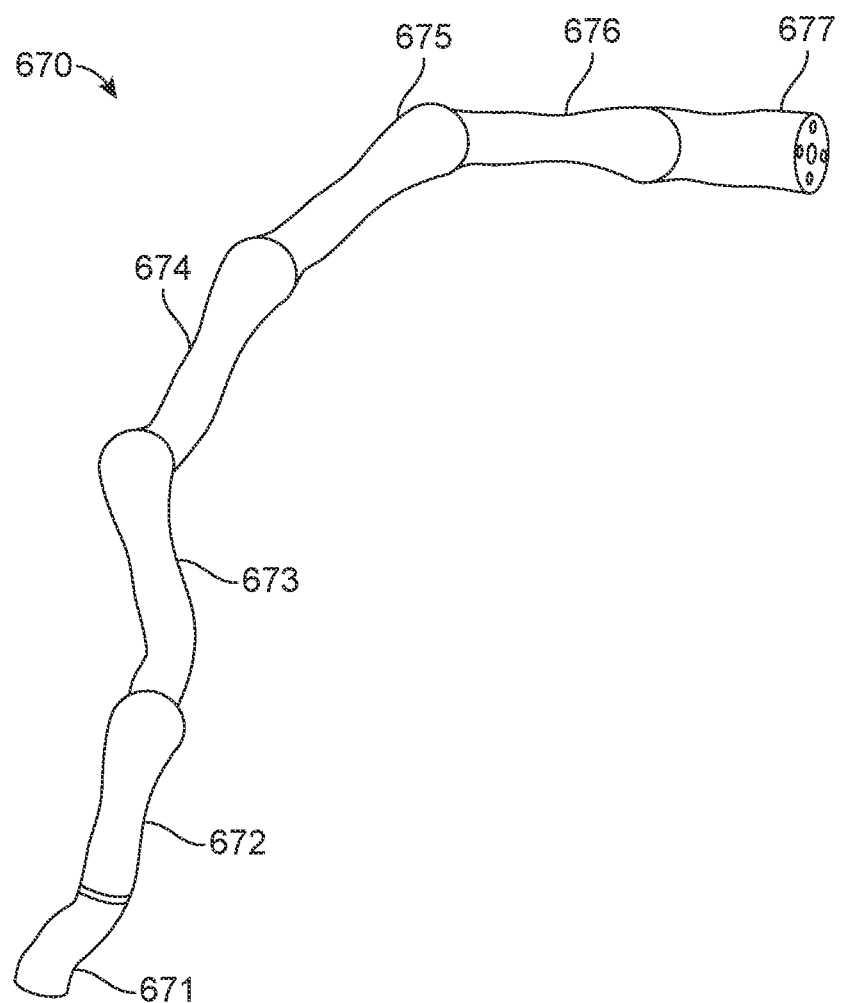
FIG. 6A is an isometric view of a robotic arm of the surgical robotics system according to one embodiment.

FIG. 6A is an isometric view of a robotic arm 670 of a surgical robotics system—for example, surgical robotics system 100, 400A, or 400B—according to one embodiment. Generally, the robotic arm 670 includes a set of robotic arm segments such as robotic arm segments 671, 672, 673, 674, 675, 676, and 677. Each arm segment is movably coupled to at least one other arm segment at an arm segment joint. In particular, the first arm segment 671 is movably coupled to the second arm segment 672, the second arm segment 672 is movably coupled to the third arm segment 673, and so forth. The first arm segment 671 is movably coupled to an arm mount (e.g., arm mount 506A in FIG. 5A). The seventh arm segment 677 (or the last arm segment of a set of arm segments including a number of arm segments different than seven), is coupled to a surgical instrument. The seventh arm segment 677 may also include mechanisms to hold a surgical instrument such as a clamp or robotic fingers. The robotic arm 670 uses electrical and mechanical components, such as motors, gears, and sensors, inside the robotic arm segments to rotate the arm segments at the arm segment joints.

The robotic arm 670 receives control signals from a robotic arm control system, for example, housed in the column 402B in FIG. 4B. In some embodiments, the robotic arm 670 receives control signals from a robotic arm control system located outside of the column 402B or separate from the surgical robotics system 400B. Generally, the robotic arm 670 may include sensors that provide sensor data to the robotic arm control system. Specifically, pressure sensors provide force feedback signals and encoders or potentiometers provide measurements of rotation of arm segments. The robotic arm control system uses the sensor data to generate the control signals provided to the robotic arm 670. Since each arm segment may rotate with respect to another adjacent segment, each arm segment provides an additional degree of freedom to the mechanical system of the robotic arm 670. By rotating the robotic arm segments, the surgical robotics system 400B positions a surgical instrument coupled to the robotic arm 670 such that the surgical instrument has access to a patient undergoing a surgical procedure. Configurations of robotic arms of the surgical robotics system 400B are further described with reference to FIGS. 7A-F in Section VII. System Orientations for Performing Surgical Procedures.

Figure 6B:
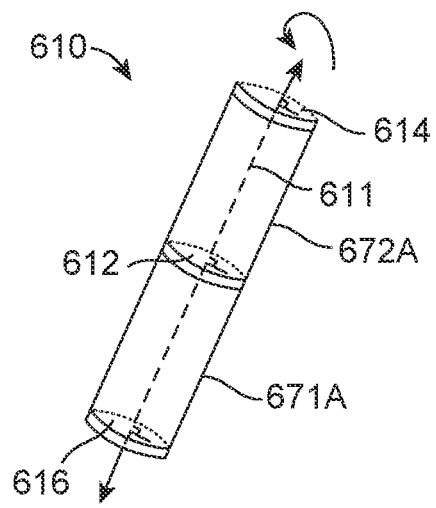
FIG. 6B is an isometric view of an arm segment joint of the robotic arm according to one embodiment.

FIG. 6B is an isometric view of an arm segment joint 610 of the robotic arm 670 according to one embodiment. The first arm segment 671A and the second arm segment 672A are embodiments of any of the arm segments in FIG. 6A. The arm segments 671A and 672A are cylindrically shaped and joined at the plane 612. The first arm segment 671A rotates relative to the second arm segment 672A about an axis 611 perpendicular to the plane 612. Further, the axis 611 is perpendicular to the plane 614 of the second arm segment 672A and perpendicular to the plane 616 of the first arm segment 671A. That is, the axis 611 is longitudinal relative to the arm segments 671A and 672A.

Figure 6C:
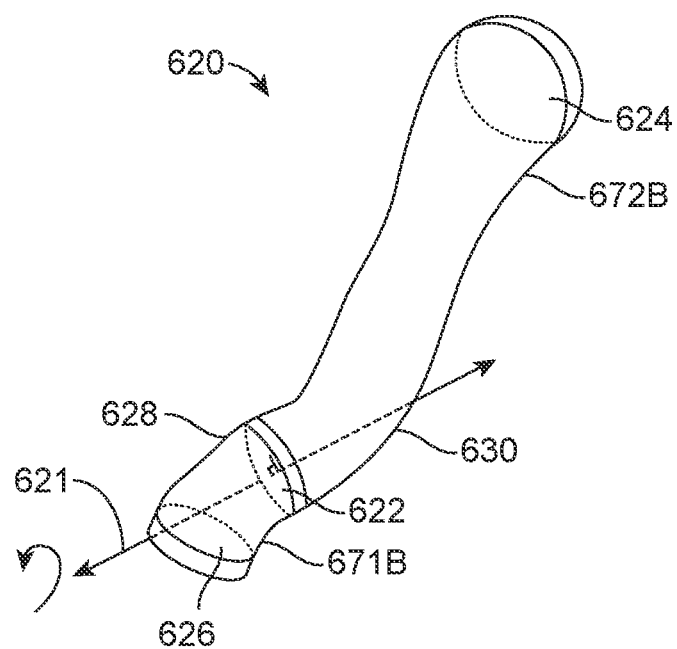
FIG. 6C is an isometric view of another arm segment joint of the robotic arm according to one embodiment.

FIG. 6C is an isometric view of another arm segment joint 620 of the robotic arm 670 according to one embodiment. The arm segments 671B and 672B are joined at the plane 622. Unlike the cylindrically shaped arm segments shown in FIG. 6B, the arm segments 671B and 672B each include a curved section 628 and 630, respectively. The first arm segment 671B rotates relative to the second arm segment 672B about an axis 621 perpendicular to the plane 622. The axis 621 is not perpendicular to the plane 624 of the arm segment 672B and not perpendicular to the plane 626 of the arm segment 671B. In some embodiments, the axis of rotation is perpendicular to a plane of one arm segment, but not perpendicular to a plane of the other arm segment of an arm segment joint.

Alternative views and embodiments of the robotic arm 670 including the above mentioned components are further illustrated and described at least in U.S. Provisional Application No. 62/162,486 filed May 15, 2015 and U.S. Provisional Application No. 62/162,467 filed May 15, 2015.

VII. System Orientations for Performing Surgical Procedures

The surgical robotics system 400B in FIG. 4B performs a variety of surgical procedures using column-mounted robotic arms of the set of robotic arms. The surgical robotics system 400B configures the column-mounted robotic arms to access portions of a patient lying on the table 401B before, during, and/or after a surgical procedure. The column-mounted robotic arms access portions near the groin of the patient for surgical procedures such as ureteroscopy, percutaneous nephrolithotomy (PCNL), colonoscopy, and fluoroscopy. The column-mounted robotic arms to access portions near the core (e.g., abdomen) area the patient for surgical procedures such as prostatectomy, colectomy, cholecystectomy, and inguinal hernia. The column-mounted robotic arms to access portions near the head of the patient for surgical procedures such as bronchoscopy, endoscopic retrograde cholangiopancreatography (ERCP).

The surgical robotics system 400B automatically reconfigures the column-mounted robotic arms, column rings, column, and table to perform different surgical procedures. The features of each subsystem and component of the surgical robotics system 400B enable the same set of robotics arms to access a large working volume, and multiple working volumes (based on the configuration), to perform a variety of surgical procedures on the patient. In particular, as mentioned above, the robotic arms may be configured in a first configuration to access the patients' groin area, in a second configuration to access the patients' abdomen area, and in a third configuration to access the patients' head area, in addition to other possible configurations. The degrees of freedom provided by the arm segments of the robotic arms, column rings, column, and table contribute to the wide range of configurations. The surgical robotics system 400B includes a computer system that stores computer program instructions, for example within a non-transitory computer-readable storage medium such as a persistent magnetic storage drive, solid state drive, etc. When executed by a processor of the computer system, the instructions cause the components of the surgical robotics system 400B to automatically reconfigure without the need for intervention, or with minimal intervention, from a user, e.g., a physician. For example, based on the instructions, the computer system sends an electronic control signal to motors of the robotics arms. In response to receiving the control signal, the motors rotate arm segments of the robotics arms into a certain position. The physician or another user may design a configuration of the surgical robotics system by creating the instructions and providing the instructions to the computer system. For example, the instructions are uploaded to a database of the computer system. The automatic configurability of the surgical robotics system 400B is an advantage because the automatic configurability saves resources. Specifically, the surgical robotics system 400B reduces the amount of time taken by users to setup the surgical robotics system 400B for a surgical procedure. Further, by using the surgical robotics system 400B for a variety of surgical procedures, users reduce the amount of surgical equipment that they need to purchase, maintain, store, and learn to operate.

Alternative views and embodiments of use cases of the surgical robotics system 400B with column-mounted robotic arms including the above mentioned components are further illustrated and described at least in U.S. Provisional Application No. 62/162,486 filed May 15, 2015 and U.S. Provisional Application No. 62/162,467 filed May 15, 2015.

VII. A. Lower Body Surgery

Figure 7A:
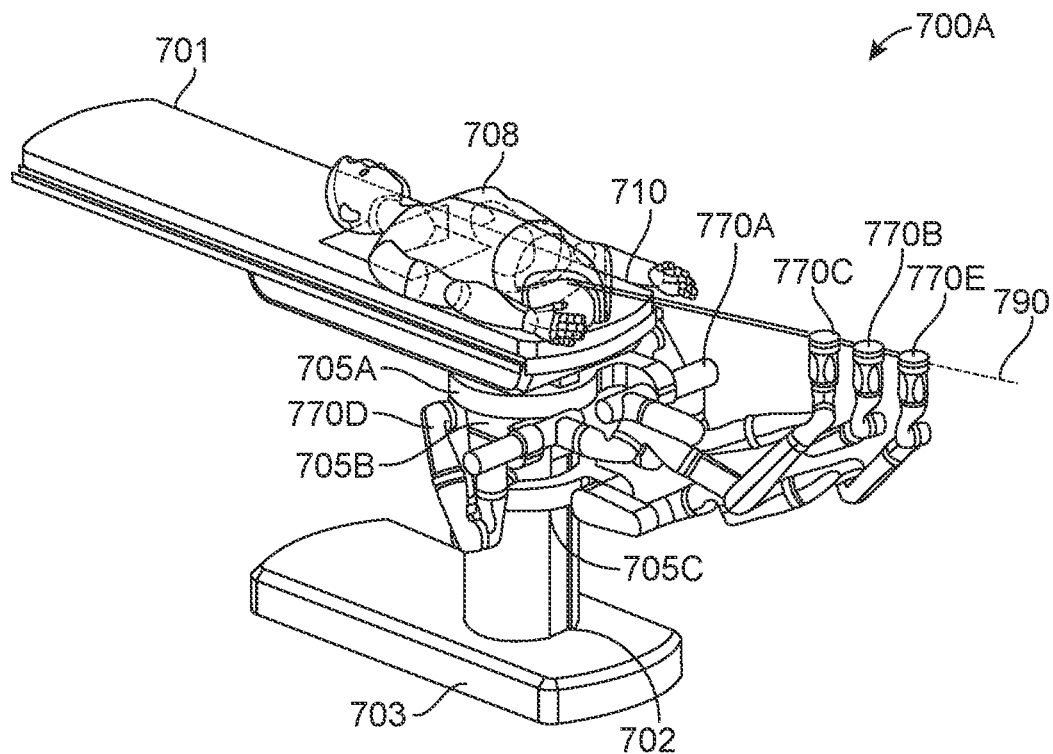
FIG. 7A is an isometric view of a surgical robotics system with column-mounted arms configured to access the lower body area of a patient according to one embodiment.

FIG. 7A is an isometric view of a surgical robotics system 700A with column-mounted arms configured to access the lower body area of a patient 708 according to one embodiment. The surgical robotics system 700A is an embodiment of—though includes more components than—the surgical robotics system 400B in FIG. 4B. Specifically, the surgical robotics system 700A includes a set of robotic arms (including five robotic arms in total) and a set of three column rings. A first robotic arm 770A and a second robotic arm 770B are coupled to a first column ring 705A. A third robotic arm 770C and a fourth robotic arm 770D are coupled to a second column ring 705B. A fifth robotic arm 770E is coupled to a third column ring 705C. FIG. 7A shows a wireframe of the patient 708 lying on the table 701 undergoing a surgical procedure, e.g., ureteroscopy, requiring access to the lower body area of the patient 708. Legs of the patient 708 are not shown as to not obscure portions of the surgical robotics system 700A.

The surgical robotics system 700A configures the set of robotic arms to perform a surgical procedure on the lower body area of the patient 708. Specifically, the surgical robotics system 700A configures the set of robotic arms to manipulate a surgical instrument 710. FIG. 7A shows the set of robotic arms inserting the surgical instrument 710 along a virtual rail 790 into the groin area of the patient 708. Generally, a virtual rail 790 is a co-axial trajectory along which the set of robotic arms translates a surgical instrument (typically a telescoping instrument). The second robotic arm 770B, the third robotic arm 770C, and the fifth robotic arm 770E are coupled, e.g., holding, the surgical instrument 710. The first robotic arm 770A and the fourth robotic arm 770D are stowed to the sides of the surgical robotics system because they are not necessarily required to for the surgical procedure—or at least part of the surgical procedure—shown in FIG. 7A. The robotic arms are configured such that they manipulate the surgical instrument 710 from a distance away from the patient 708. This is advantageous, for example, because there is often limited space available closer toward the patient's body or there is a sterile boundary around the patient 708. Further, there may also be a sterile drape around surgical equipment. During a surgical procedure, only sterile objects are allowed pass the sterile boundary. Thus, the surgical robotics system 700A may still use robotic arms that are positioned outside of the sterile boundary and that are covered with sterilized drapes to perform a surgical procedure.

In one embodiment, the surgical robotics system 700A configures the set of robotic arms to perform an endoscopy surgical procedure on the patient 708. The set of robotic arms hold an endoscope, e.g., the surgical instrument 710. The set of robotic arms insert the endoscope into the patient's body via an opening in the groin area of the patient 708. The endoscope is a flexible, slender, and tubular instrument with optical components such as a camera and optical cable. The optical components collect data representing images of portions inside the patient's body. A user of the surgical robotics system 700A uses the data to assist with performing the endoscopy.

Figure 7B:
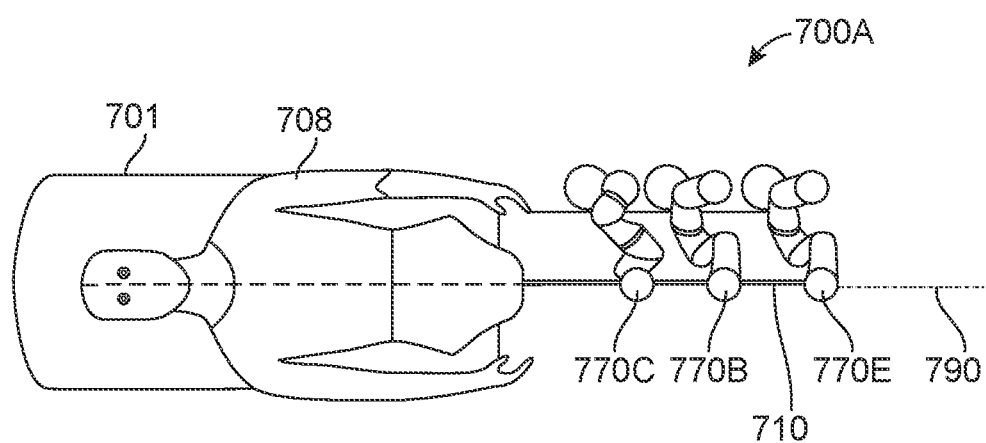
FIG. 7B is a top view of the surgical robotics system with column-mounted arms configured to access the lower body area of the patient according to one embodiment.

FIG. 7B is a top view of the surgical robotics system 700A with column-mounted arms configured to access the lower body area of the patient 708 according to one embodiment.

Figure 7C:
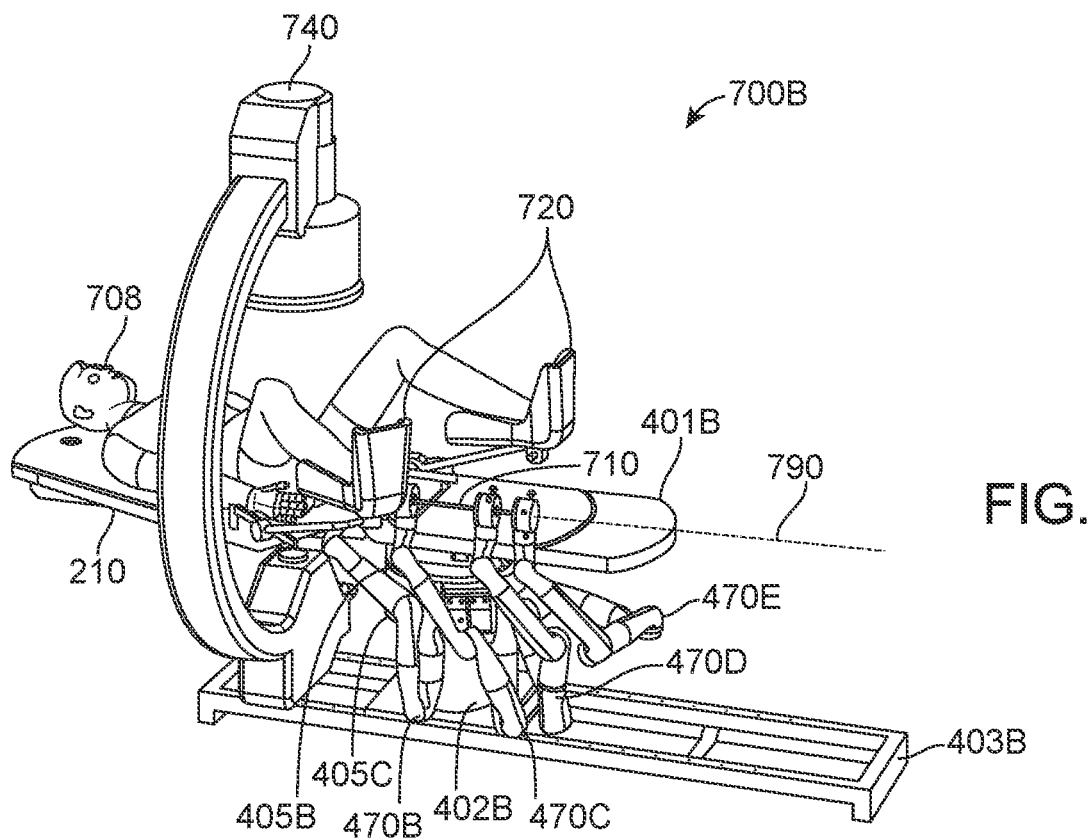
FIG. 7C is an isometric view of an imaging device and a surgical robotics system with column-mounted arms configured to access the lower body area of a patient according to one embodiment.

FIG. 7C is an isometric view of an imaging device 740 and a surgical robotics system 700B with column-mounted arms configured to access the lower body area of a patient 708 according to one embodiment. The surgical robotics system 700B is an embodiment of the surgical robotics system 400B in FIG. 4B. The surgical robotics system 700B includes a pair of stirrups 720 that support the legs of the patient 708, and thus exposing the groin area of the patient 708. Generally, the imaging device 740 captures images of body parts or other objects inside a patient 708. The imaging device 740 may be a C-arm, also referred to as a mobile C-arm, which is often used for fluoroscopy type surgical procedures, or another type of imaging device. A C-arm includes a generator, detector, and imaging system (not shown). The generator is coupled to the bottom end of the C-arm and faces upward toward the patient 708. The detector is coupled to the top end of the C-arm and faces downward toward the patient 708. The generator emits X-ray waves toward the patient 708. The X-ray waves penetrate the patient 708 and are received by the detector. Based on the received X-ray waves, the imaging system 740 generates the images of body parts or other objects inside the patient 708. The swivel segment 210 of the table 401B is rotated laterally such that the groin area of the patient 708 is aligned in between the generator and detector of the C-arm imaging device 740. The C-arm is a physically large device with a footprint that needs to be stationed underneath the patient. In particular, the generator of the C-arm needs to be underneath the operative area of the patient, e.g., the abdomen area. In typical surgical beds mounted to a column, the column interferes with the positioning of the C-arm generator, e.g., because the column is also underneath the operative area. In contrast, due to the configurability of the swivel segment 210, the surgical robotics system 700B may configure the table 401B such that the C-arm, the robotic arms, and a user (e.g., physician) have a sufficient range of access to perform a surgical procedure on a working area the patient's body. In one example use case, the table 401B is translated laterally along a longitudinal axis of the table 401B such that the robotic arms can access the groin or lower abdomen area of a patient on the table 401B. In another example use case, by rotating the swivel segment 210 away from the column 402B, the generator of the C-arm 740 may be positioned underneath the groin area of the patient 708. The swivel segment 210— with a patient lying on the swivel segment 210—may be rotated at least to 45 degrees relative to a longitudinal axis of the table 401B without tipping over the surgical robotics system. In particular, the surgical robotics system does not tip because the center of mass of the surgical robotics system (e.g., the center of mass of the combined, at least, table, bed, and base) is positioned above a footprint of the base. Outrigger casters, further described with reference to FIGS. 8G-J in Section VIII. Base, may provide further stability to prevent the surgical robotics system from tipping over when a swivel segment is rotated away from the table.

The surgical robotics system 700B uses a set of column-mounted robotic arms to manipulate a surgical instrument 710. Each of the robotic arms is coupled to, e.g., holding, the surgical instrument 710. The surgical robotics system 700B uses the robotic arms to insert the surgical instrument 710 into the groin area of the patient along a virtual rail 790.

Figure 7D:
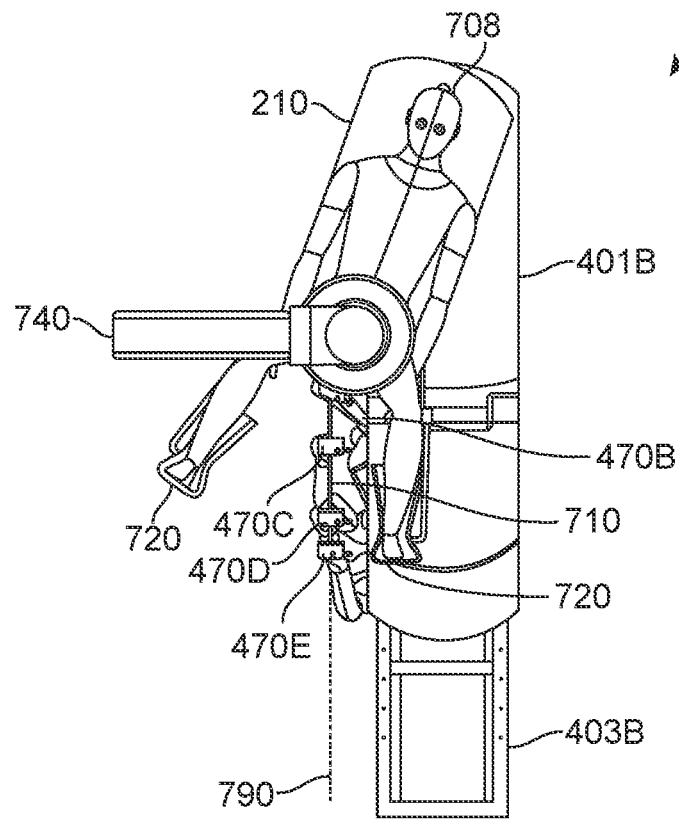
FIG. 7D is a top view of the imaging device and the surgical robotics system with column-mounted arms configured to access the lower body area of the patient according to one embodiment.

FIG. 7D is a top view of the imaging device 740 and the surgical robotics system 700B with column-mounted arms configured to access the lower body area of the patient 708 according to one embodiment.

VII. B. Core Body Surgery

Figure 7E:
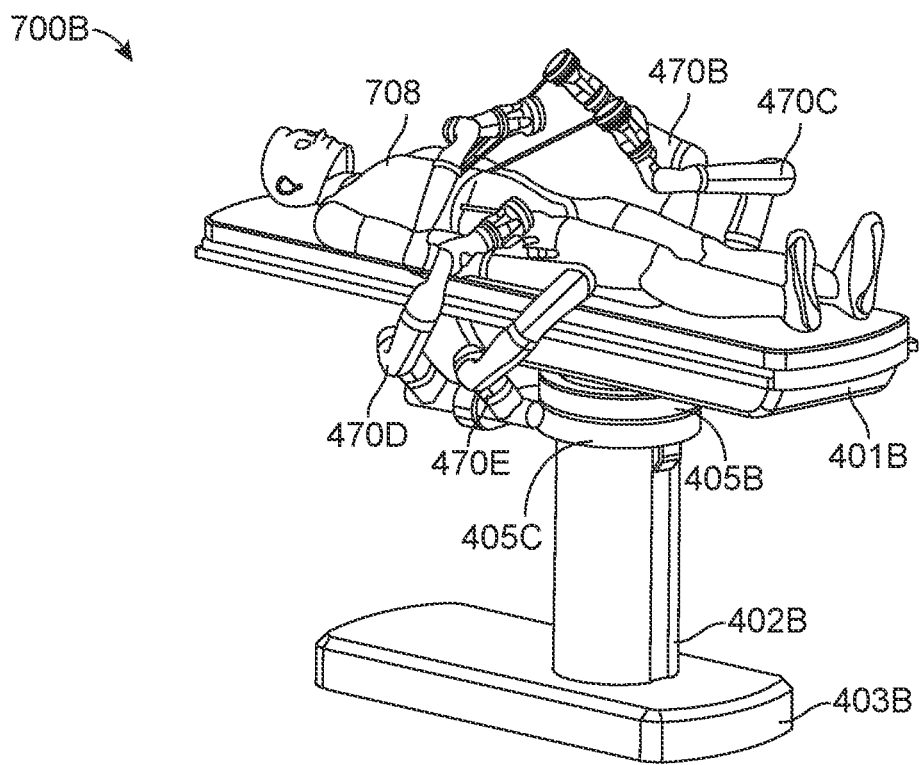
FIG. 7E is an isometric view of the surgical robotics system with column-mounted arms configured to access the core body area of a patient according to one embodiment.

FIG. 7E is an isometric view of the surgical robotics system 700B (or 400B) with column-mounted arms configured to access the core body area of a patient 708 according to one embodiment. The surgical robotics system 700B has been reconfigured from the configuration shown in FIG. 7C-D where the robotic arms access the lower body area of the patient 708. In embodiments where the table includes a swivel segment 210, the swivel segment 210 of the table is rotated in-line with the rest of the table. The patient 708 lying on the table 401B is undergoing a surgical procedure, e.g., prostatectomy or laparoscopy, requiring access to the core body area of the patient 708. Each robotic arm is manipulating a surgical instrument to perform the surgical procedure. The surgical robotics system 700B raises the column rings 405B and 405C toward the table 401B so that the robotic arms have greater access the patient 708. Further, the surgical robotics system 700B rotates the column rings such that two of the robotic arms extend from one side of the table 401B and the other two robotic arms extend from the opposite side of the 401B. Thus, the robotic arms are less likely to interfere with each other (e.g., a robotic arm blocking the motion of another robotic arm) during the surgical procedure.

VII. C. Upper Body Surgery

Figure 7F:
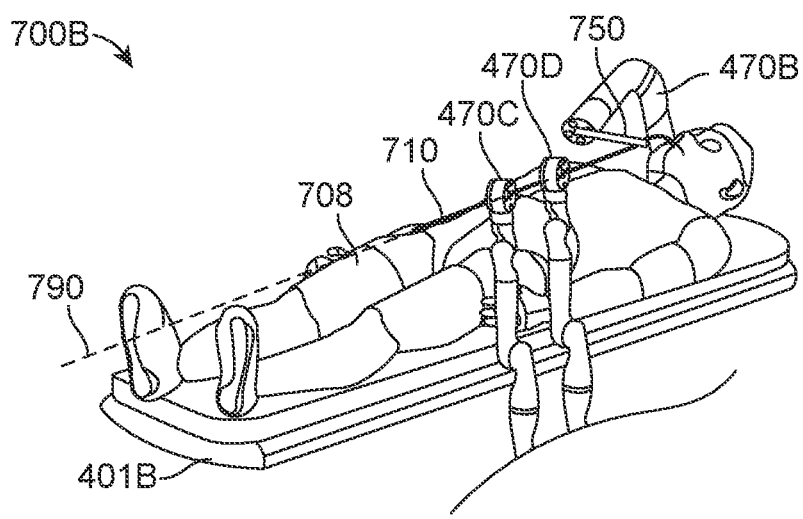
FIG. 7F is an isometric view of the surgical robotics system with column-mounted arms configured to access the upper body area of a patient according to one embodiment.

FIG. 7F is an isometric view of the surgical robotics system 700B (or 400B) with column-mounted arms configured to access the upper body area of a patient 708 according to one embodiment. The surgical robotics system 700B has been reconfigured from the configuration shown in FIG. 7E where the robotic arms access the core body area of the patient 708. In embodiments where the table includes a swivel segment 210, the swivel segment 210 of the table is rotated in-line with the rest of the table. The patient 708 lying on the table 401B is undergoing a surgical procedure, e.g., bronchoscopy, requiring access to the upper body area of the patient 708, specifically the head of the patient 708. The robotic arm 470C and the robotic arm 470D are inserting a surgical instrument 710D, e.g., a bronchoscope, into the mouth of the patient 708 along a virtual rail 790. The robotic arm 470B is coupled to, e.g., holding, an introducer 750. The introducer 750 is a surgical instrument that directs the bronchoscope into the mouth of the patient 708. Specifically, the trajectory of the bronchoscope along the virtual rail 790 begins parallel to the patient 708. The introducer 750 changes the angle of the virtual rail 790 just before the bronchoscope enters the mouth. The robotic arm 470E (not shown in FIG. 7F) is not used for the surgical procedure, and thus is stowed away.

VIII. Base

Figure 8A:
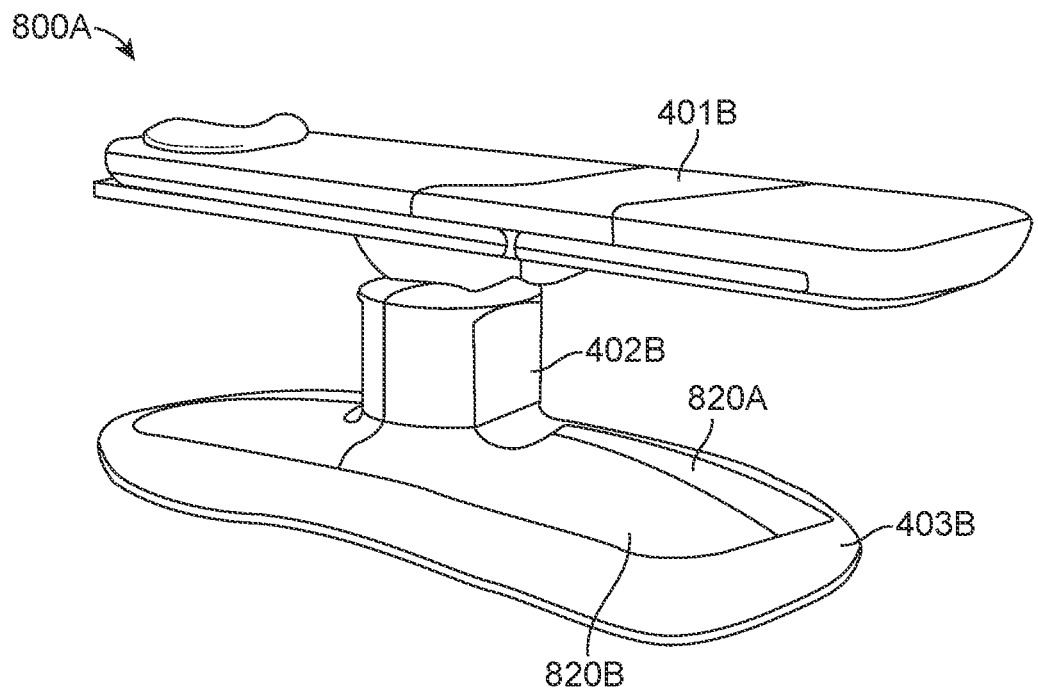
FIG. 8A is an isometric view of a base of a surgical robotics system according to one embodiment.

FIG. 8A is an isometric view of a base 403A of a surgical robotics system 800A according to one embodiment. The surgical robotics system 800A is an embodiment of the surgical robotics system 400B in FIG. 4B. The surgical robotics system 800A stores column-mounted robotic arms and/or column rings (not shown) inside the base 403B when the robotic arms are not in use. The base 403B includes a first panel 820A and a second panel 820B that cover stored robotic arms. The first panel 820A and the second panel 820B are advantageous because they prevent waste materials from de-sterilizing or otherwise contaminating stored robotic arms.

Figure 8B:
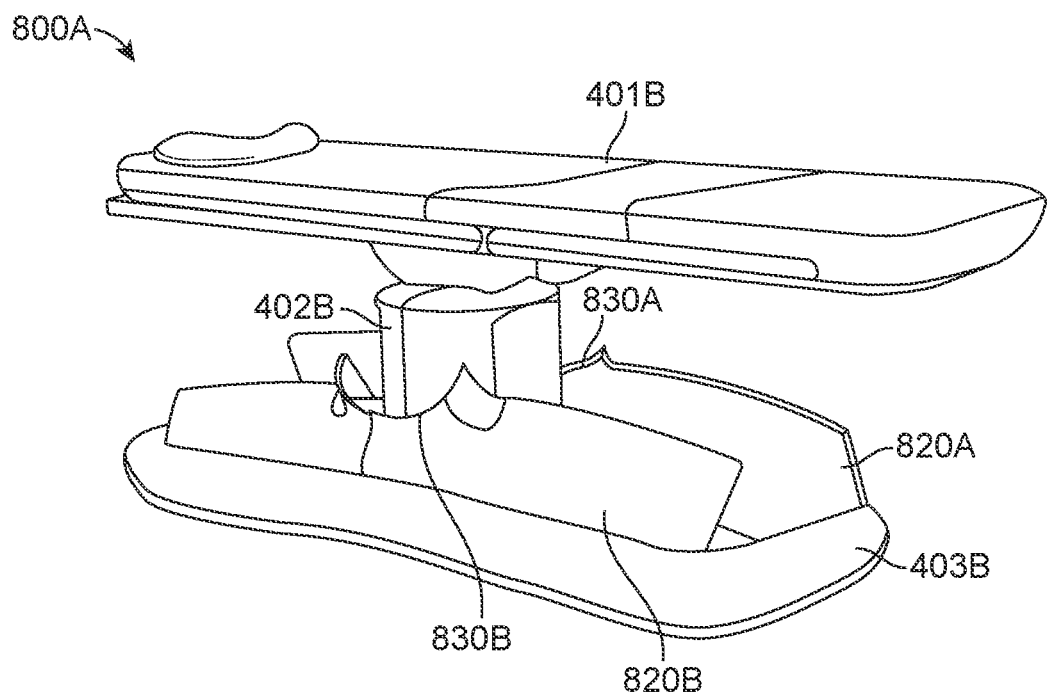
FIG. 8B is an isometric view of open panels of the base according to one embodiment.

FIG. 8B is an isometric view of open panels of the base 403B according to one embodiment. The first panel 820A and the second panel 820B pivot away from the column 802A such that column-mounted robotic arms have access to inside the base 403B. The first panel 820A includes a cutout 830A and the second panel 820B includes a cutout 830B. The cutouts 830A and 830B conform to the shape of the column 402B such that the panels 820A and 820B form a seal around the column 402B when closed. The surgical robotics system 800A may automatically open and close the first panel 820A and the second panel 820B using motors or other means of actuation. A user of the surgical robotics system 800A may also manually open and close the first panel 820A and the second panel 820B.

Figure 8C:
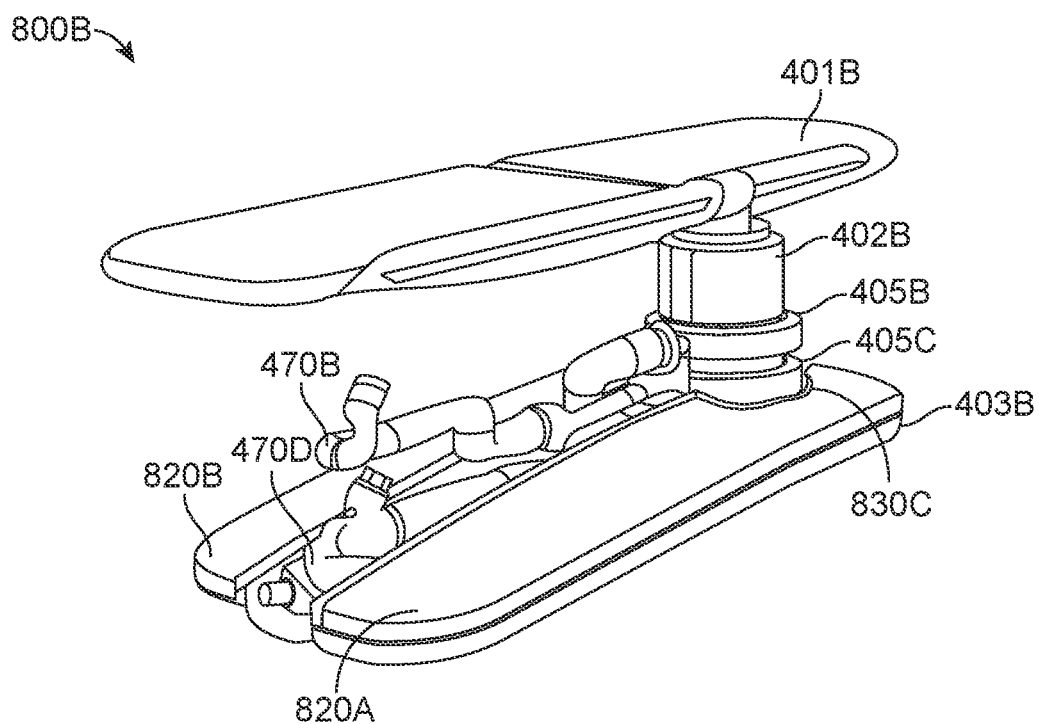
FIG. 8C is an isometric view of robotic arms stowed inside a base of a surgical robotics system according to one embodiment.

FIG. 8C is an isometric view of a robotic arm stowed inside a base 403B of a surgical robotics system 800B according to one embodiment. The surgical robotics system 800B is an embodiment of the surgical robotics system 400B in FIG. 4B. The surgical robotics system 800B stores column-mounted robotic arms 470B and 470D and column rings 405B and 405C inside the base 403B when the robotic arms are not in use. The base 403B includes a first panel 820A and a second panel 820B that cover stored robotic arms and column rings. The first panel 820A includes a cutout 830C. The second panel 820B also includes a cutout (not shown due to being obscured by other components). The cutouts conform to the shape of the column 402B such that the panels 820A and 820B form a seal around the column 402B when closed.

The first panel 820A and a second panel 820B translate laterally to provide access for the robotic arms and column rings into the base 403B. FIG. 8C shows the first panel 820A and a second panel 820B translated to form an opening. The opening may be large enough to provide access for a robotic arm, but not too large as to still provide protection to the robotic arms even when the panels are open. The robotic arm 470D and column ring 405C are stowed inside the base 403B. The robotic arm 470B and column ring 405B are outside the base 403B, though they may also be stowed inside the base 403B. The surgical robotics system 800B may automatically open and close the first panel 820A and the second panel 820B using motors or other means of actuation. A user of the surgical robotics system 800B may also manually open and close the first panel 820A and the second panel 820B.

Figure 8D:
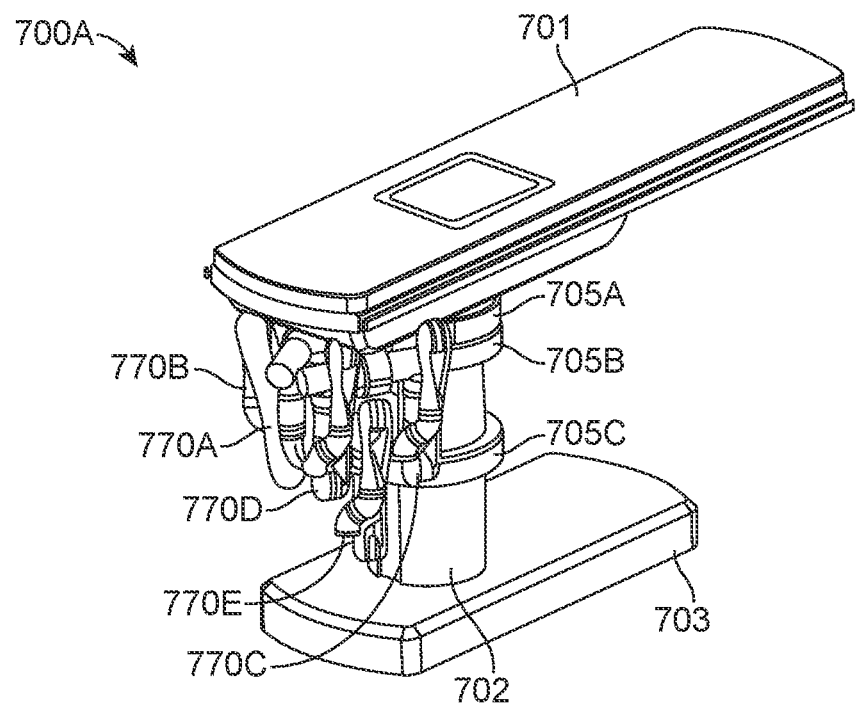
FIG. 8D is an isometric view of robotic arms stowed underneath a table of a surgical robotics system according to one embodiment.

FIG. 8D is an isometric view of robotic arms stowed underneath the table 701 of the surgical robotics system 700A according to one embodiment. Specifically, the arm segments of each robotic arm rotate such that the robotic arm is in a compact configuration for stowage. The surgical robotics system 700A raises the first column ring 705A and the second column ring 705B, and lowers the third column ring 705C toward the center of the column 702. This way, the robotic arms have enough space in the stowed configuration without interfering with each other. In one embodiment, the column 702 includes covers (e.g., similar to panels 820A and 820B) over the robotics arms to protect the robotic arms from contamination or damage.

Figure 8E:
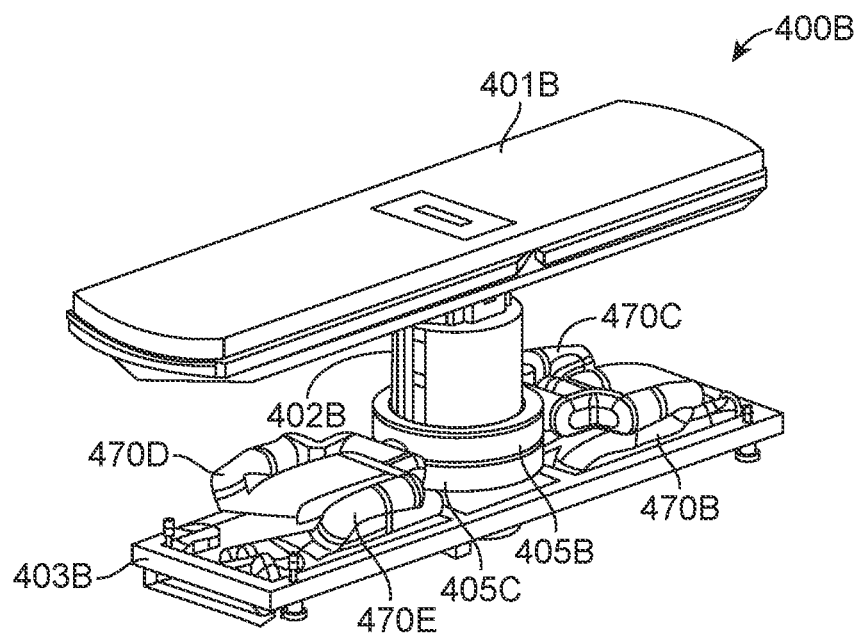
FIG. 8E is an isometric view of robotic arms stowed above a base of a surgical robotics system according to one embodiment.

FIG. 8E is an isometric view of robotic arms stowed above the base 403B of the surgical robotics system 400B according to one embodiment. The robotic arms 470B, 470C, 470D, and 470E are in a stowed configuration. Specifically, the arm segments of each robotic arm rotate such that the robotic arm is in a compact configuration for stowage. The surgical robotics system 400B lowers the first column ring 405B and the second column ring 405C along the column 402B such that the stowed robotic arms rest on the base 403B and are away from the table 401B. A cover (not shown) such as a drape or panel may be used to cover the stowed robotic arms for protection from de-sterilization or other contamination.

Figure 8F:
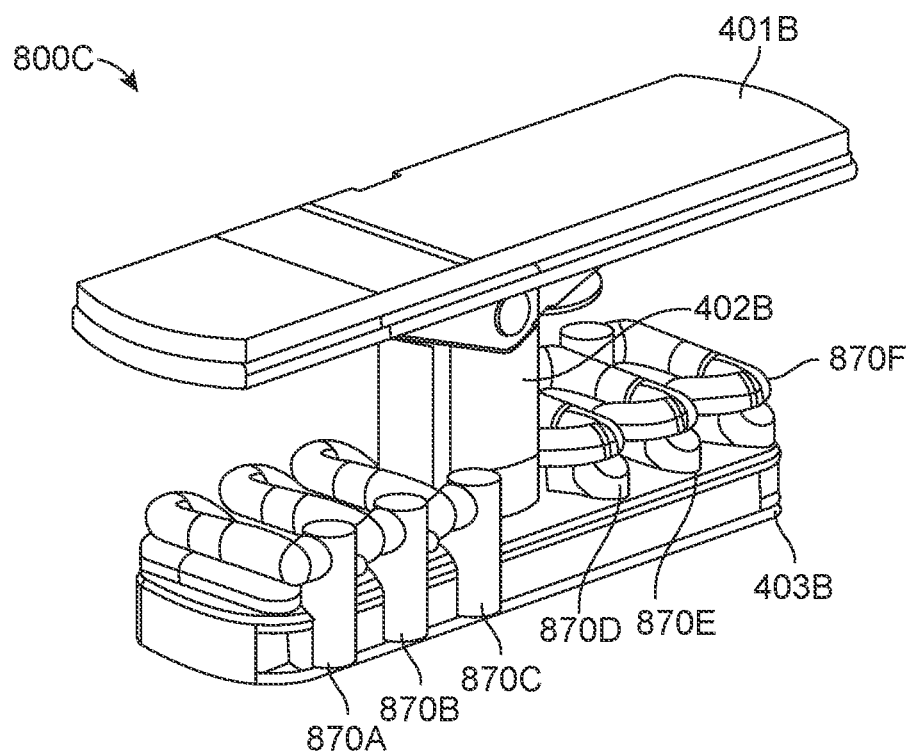
FIG. 8F is another isometric view of robotic arms stowed above a base of a surgical robotics system according to one embodiment.

FIG. 8F is another isometric view of robotic arms stowed above the base 403B of the surgical robotics system 800C according to one embodiment. The robotic arms are rail-mounted instead of column-mounted. Rail-mounted robotic arms are further described with reference to FIGS. 9A-B and FIGS. 10A-D in Section IX. Rail-Mounted Robotic Arms and Section X. Rails, respectively. The surgical robotics system 800C is an embodiment of the surgical robotics system 900B further described with reference to FIG. 9B in Section IX. Rail-Mounted Robotic Arms. The robotic arms 870C, 870D, 870E, 870F, 870G, and 870H are in a stowed configuration.

Figure 8G:
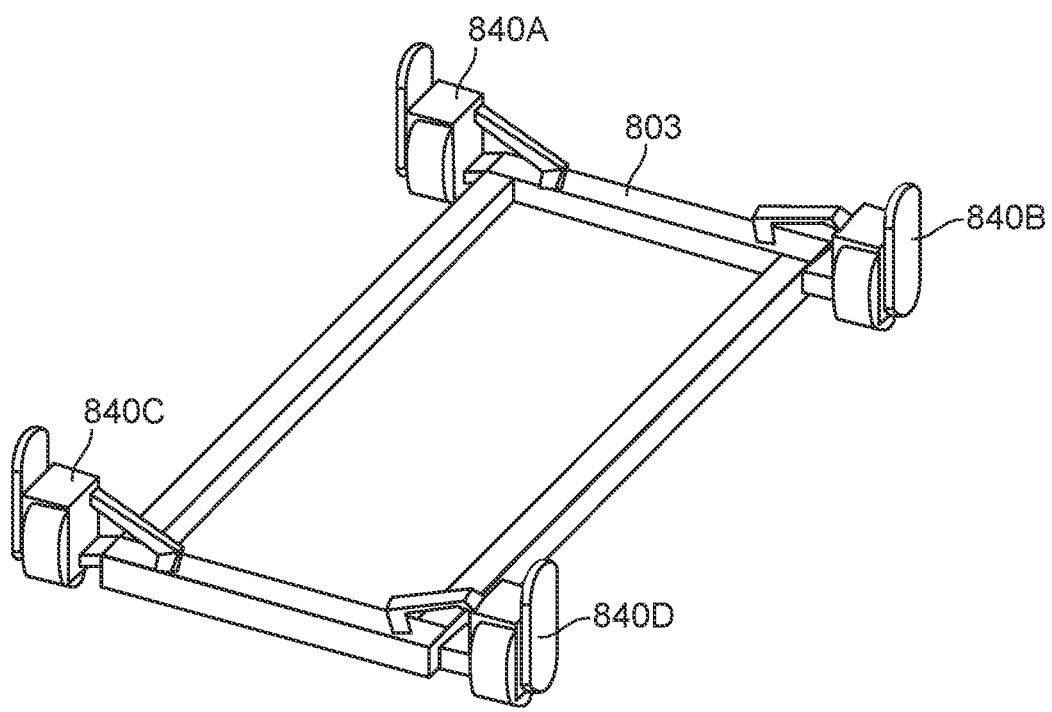
FIG. 8G is an isometric view of outrigger casters on a base of a surgical robotics system according to one embodiment.

FIG. 8G is an isometric view of outrigger casters on a base 803 of a surgical robotics system according to one embodiment. The base 803 shown in FIG. 8G includes four outrigger casters 840A, 840B, 840C, and 840D, each substantially the same as each other and positioned at a different corner of the base 803, though it should be noted that, in other embodiments, a base may include any number of outrigger casters positioned in other locations on the base. The outrigger casters 840A, 840B, 840C, and 840D are each in a mobile configuration, i.e., the caster wheel physically contacts the ground. Thus, a user of the surgical robotics system may transport the surgical robotics system using the caster wheels, e.g., to a storage area when the surgical robotics system is not in use.

Figure 8H:
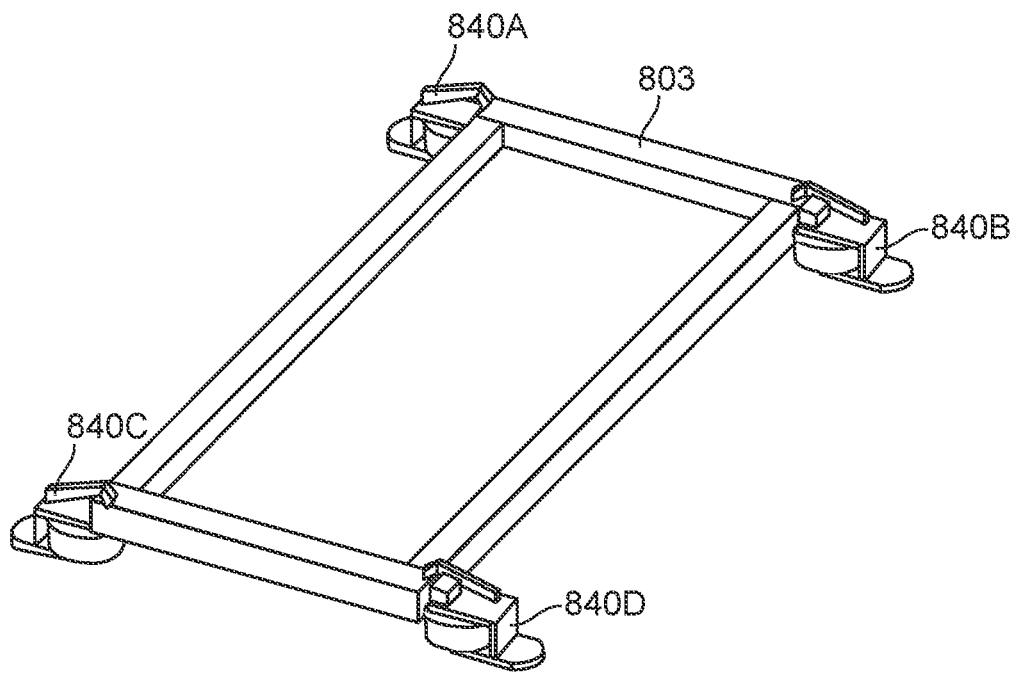
FIG. 8H is another isometric view of the outrigger casters on the base of the surgical robotics system according to one embodiment.

FIG. 8H is another isometric view of the outrigger casters 840A, 840B, 840C, and 840D on the base 803 of the surgical robotics system according to one embodiment. The outrigger casters 840A, 840B, 840C, and 840D are each in a stationary configuration, i.e., the outrigger caster is rotated such that the caster wheel does not physically contact the ground. Thus, the surgical robotics system may be stabilized and immobilized during a surgical procedure.

Figure 8I:
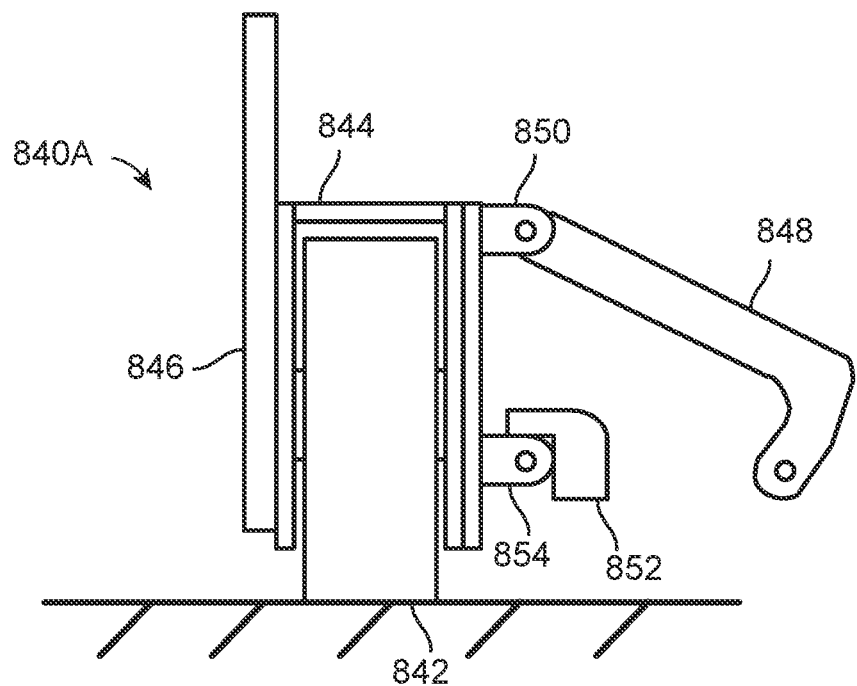
FIG. 8I is a side view of an outrigger caster in a mobile configuration according to one embodiment.

FIG. 8I is a side view of the outrigger caster 840A in a mobile configuration according to one embodiment. The outrigger caster 840A includes a caster wheel 842 movably coupled to an outrigger mount 844. The outrigger mount 844 is coupled to a foot 846. The first linkage 848 is movably coupled to the outrigger mount 844 by the first hinge 850. The second linkage 852 is movably coupled to the outrigger mount 844 by the second hinge 854. In the mobile configuration, the caster wheel 842 may rotate to move the outrigger caster 840 along the ground.

Figure 8J:
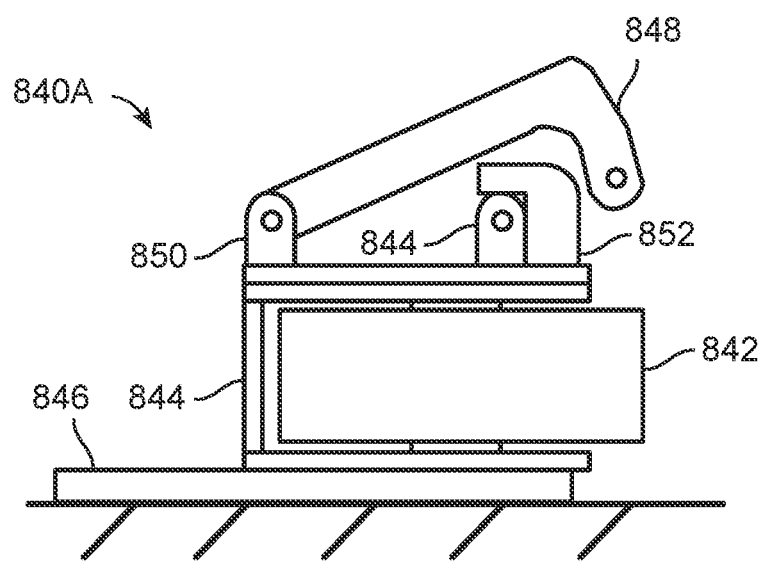
FIG. 8J is a side view of the outrigger caster in a stationary configuration according to one embodiment.

FIG. 8J is a side view of the outrigger caster 840A in a stationary configuration according to one embodiment. In the stationary configuration, the caster wheel 842 may freely rotate, but the caster wheel 842 does not move the outrigger caster 840A because the caster wheel 842 is not physically in contact with the ground. The surgical robotics system (or a user) rotates the outrigger caster 840A, e.g., 90 degrees, to change the outrigger caster 840A from the mobile configuration to the stationary configuration. Thus, the foot 846 now physically contacts the ground, and helps prevent the surgical robotics system from moving. The foot 846 may have a larger footprint relative to the caster wheel 842 to provide additional stability on the ground. The linkages 848 and 852 are positioned such that they do not interfere with the rotational path of the outrigger caster 840A. Combining the caster wheel 842 and the foot 846 in the outrigger caster 840A is advantageous, e.g., because the outrigger caster 840A allows the surgical robotics system to change between the mobile and stationary configurations using a compact mechanism, compared to having separate mechanisms for casters and stabilization. Further, in use cases of surgical robotics systems including swivel segments that rotate a patient lying on the swivel segment away from a corresponding table (e.g., as illustrated in FIGS. 7C-D), the feet of outrigger casters (in the stationary configuration) help prevent the surgical robotics system from tipping over due to the center of mass of the patient extending beyond the table base.

Alternative views and embodiments of the base 403B including the above mentioned components are further illustrated and described at least in U.S. Provisional Application No. 62/203,530 filed Aug. 11, 2015.

IX. Rail-Mounted Robotic Arms

Figure 9A:
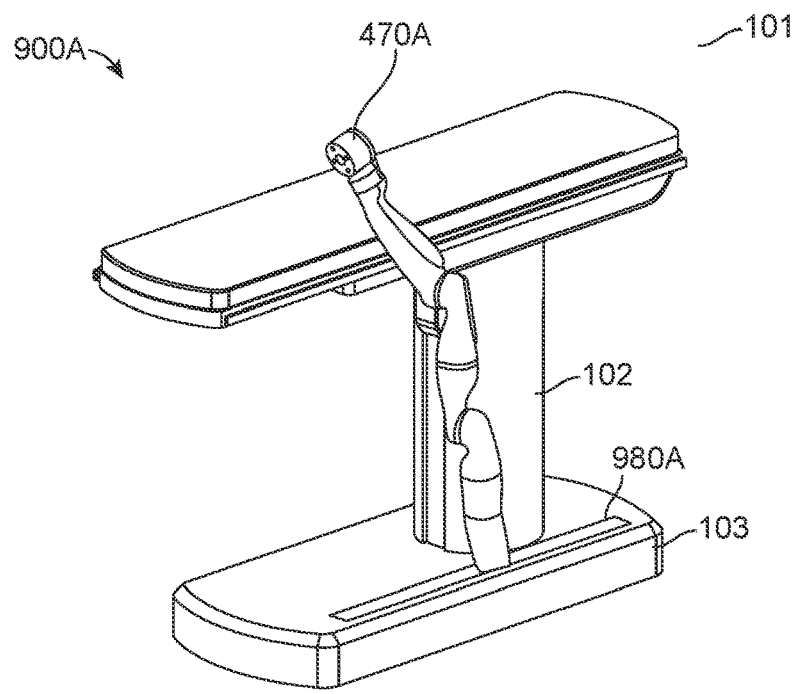
FIG. 9A is an isometric view of a surgical robotics system with a rail-mounted robotic arm according to one embodiment.

FIG. 9A is an isometric view of a surgical robotics system 900A with a rail-mounted robotic arm according to one embodiment. The surgical robotics system 900A includes a set of robotic arms (including at least arm 470A) and a set of base rails (including at least base rail 980A). The robotic arm 470A is coupled to the base rail 980A. Base rails are further described with respect to FIGS. 10A-D in Section X. Rails below. The base rail 980A is movably coupled to the base 103. Thus, the robotic arm 470A may be referred to as a rail-mounted robotic arm 470A.

Figure 9B:
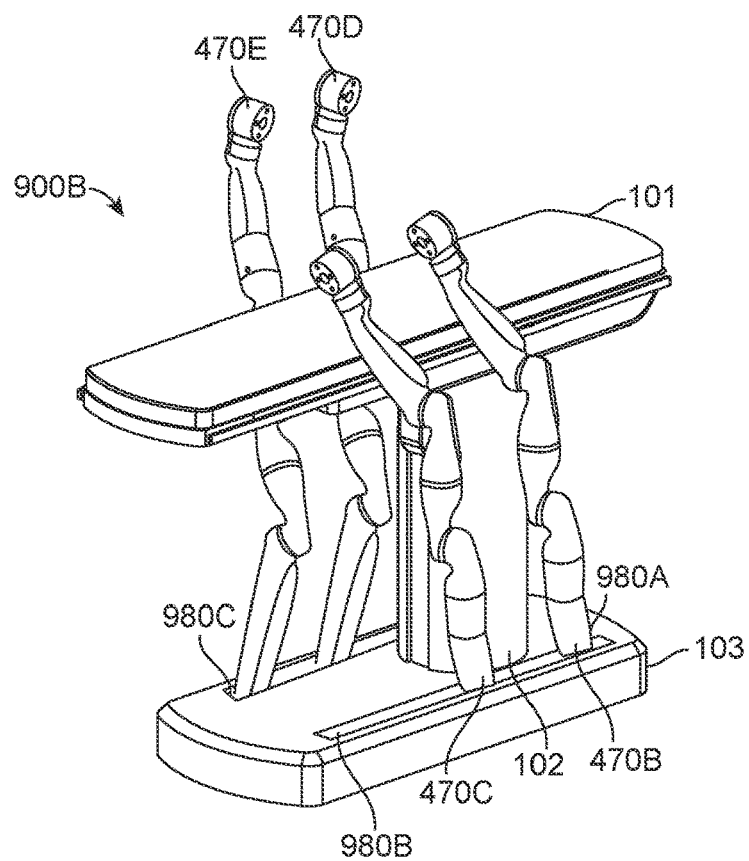
FIG. 9B is an isometric view of a surgical robotics system with rail-mounted robotic arms according to one embodiment.

FIG. 9B is an isometric view of a surgical robotics system 900B with rail-mounted robotic arms according to one embodiment. The surgical robotics system 900B includes robotic arms 470B, 470C, 470D, and 470E each coupled to a first base rail 980B or a second base rail 980C. The first base rail 980B and the second base rail 980C are movably coupled to the base 103.

In other embodiments, the surgical robotics system 900B may include additional or fewer robotic arms and/or base rails. Further, the robotic arms may be coupled to base rails in various configurations. For example, three robotic arms may be coupled to a base rail. Additionally, the surgical robotics system 900B may include three base rails each coupled to a robotic arm.

The surgical robotics system 900B may translate robotic arms mounted to a base rail by translating the base rails relative to the base 103. Base rails may translate beyond the starting footprint of the base 103, which allows the robotic arms to operate in a larger volume of space. Further, the surgical robotics system 900B may translate robotic arms mounted to a base rail independently from each other by translating the robotic arms relative to the base rail. This is advantageous, for example, because the surgical robotics system 900B may position the robotic arms in different configurations to perform a variety of surgical procedures.

Alternative views and embodiments of the surgical robotics system 900B with rail-mounted robotic arms including the above mentioned components are further illustrated and described at least in U.S. Provisional Application No. 62/193,604 filed Jul. 17, 2015 and U.S. Provisional Application No. 62/201,518 filed Aug. 5, 2015.

X. Rails

Figure 10A:
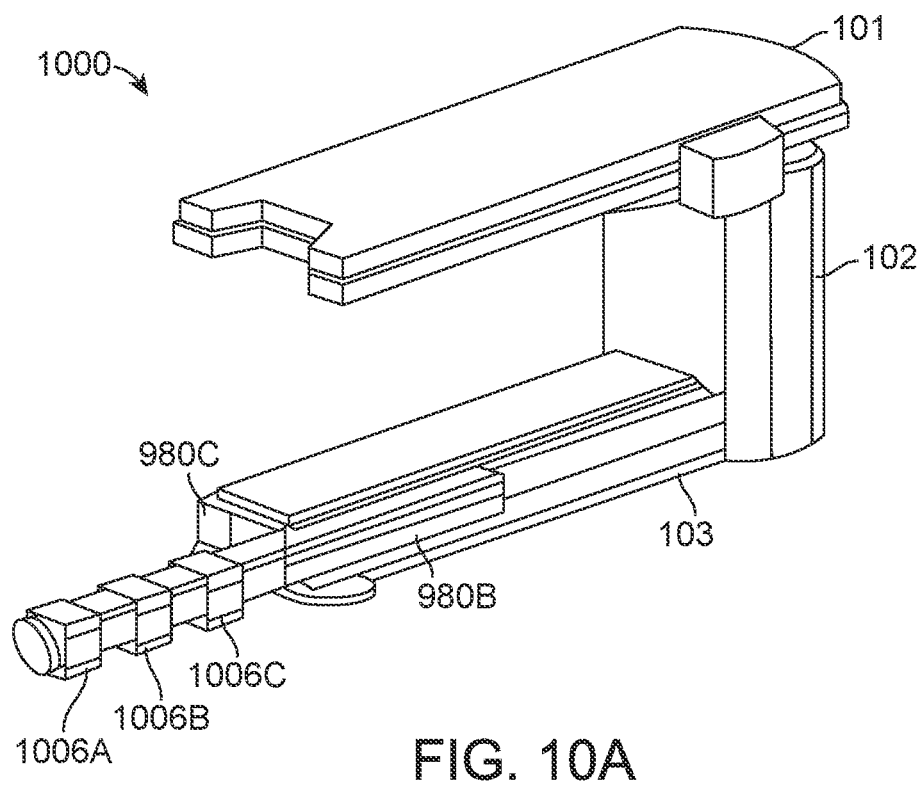
FIG. 10A is an isometric view of base rails of a surgical robotics system according to one embodiment.

FIG. 10A is an isometric view of base rails of a surgical robotics system 1000 according to one embodiment. A base rail includes a set of one or more arm mounts each movably coupled to the base rail. Further, each arm mount is an embodiment of the arm mount 506A or 506B previously described with reference to FIG. 5A in Section V. Column Ring. Specifically, the base rail 980B includes arm mounts 1006A, 1006B, and 1006C.

Figure 10B:
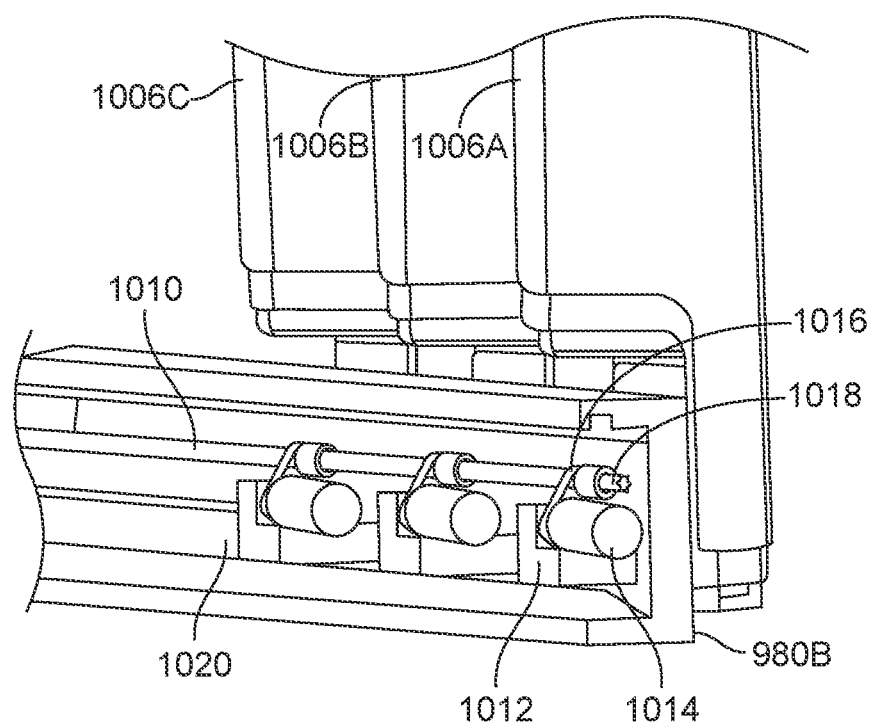
FIG. 10B is an isometric view of arm mounts on the base rail according to one embodiment.

FIG. 10B is an isometric view of arm mounts on the base rail 980B according to one embodiment. The arm mounts 1006A, 1006B, and 1006C each include a belt and pinion assembly. Specifically, the belt and pinion assembly of arm mount 1006A includes a bracket 1012, motor 1014, belt 1016, and pinion 1018. The belt and pinion assemblies of arm mount 1006B and 1006C are constructed similarly.

The surgical robotics system 1000 translates arm mounts—and thus, robotic arms mounted to the arm mounts—along base rails using the belt and pinion assemblies. Specifically, the arm mount 1006A is movably coupled to a channel 1020 of the base rail 980B by the bracket 1012. The bracket 1012 is coupled to motor 1014, belt 1016, and pinion 1018. The motor 1014 is coupled to the pinion 1018 by the belt 1016. Thus, output rotation of the motor 1014 causes the pinion 1018 to rotate. The pinion 1018 is engaged with a rail lead screw 1010 of the base rail 980B. Rotation of the pinion 1018 causes the arm mount 1006A to translate along the base rail 980B parallel to the rail lead screw 1010.

Figure 10C:
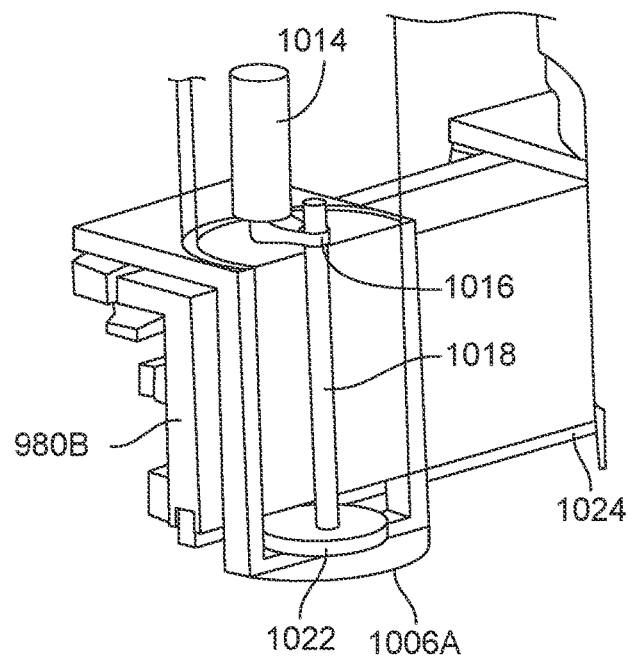
FIG. 10C is an isometric cutaway view of an arm mount on the base rail according to one embodiment.

FIG. 10C is an isometric cutaway view of an arm mount 1006A on the base rail 980B according to one embodiment. The arm mount 1006A includes a belt and pinion assembly. Specifically, the belt and pinion assembly includes a motor 1014, belt 1016, pinion 1018, and bearing 1022. The surgical robotics system 1000 translates the arm mount 1006A—and thus, a robotic arm mounted to the arm mount 1006A—along the base rail 980B using the belt and pinion assembly. The motor 1014 is coupled to the pinion 1018 by the belt 1016. Thus, output rotation of the motor 1014 causes the pinion 1018 to rotate. The pinion 1018 is coupled to the bearing 1022. In some embodiments, the bearing 1022 forms a rack and pinion assembly with the base rail 980B. Specifically, the bearing 1022 is a gear (i.e., the pinion) and is engaged with a rack 1024 of the base rail 980B. Rotation of the pinion 1018 causes the bearing 1022 to translate along the base rail 980B parallel to the rack 1024. Thus, the arm mount 1006A also translates along the base rail 980B.

Figure 10D:
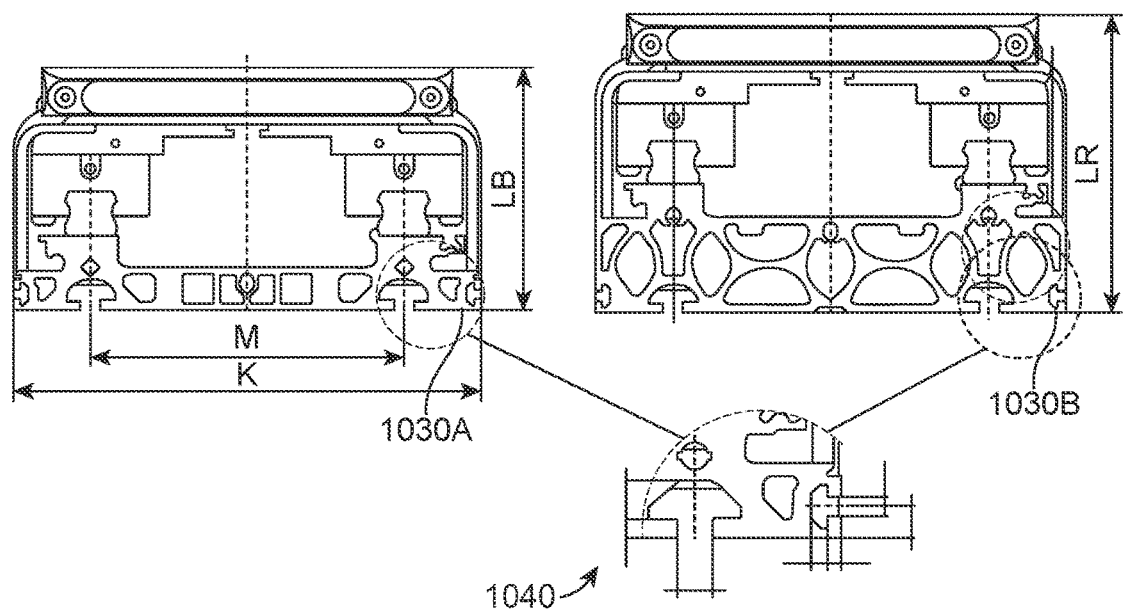
FIG. 10D is cross sectional views of the base rail according to one embodiment.

FIG. 10D is cross sectional views of the base rail 980B according to one embodiment. The cross sectional view 1000A shows a basic profile of an embodiment of the base rail 980B. The cross sectional view 1000B shows a reinforced profile of an embodiment of the base rail 980B. The lower segment 1030B of the reinforced profile is larger in size than the lower segment 1030A of the basic profile. Thus, the reinforced profile is an advantage, for example, because it enables the base rail 980B to withstand greater loads relative to the basic profile. Both the basic and the reinforced profiles have a T-slot attachment 1040, which engages with a corresponding T-slot on a base of a surgical robotics system.

Alternative views and embodiments of the base rails 980A, 980B, and 980C including the above mentioned components are further illustrated and described at least in U.S. Provisional Application No. 62/193,604 filed Jul. 17, 2015 and U.S. Provisional Application No. 62/201,518 filed Aug. 5, 2015.

XI. Alternate Configurations

XI. A. Hybrid Configuration

Figure 11:
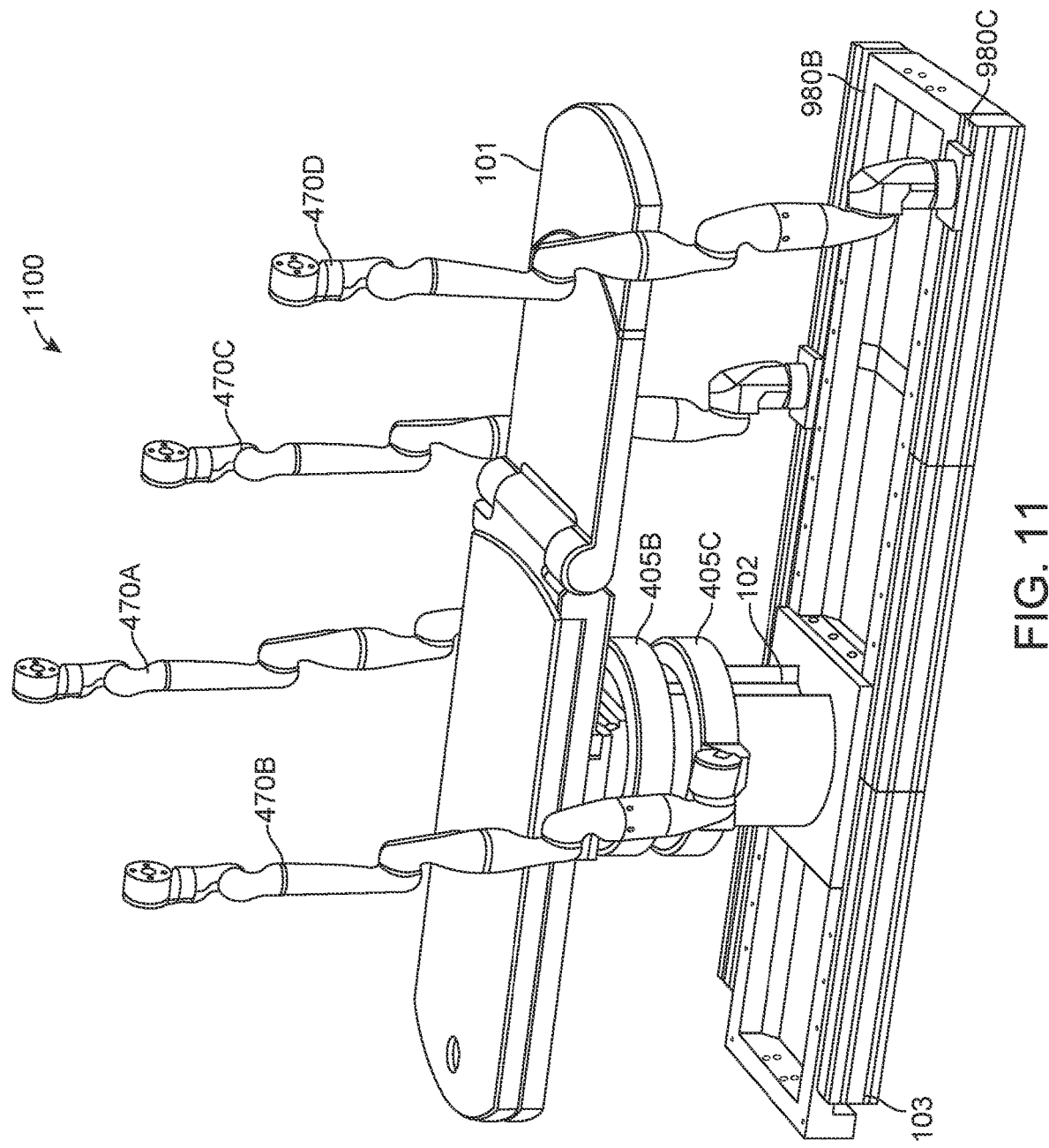
FIG. 11 is an isometric view of a surgical robotics system with column-mounted robotics arms and rail-mounted robotic arms according to one embodiment.

FIG. 11 is an isometric view of a surgical robotics system 1100 with column-mounted robotics arms and rail-mounted robotic arms according to one embodiment. Due to the hybrid configuration including both column-mounted robotics arms and rail-mounted robotic arms, the surgical robotics system 1100 may configure the robotic arms in a greater number of (or different types of) positions compared to surgical robotics systems with column-mounted robotics arms only or rail-mounted robotic arms only. Further, the surgical robotics system 1100 takes advantage of the rotational motion of robotic arms using the column rings as well as translational motion of the robotic arms using the base rails.

XI. B. Cart-Based Robotic Arm Column

Figure 12:
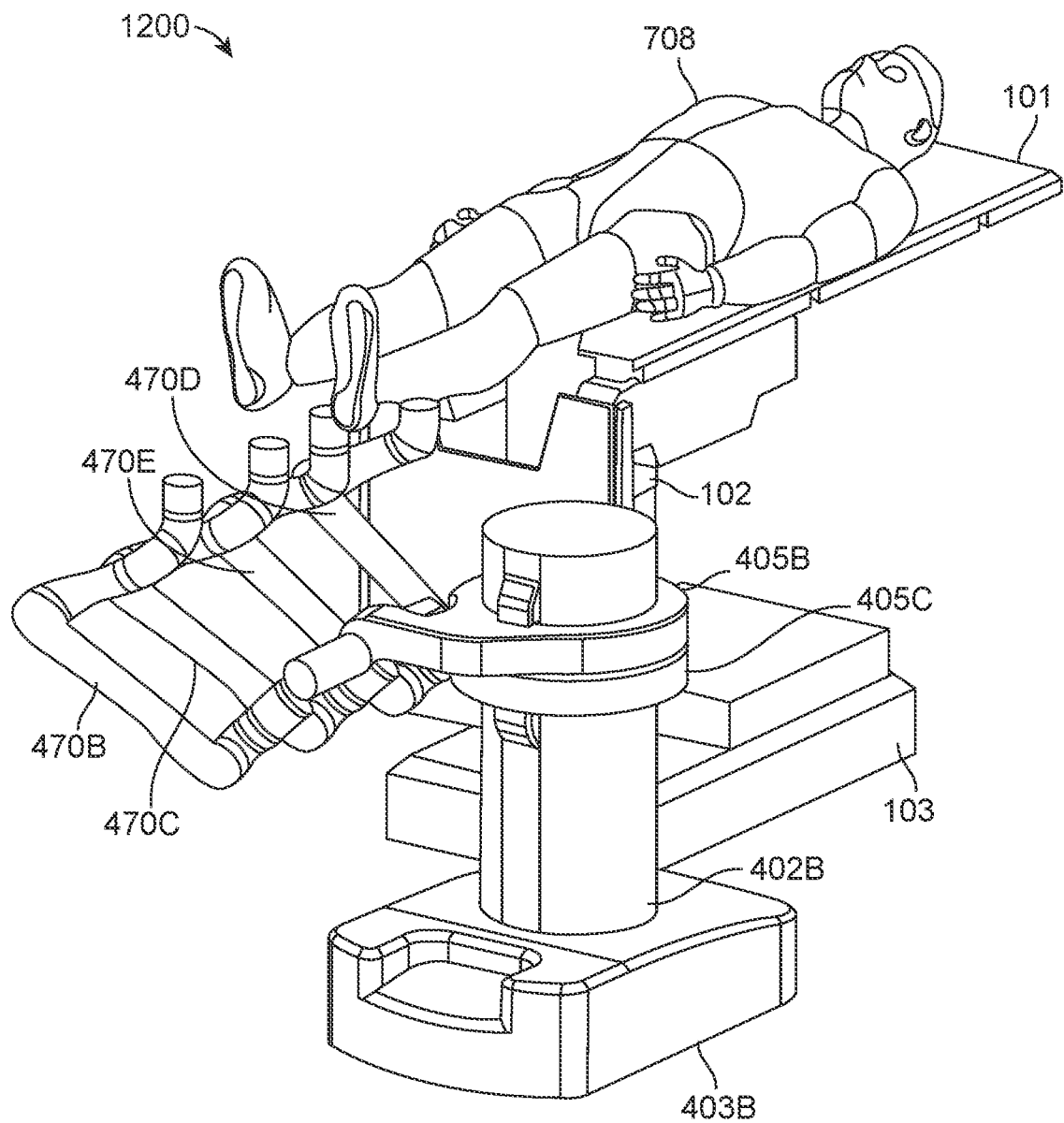
FIG. 12 is an isometric view of a surgical robotics system with column-mounted robotics arms on a platform separate from a table and a base of the surgical robotics system according to one embodiment.

FIG. 12 is an isometric view of a surgical robotics system 1200 with column-mounted robotics arms on a column 402B and base 403B separate, e.g., as a free standing cart, from a table 101, column 102, and base 103 of the surgical robotics system 1200 according to one embodiment. The surgical robotics system 1200 configures the robotic arms to access the lower body area of patient 708 lying on the table 101. In one embodiment, mounting the robotic arms on a cart including the column 402B separate from the column 102 coupled to the table 101 with the patient is advantageous. For example, because the surgical robotics system 1200 may configure the robotic arms to a greater number of (or different types of) positions compared to surgical robotics systems with robotics arms mounted to the same column as the table, which are limited at least in the angles where the table extends past the column 102. Further, the cart may include outrigger casters (e.g., previously described with reference to FIGS. 8G-J in Section VIII. Base) that allow users to more easily transport the robotic arms or keep the cart stationary. Mounting the robotic arms separately can also reduce the number of components and complexity of the column coupled to the table with the patient.

Alternative views and embodiments of the surgical robotics system 1100, the surgical robotics system 1200, and other surgical robotics systems including the above mentioned components are further illustrated and described at least in U.S. Provisional Application No. 62/162,486 filed May 15, 2015, U.S. Provisional Application No. 62/162,467 filed May 15, 2015, U.S. Provisional Application No. 62/193,604 filed Jul. 17, 2015, U.S. Provisional Application No. 62/201, 518 filed Aug. 5, 2015, U.S. Provisional Application No. 62/203,530 filed Aug. 11, 2015, and U.S. Provisional Application No. 62/235,394 filed Sep. 30, 2015.

XII. Adjustable Arm Supports

Robotic surgical systems can include adjustable arm supports as described in this section for supporting one or more robotic arms. The adjustable arm supports can be configured to attach to either a table, a column support of the table, or a base of the table to deploy the adjustable arm supports and robotic arms from a position below the table. In some embodiments, the adjustable arm supports can be attached to a bed (or table) or a cart positioned adjacent to a bed. In some examples, the adjustable arm supports includes a bar, track, or rail on which one or more robotic arms are mounted. In some embodiments, the adjustable arm supports include at least four degrees of freedom that allow for adjustment of the position of the bar, track, or rail. One of the degrees of freedom can allow the adjustable arm supports to be adjusted vertically relative to the table. These and other features of the adjustable arm supports will be described in detail with reference to the examples of FIGS. 13A-21.

Figure 13A:
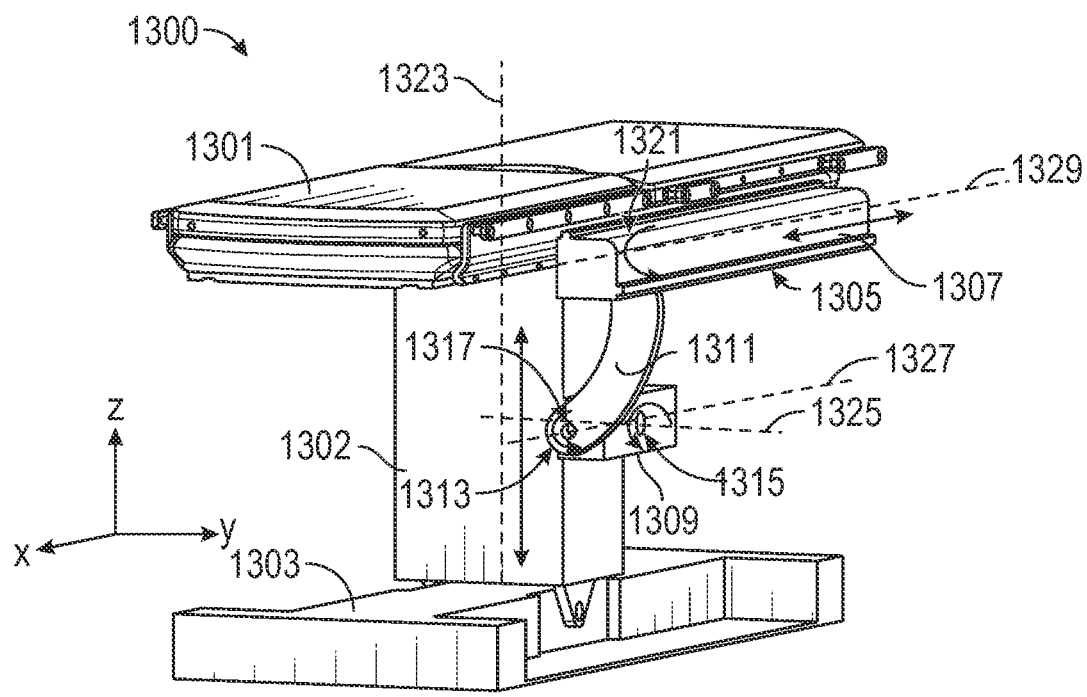
FIG. 13A is an isometric view of a surgical robotics system with an adjustable arm support according to one embodiment.
Figure 13B:
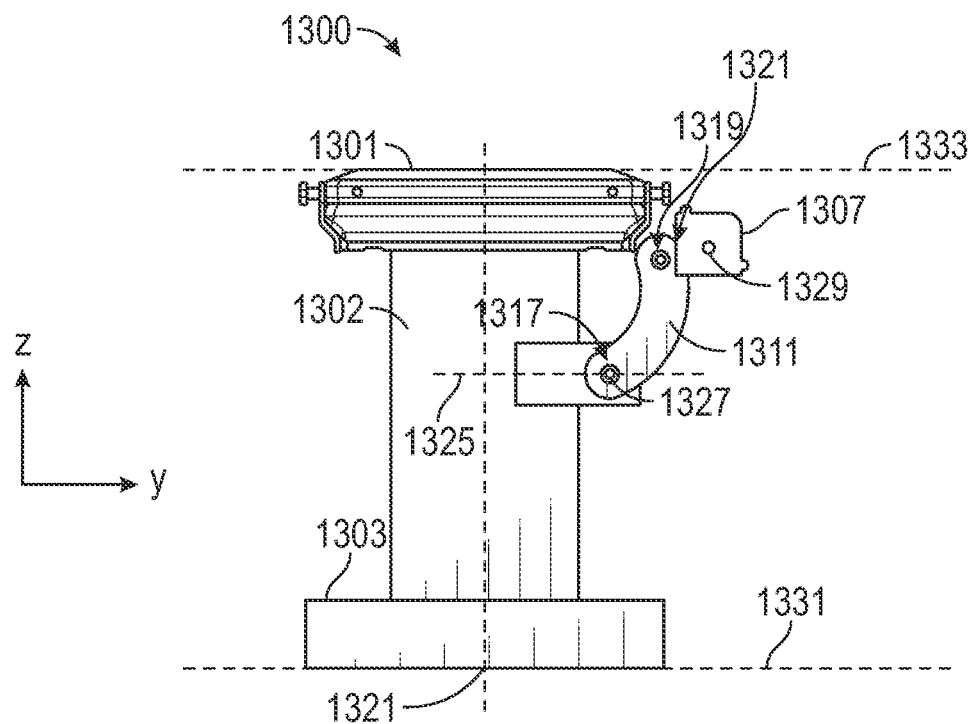
FIG. 13B is an end view of the surgical robotics system with an adjustable arm support of FIG. 13A.

FIGS. 13A and 13B are isometric and end views, respectively, of a surgical robotics system 1300 that includes an adjustable arm support 1305 according to one embodiment. The adjustable arm support 1305 can be configured to support one or more robotic arms (see, for example, FIGS. 14A-15B) relative to a table 1301. As will be described in greater detail below, the adjustable arm support 1305 can be configured so that it can move relative to the table 1301 to adjust and/or vary the position of the adjustable arm support 1305 and/or any robotic arms mounted to the adjustable arm support 1305 relative to the table 1301. For example, the adjustable arm support 1305 may include one or more degrees of freedom relative to the table 1301 to allow adjustment of the adjustable arm support 1305. Although the system 1300 illustrated in FIGS. 13A and 13B includes only a single adjustable arm support 1305, in some embodiments, systems can include multiple adjustable arm supports (see, e.g., system 1400 of FIG. 14A, which includes two adjustable arm supports 1305A, 1305B).

Surgical robotics systems including adjustable arm supports 1305 as described in this section can be designed to address one or more issues of known surgical robotics systems. For example, one issue with some surgical robotics systems is that they may be bulky, occupying large amounts of room space. This is often because large and elaborate support structures have been necessary to position robotic arms to perform robotic surgical procedures. Some surgical robotics systems include robotic arm support structures that support a plurality of robotic arms above a table that supports a patient during the robotic surgical procedure. For example, common surgical robotics systems include support structures that suspend one or more robotic arms over a table. These support structures are quite large and bulky because, for example, they must extend over and above the table.

Another issue with some surgical robotics systems is that they can be overly cumbersome. Due to, for example, the large and bulky support structures required by some surgical robotics systems as described above, these systems are not easily moved, which can be disadvantageous. Before and after surgery, it can be desirable to quickly and smoothly clear the robotic arms from a surgical area to provide easy access for loading a patient onto or removing a patient from the table. This has proven to be difficult with some surgical robotics systems because of the large and bulky support structures and the cumbersome nature of these systems. Some surgical robotics systems are not easily stored or moved.

Further, some surgical robotics systems have limited flexibility or versatility. That is, some surgical robotics systems are designed for a particular surgical procedure, and accordingly, do not work well for other types of surgical procedures. For example, a surgical robotics system that is configured for laparoscopic surgery may not work well for endoscopic surgery, or vice versa. In some instances, this is because the robotic arms used during the procedures need to be positioned in different locations relative the patient and/or table during different types of surgical procedures, and the support structures of conventional surgical robotics systems are not capable of accommodating the different positions of the robotic arms. Further, as mentioned above, some surgical robotics systems include support structures that suspend one or more robotic arms above the patient and table. It may be difficult to perform certain medical procedures with robotic arms mounted in this position.

Finally, some surgical robotics systems include robotic arms that are fixedly mounted to their corresponding support structures, and/or support structures themselves that are fixedly mounted or positioned. These systems may rely on articulation of the robotic arms alone to adjust the position of the robotic arms and/or surgical tools mounted thereto. Because the arms and/or supports are fixed in position, this can greatly limit the overall flexibility of these systems. The fixed nature of the robotic arms and/or supports of some systems may further limit the ability of these systems to avoid collisions between the arms and/or other objects (e.g., the patient, the table, other equipment, etc.) during surgery.

The system 1300 of FIGS. 13An and 13B including the adjustable arm support 1305, as well as the other systems described in this section, can be configured to address (e.g., reduce or eliminate) one or more of the issues associated with some surgical robotics systems discussed above. For example, the systems described herein can be less bulky than some systems. The systems described herein can occupy less physical space than some systems. The systems described herein can be less cumbersome than some systems. For example, the systems described herein can be readily mobile and/or can be configured to store the arm supports and robotic arms quickly and easily to allow convenient access to the patient and/or table. The systems described herein can be highly flexible and configured for use in a wide variety of surgical procedures. For example, in some embodiments, the systems are configured for both laparoscopic and endoscopic procedures. The systems described herein can be configured to reduce collisions between the various robotic arms and other objects in the operating room.

In some embodiments, one or more of these advantages can be achieved by inclusion of one or more adjustable arm supports 1305 as described herein. As mentioned above, the adjustable arm supports 1305 can be configured so as to be able to move relative to the table 1301 to adjust and/or vary the position of the adjustable arm support 1305 and/or any robotic arms mounted to the adjustable arm support 1305 relative to the table 1301. For example, the adjustable arm supports 1305 can be capable of being stowed (for example, below the table 1301) and subsequently elevated for use. In some embodiments, the adjustable arm supports 1305 can be stowed in or near a base that supports the table 1301. In some embodiments, the adjustable arm supports 1305 can be stowed in one or more recesses formed along a central longitudinal axis of the base. In other embodiments, the adjustable arm supports 1305 can be stowed in one or more recesses offset from a central longitudinal axis of the base. Upon elevation, the adjustable arm supports 1305 can be positioned near the patient, but below the table 1301 (e.g., below the upper surface of the table 1301). In other embodiments, the arm supports 1305 can be raised above the table 1301 (e.g., above the upper surface of the table). Such a configuration can be useful, for example, when an adjustable arm support is positioned behind a patient lying on his side.

In some embodiments, the adjustable arm support 1305 is attached to the bed with a support structure that provides several degrees of freedom (e.g., lift, lateral translation, tilt, etc.). In the illustrated embodiment of FIGS. 13A and 13B, the arm support 1305 is configured with four degrees of freedom, which are illustrated with arrows in FIG. 13A. A first degree of freedom allows for adjustment of the adjustable arm support in the z-direction ("Z-lift"). For example, as will be described below, the adjustable arm support 1305 can include a carriage 1309 configured to move up or down along or relative to a column 1302 supporting the table 1301. A second degree of freedom can allow the adjustable arm support 1305 to tilt. For example, the adjustable arm support 1305 can include a rotary joint, which can, for example, permit the arm support 1305 to be aligned with a bed in a Trendelenburg position. A third degree of freedom can allow the adjustable arm support to pivot up as shown. As will be described below, this degree of freedom can be used to adjust a distance between the side of the table 1301 and the adjustable arm support 1305. A fourth degree of freedom can permit translation of the adjustable arm support 1305 along a longitudinal length of the table. Arm supports 1305 that include one or more of these degrees of freedom can address one or more of the issues associated with some systems noted above by providing a highly positionable support to which various robotic arms can be attached. The adjustable arm support 1305 can allow for adjustment of the position of the robotic arms relative to, for example, the table 1301. In some embodiments, these degrees of freedom can be controlled serially, in which one movement is performed after another. In other embodiments, different degrees of freedom can be controlled in parallel. For example, in some embodiments, one or more linear actuators can provide both Z-lift and tilt.

These degrees of freedom, as well as other features of the adjustable arm support 1305, will now be described in greater detail with reference to FIGS. 13A and 13B, which are isometric and end views, respectively, of the surgical robotics system 1300, which includes the adjustable arm support 1305 according to one embodiment. In the illustrated embodiment, the system 1300 includes the table 1301. In some embodiments, the table 1301 may be similar to the tables described above. In the illustrated embodiment, the table 1301 is supported by a column 1302, which is mounted to a base 1303. The base 1303 can be configured to rest on a support surface, such as a floor. Thus, the base 1303 and the column 1302 support the table 1301 relative to the support surface. FIG. 13B, illustrates a support surface plane 1331. In some embodiments, the table 1301 can be supported by one or more supports, wherein one of the supports comprises the column 1302. For example, the table 1301 can be supported by a Stewart mechanism comprising a plurality of parallel actuators.

The system 1300 can also include the adjustable arm support 1305. In the illustrated embodiment, the adjustable arm support 1305 is mounted to the column 1302. In other embodiments, the adjustable arm support 1305 can be mounted to the table 1301 or the base 1303. As mentioned above, the adjustable arm support 1305 is configured so that the position of the adjustable arm support 1305 can be adjusted relative to the table 1301. In some embodiments, the position of the adjustable arm support 1305 can also be adjusted relative to the column 1302 and/or base 1303.

The adjustable arm support 1305 can include a carriage 1309, a bar or rail connector 1311, and a bar or rail 1307. The bar or rail 1307 can comprise a proximal portion and a distal portion. One or more robotic arms can be mounted to the rail 1307, as shown, for example, in FIGS. 14A-15B. For example, in some embodiments, one, two, three, or more robotic arms can be mounted to the rail 1307. Further, in some embodiments, the robotic arms that are mounted to the rail can be configured to move (e.g., translate) along the rail 1307, such that the position of the robotic arms on the rail 1307 can be adjusted relative to one another, thereby reducing the risk of collision between the robotic arms. This will be described in greater detail below. In the illustrated embodiment, the rail 1307 is connected to the bar or rail connector 1311. The bar or rail connector 1311 is connected to the carriage 1309. The carriage is connected to the column 1302. Other arrangements are possible.

The column 1302 can extend along a first axis 1323. In some embodiments, the first axis 1323 is parallel to the z-axis as illustrated. In some embodiments, the first axis 1323 is a vertical axis. For example, the first axis 1323 can be perpendicular to the support surface or floor on which the system 1300 rests.

The carriage 1309 can be attached to the column 1302 by a first joint 1313. The first joint 1313 can be configured to allow the carriage 1309 (and accordingly the adjustable arm support 1305) to move relative to the column 1302. In some embodiments, the first joint 1313 is configured to allow the carriage 1309 to move along the column 1302 (for example, up and down along the column 1302). In some embodiment, the first joint 1313 is configured to allow the carriage 1309 to move along the first axis 1323 (for example, back and forth along the first axis 1323). The first joint 1313 can comprise a linear or prismatic joint. The first joint 1313 can comprise a powered joint, such as a motorized or hydraulic joint. The first joint 1313 can be configured to provide the first degree of freedom ("Z-lift") for the adjustable arm support 1305.

The adjustable arm support 1305 can include a second joint 1315 as shown. The second joint 1315 can be configured to provide the second degree of freedom (tilt) for the adjustable arm support 1305. The second joint 1315 can be configured to allow the adjustable arm support 1305 to rotate around a second axis 1325 that is different than the first axis 1323. In some embodiments, the second axis 1325 is perpendicular to the first axis 1323. In some embodiments, the second axis 1325 need not be perpendicular relative to the first axis 1323. For example, in some embodiments, the second axis 1325 is at an acute angle to the first axis 1323. In some embodiments, the second axis 1325 extends in the y-direction. In some embodiments, the second axis 1325 may lie in a plane that is parallel to the support surface or floor on which the system 1300 rests. The second joint 1315 can comprise a rotational joint. The second joint 1315 can comprise a powered joint, such as a motorized or hydraulic joint.

In the illustrated embodiment, the second joint 1315 is formed between the carriage 1309 and the column 1302, such that the carriage 1309 can rotate about the second axis 1325 relative to the column 1302. In other embodiments, the second joint 1315 can be positioned in other locations. For example, the second joint 1315 can be positioned between the carriage 1309 and the rail connector 1311, or between the rail connector 1311 and the rail 1307.

As noted above, the second joint 1315 can be configured to allow the adjustable arm support 1305 to rotate about the second axis 1325 to allow for the second degree of freedom (tilt) for the adjustable arm support 1305. As will be described in greater detail with reference to FIG. 16 below, rotating the adjustable arm support 1305 about the second axis 1325 can allow adjustment of a tilt angle of the adjustable arm support 1305. That is, an angle of tilt of the rail 1307 can be adjusted by rotating the adjustable arm support 1305 about the second axis 1325 (see FIG. 16).

The adjustable arm support 1305 can include a third joint 1317 as shown. The third joint 1317 can be configured to provide the third degree of freedom (pivot up) for the adjustable arm support 1305. The third joint 1317 can be configured as a rotational joint to allow the rail connector 1311 to rotate around a third axis 1327 that is different from the first axis 1323 and the second axis 1325. In some embodiments, the third axis 1327 can be perpendicular to the second axis 1325. In other embodiments, the third axis 1327 need not be parallel to the second axis 1325. For example, the third axis 1327 can be at an acute angle relative to the second axis 1325. In some embodiments, the third axis 1327 extends in the x-direction. In some embodiments, the third axis 1327 may lie in a plane that is parallel to the support surface or floor on which the system 1300 rests. The third axis 1327 may lie in the same plane or a different plane than the second axis 1325. When the adjustable arm support 1305 is positioned as shown in FIGS. 13A and 13B, the third axis

1327 can be perpendicular to the first axis 1323; however, as the adjustable arm support 1305 is rotated about the second joint 1315, the angle between the first axis 1323 and the third axis 1327 can vary. In some embodiments, the third axis 1327 can be parallel to the rail 1307.

When configured as a rotational joint, the third joint 1317 can allow the rail connector 1311 to rotate around the third axis 1327. As the rail connector 1311 rotates around the third axis 1327, a distance (for example, measured along the y-direction) between an edge of the table 1301 and the rail 1307 can be adjusted. For example, the distance between the edge of the table 1301 and the rail 1307 would increase as the rail connector 1311 is rotated downward from the position shown in FIG. 13B. Thus, the third joint 1317 can be configured to provide a degree of freedom that allows adjustment of the positioning of the rail 1307 along the y-direction. Further, when configured as a rotational joint, the third joint 1317 can also allow additional adjustment of the position of the rail 1307 along the z-direction. For example, the height of the rail 1307 (along the z-direction) would decrease as the rail connector 1311 is rotated downward from the position shown in FIG. 13B. In some embodiments, the third joint 1317 can allow the rail 1307 to pivot upwards in a "biceps curl" type fashion from a stowed position to an elevated position.

As best seen in FIG. 13B, in the illustrated embodiment, the third joint 1317 is positioned on a first end of the rail connector 1311 that connects the rail connector 1311 to the carriage. An additional joint 1319 can be included at a second end of the rail connector 1311 that connects the rail connector 1311 to the rail 1317. In some embodiments, the position of the third joint 1317 and the additional joint 1319 can be reversed. In some embodiments, the additional joint 1319 is mechanically constrained to the third joint 1317 such that the third joint 1317 and the additional joint 1319 rotate together. For example, the third joint 1317 and the additional joint 1319 can be mechanically constrained via a four-bar linkage. Other methods for mechanical constraint are also possible. Mechanical constraint between the third joint 1317 and the additional joint 1319 can be configured to maintain an orientation of the rail 1307 as the rail connector 1311 is rotated about the third axis 1327. For example, mechanical constraint between the third joint 1317 and the additional joint 1319 can be configured such that, as the rail connector 1311 rotates, an upper surface of the rail 1307 (to which one or more robotic arms can be mounted) continue to face in the same direction. In the illustrated example of FIGS. 13A and 13B, the upper face of the rail 1307 is facing upwards (in the z-direction). Mechanical constraint between the third joint 1317 and the additional joint 1319 can be configured such that the upper face of the rail 1307 remains facing upwards (in the z-direction) as the rail connector 1311 rotates. In some embodiments, mechanical constraint can be replaced with a software-defined constrained. For example, each of the third joint 1317 and the additional joint 1319 can be a powered joint, and software can be used to constrain rotation of each joint together.

In some embodiments, the third joint 1317 can comprise a linear joint or prismatic joint (in place of the rotation joint described above and illustrated in the figures) configured to allow linear displacement of the rail 1307 toward and away from the column 1302 (for example, along the y-direction).

The third joint 1317 can comprise a powered joint. In some embodiments, the third joint 1317 can comprise a motorized or hydraulic joint.

The adjustable arm support 1305 can include a fourth joint 1321 as shown. The fourth joint 1321 can be configured to provide the fourth degree of freedom (translation) for the adjustable arm support 1305. For example, the fourth joint 1321 can be configured to allow the rail 1307 to translate back and forth relative to, for example, the table 1301, the column 1302, the carriage 1309, and/or the rail connector 1311. The rail 1307 can extend along a fourth axis 1329. The fourth joint 1321 can be configured to allow the rail 1307 to translate along the fourth axis 1329. In some embodiments, the fourth axis 1329 can be parallel to third axis 1327. In other embodiments, the fourth axis 1329 can be at a non-parallel (e.g., acute angle) to third axis 1327. In some embodiments, the fourth axis 1329 can be perpendicular to the second axis 1325. In other embodiments, the fourth axis 1329 can be at a non-perpendicular angle (e.g., acute angle) to the second axis 1325. When the adjustable arm support 1305 is positioned as shown in FIGS. 13A and 13B, the fourth axis 1329 can be perpendicular to the first axis 1323; however, as the adjustable arm support 1305 is rotated about the second joint 1315, the angle between the first axis 1323 and the fourth axis 1329 can vary.

The fourth joint 1321 can comprise a linear or prismatic joint. The fourth joint 1321 can comprise a powered joint, such as a motorized or hydraulic joint. In the illustrated embodiment, the fourth joint 1321 is positioned between the bar or rail connector 1311 and the rail 1307.

As will be described in greater detail below with reference to FIGS. 15A and 15B, translation of the rail 1307 can be configured to provide increased longitudinal reach (for example, along the x-direction) for the system 1300. This may improve the flexibility of the system 1300, allowing the system 1300 to be used in a wider variety of surgical procedures.

In some embodiments, the adjustable arm support 1305 is configured to allow for variable positioning of the rail 1307 relative to the table 1301. In some embodiments, the position of the rail 1307 remains below a table support surface plane 1333 that is parallel with an upper surface of the table 1301. This may be advantageous as it may improve the ability to maintain a sterile field above the table support surface plane 1333 during a medical procedure. In the operating environment, medical personal may desire to maintain a sterile field above the surface of the table. As such, there may be heightened requirements or stricter procedures for equipment that is positioned above the surface of the table. For example, equipment positioned above the surface of the table may need to be draped. As such, it may be desirable, and some medical personal may prefer, that the arm support is maintained below the surface of the table. In some instances, when the arm support is maintained below the surface of the table, it may not need to be draped. In other embodiments, however, the adjustable arm support 1305 can adjust the position of the rail 1307 such that it is positioned above the table support surface plane 1333.

In some embodiments, the adjustable arm support 1305 is attached to the base 1303, the column 1302, or the table 1301 at a position below the table support surface plane 1333. As will be described below with reference to FIGS. 18A and 18B, this may advantageously permit the adjustable arm support 1305 (and any attached robotic arms) to be moved to a stowed configuration in which the adjustable arm support 1305 (and any attached robotic arms) are stowed below the table 1301 (see FIG. 18B). This may advantageously make the system 1300 less bulky and/or less cumbersome when compared to previously known surgical robotics systems.

Movement of the arm support 1305 (for example, movement of one or more of the first, second, third, or fourth joints 1313, 1315, 1317, 1321) may be controlled and/or commanded in several ways. For example, the system 1300 can include a controller (e.g., a pendant) either on the bed (patient side) or a surgeon console. As another example, buttons (or other actuation mechanisms) could be included on one or more of the components of the adjustable arm support 1305 (or on one or more of the connected robotic arms). As another example, movement of the adjustable arm support 1305 can be provided automatically by system software, for example, for adjustment within the robot's null space (while maintaining the tooltip position commanded by the surgeon). Additionally, movement of the adjustable arm support 1305 can be provided automatically by system software during setup, deployment, draping, or other workflow steps when tools are not inserted into the patient. Other examples are also possible.

FIGS. 13A and 13B illustrate an embodiment that includes one adjustable arm support 1305. As noted previously, some systems can include more than one adjustable arm support 1305, each supporting one or more robotic arms. In such systems, each adjustable arm support can be configured as described above. Further, in such systems, each adjustable arm support can be controlled independently.

Figure 14A:
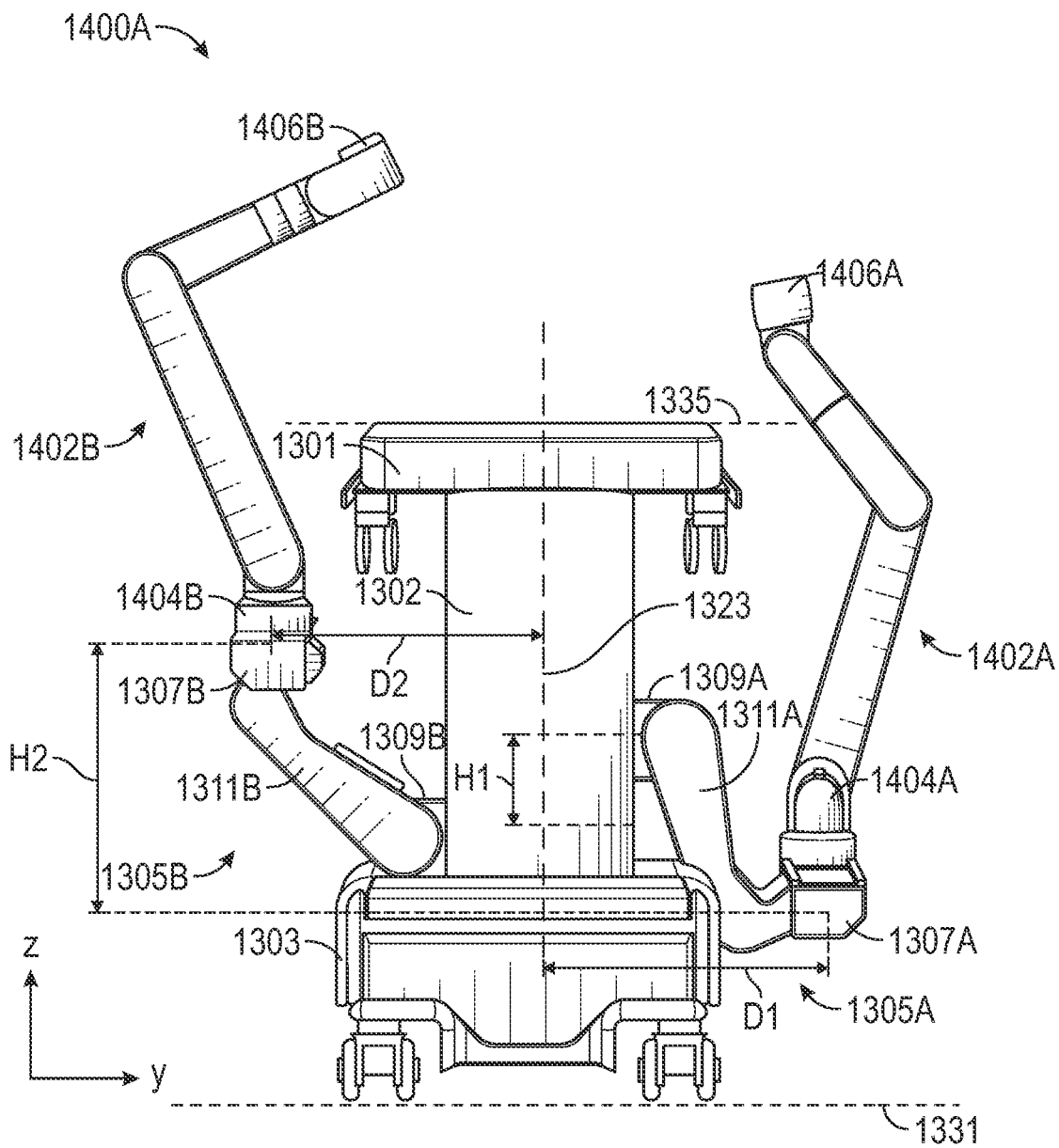
FIG. 14A is an end view of a surgical robotics system with two adjustable arm supports mounted on opposite sides of a table according to one embodiment.

FIG. 14A is an end view of a surgical robotics system 1400A with two adjustable arm supports 1305A, 1305B mounted on opposite sides of the table 1301 according to one embodiment. Each of the adjustable arm supports 1305A, 1305B can be configured as described above. In the illustrated embodiment, a first adjustable arm support 1305A is positioned on a first side of the table 1301 (e.g., the right side as shown in the figure), and a second adjustable arm support 1305B is positioned on a second side of the table 1301 (e.g., the left side as shown in the figure). The second side can be opposite the first side.

Further, a first robotic arm 1402A is illustrated attached to the bar or rail 1307A of the first adjustable arm support 1305A, and a second robotic arm 1402B is illustrated attached to the bar or rail 1307B of the second adjustable arm support 1305B. As illustrated, the first robotic arm 1402A includes a base 1404A attached to the rail 1307A. The distal end of the first robotic arm 1402A includes an instrument drive mechanism 1406A. The instrument drive mechanism 1406A can be configured to attach to one or more robotic medical instruments or tools. Similarly, the second robotic arm 1402B includes a base 1404B attached to the rail 1307B. The distal end of the second robotic arm 1402B includes an instrument drive mechanism 1406B. The instrument drive mechanism 1406B can be configured to attach to one or more robotic medical instruments or tools. Example robotic arms configured for use with the adjustable arm supports 1305 are described below in greater detail in Section XIII (see FIG. 21).

FIG. 14A illustrates that the adjustable arm supports 1305A, 1305B can be independently controlled and positioned. As illustrated, the first adjustable arm support 1305A is positioned at a first height along the first axis 1323, and the second adjustable arm support 1305B is positioned at a second height along the first axis 1323. In some embodiments, the second height can be different and independent from the first height. In other embodiments, the second height can be substantially equivalent to the first height.

In the embodiment in FIG. 14A, the carriage 1309A of the first adjustable arm support 1305A is positioned at a first height along the first axis 1323, and the carriage 1309B of the second adjustable arm support 1305B is positioned at a second height along the first axis 1323 different than the first height. Thus, a height difference H1 can exist between the carriages 1309A, 1309B of the first and second adjustable arm supports 1305A, 1305B. In other embodiments, the carriages 1309A, 1309B of the first and second adjustable arm supports 1305A, 1305B can be positioned at the same height.

Further, FIG. 14A illustrates the position of the bar or rail connectors 1311A, 1311B of the first and second adjustable arm supports 1305A, 1305B, which can also be independently adjusted to have different orientations. For example, as illustrated, the rail connector 1311A of the first adjustable arm support 1305A is rotated downwardly, and the rail connector 1311B of the second adjustable arm support 1305B is rotated upwardly. A height difference H2 can exist between the rails 1307A, 1307B of the first and second adjustable arm supports 1305A, 1305B, as illustrated. Further, in this position, each of the rail connectors 1311A, 1311B, of the first and second adjustable arm supports 1305A, 1305B is positioned at a different distance from the first axis 1323. For example, the rail connector 1311A of the first adjustable arm support 1305A is positioned at a first distance D1 from the first axis 1323, and the rail connector 1311B of the second adjustable arm support 1305B is positioned at a second distance D2 from the first axis 1323. This distance D1 can be different than the distance D2. In some embodiments, the rail connectors 1311A, 1311B, of the first and second adjustable arm supports 1305A, 1305B can be rotated to the same degree and/or the distance D1 can be equal to the distance D2.

Figure 14B:
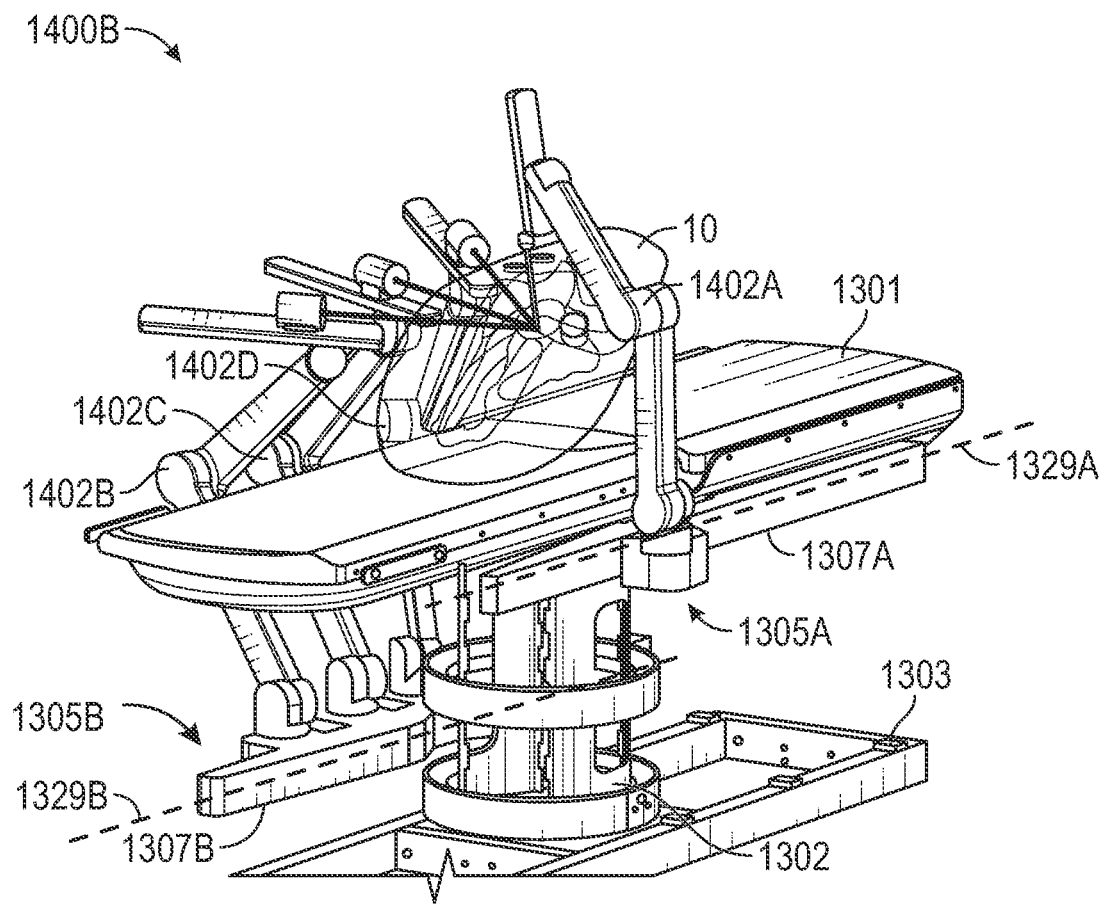
FIG. 14B is an isometric view of a surgical robotics system with two adjustable arm supports and a plurality of robotic arms configured for a laparoscopic procedure according to one embodiment.
Figure 14C:
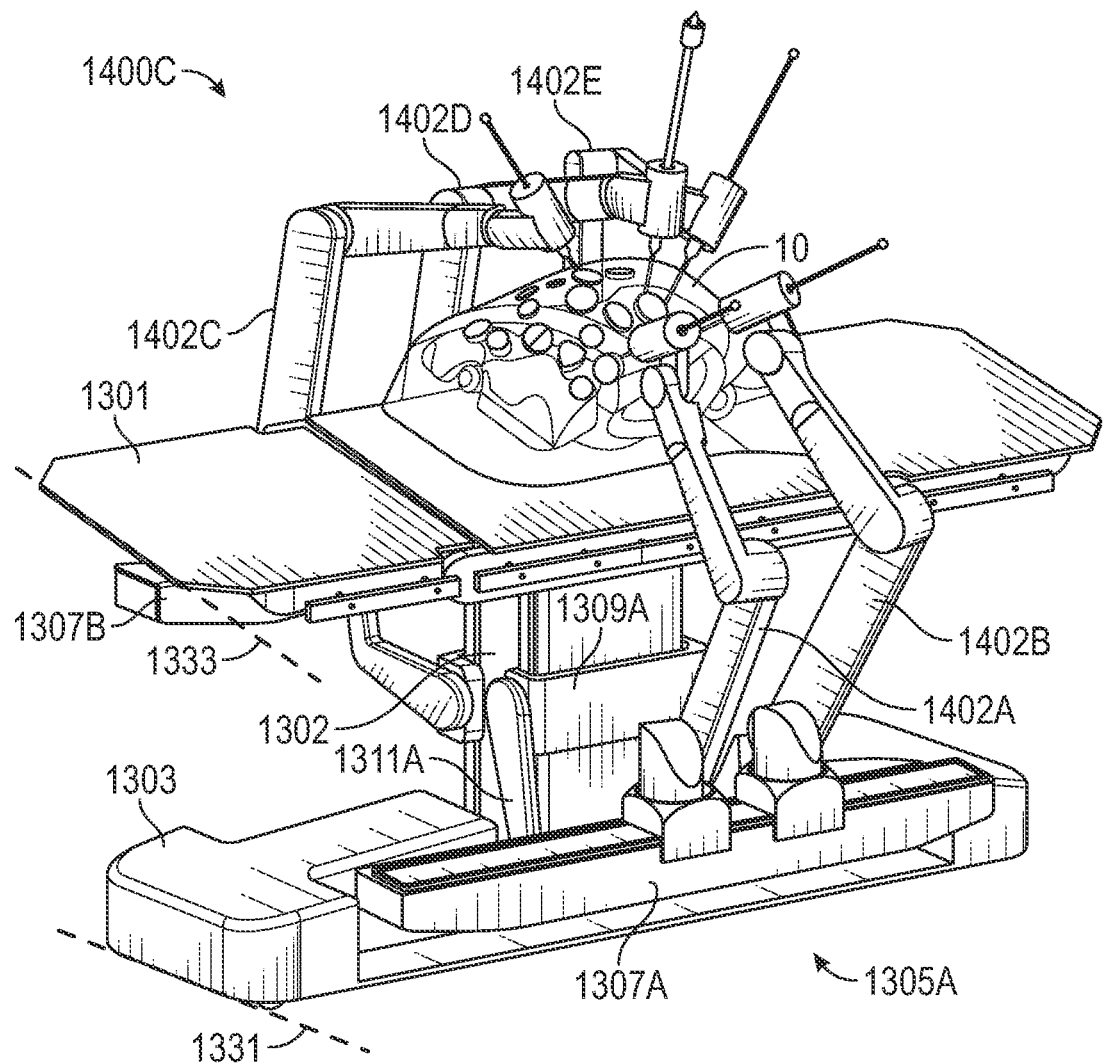
FIG. 14C is an isometric view of a surgical robotics system with two adjustable arm supports and a plurality of robotic arms configured for a laparoscopic procedure according to one embodiment.

FIG. 14A illustrates that the adjustable arm supports 1305A, 1305B can each be positioned or adjusted independently to provide different positions at which the robotic arms attached thereto are supported. FIG. 14A illustrates only one example among many. The adjustable arm supports 1305 can have continuous movement (e.g., vertical or longitudinal) and can be stopped at any point as desired by a surgeon or clinician. This can be beneficial, for example, in creating a height differential between the arm supports, which can be advantageous for certain types of surgeries, such as when one set of robotic arms needs to reach low and the other needs to reach over a patient. For example, as shown in FIG. 14A, the second adjustable arm support 1305B with attached robotic arm 1402B is raised higher than the first adjustable arm support 1305A with attached robotic arm 1402A. This position may be especially helpful when the patient is on its side (e.g., lateral decubitus), such as in a nephrectomy procedure, although one skilled in the art will appreciate that a differential can be beneficial in other procedures as well. FIGS. 14B and 14C provide additional examples.

FIG. 14B is an isometric view of a surgical robotics system 1400B with two adjustable arm supports 1305A, 1305B and a plurality of robotic arms 1402A, 1402B, 1402C, 1402D configured for a laparoscopic procedure according to one embodiment. In the illustrated embodiment, a first adjustable arm support 1305A supports a first robotic arm 1402A, and a second adjustable arm support 1305B supports a second robotic arm 1402B, a third robotic arm 1402C, and a fourth robotic arm 1402D.

The first robotic arm 1402A can be configured to translate back and forth along the rail 1307A of the first adjustable arm support 1305A. That is, the first robotic arm 1402A can be configured to translate along the fourth axis 1329A. This can allow for adjustment of the first robotic arm 1402A relative to the rail 1307A. Similarly, the second robotic arm 1402B, the third robotic arm 1402C, and the fourth robotic arm 1402D can each be configured to translate back and forth along the rail 1307B of the second adjustable arm support 1305B. That is, the second robotic arm 1402B, the third robotic arm 1402C, and the fourth robotic arm 1402D can be configured to translate along the fourth axis 1329B of the second adjustable arm support 1305B. This can allow for adjustment of the second robotic arm 1402B, the third robotic arm 1402C, and the fourth robotic arm 1402D relative to the rail 1307B. Further, each of the second robotic arm 1402B, the third robotic arm 1402C, and the fourth robotic arm 1402D can be independently moved along the rail 1307B such that the spacing between each of the second robotic arm 1402B, the third robotic arm 1402C, and the fourth robotic arm 1402D can be adjusted. Among other things, FIG. 14B illustrates that in some embodiments, the position of each robotic arm 1402 along the corresponding rail 1307 of the corresponding arm support 1305 can be independently controlled and adjusted.

Further, FIG. 14B illustrates another example of a height differential between the first and second arm supports 1305A, 1305B. In the illustrated embodiment, a patient 10 is positioned on his or her side during a laparoscopic procedure. The first adjustable arm support 1305A is positioned in a high position (but below the surface of the table 1301) such that the first robotic arm 1402A can reach over the patient 10. As illustrated, the second adjustable arm support 1305B is positioned at a lower position such that the second robotic arm 1402B, the third robotic arm 1402C, and the fourth robotic arm 1402D can access an anterior side of the patient.

In some embodiments, one or more of the robotic arms 1402A, 1402B, 1402C, 1402D can operate laparoscopic surgical instruments or tools, and one or more of the other of the 1402A, 1402B, 1402C, 1402D can operate a camera laparoscopically inserted into the patient. In some embodiments, the one or more laparoscopic surgical instruments and the camera can be sized and configured to extend through one or more laparoscopic ports in a patient.

FIG. 14C is an isometric view of a surgical robotics system 1400C with two adjustable arm supports 1305A, 1305B and a plurality of robotic arms 1402A, 1402B, 1402C, 1402D, 1402E configured for a laparoscopic procedure according to one embodiment. In the illustrated embodiment, a first adjustable arm support 1305A supports a first robotic arm 1402A and a second robotic arm 1402B, and a second adjustable arm support 1305B supports a third robotic arm 1402C, a fourth robotic arm 1402D, and a fifth robotic arm 1402E.

In the illustrated embodiment, the table 1301 supporting the patient 10 is positioned at an angle relative to the floor. That is, rather than being parallel, as illustrated for example, in FIG. 14B, a table surface plane 1333 is angled with respect to a support surface plane 1331. The first adjustable arm support 1305A, positioned on the lower side of the table 1301, can be positioned in a low position such that the first robotic arm 1402A and the second robotic arm 1402B can access the patient 10. As illustrated, the second adjustable arm support 1305B is positioned at a higher position (which may be lower than the table support surface 1333) such that the third robotic arm 1402C, the fourth robotic arm 1402D, and the fifth robotic arm 1402E can reach over and access the patient 10.

Figure 15A:
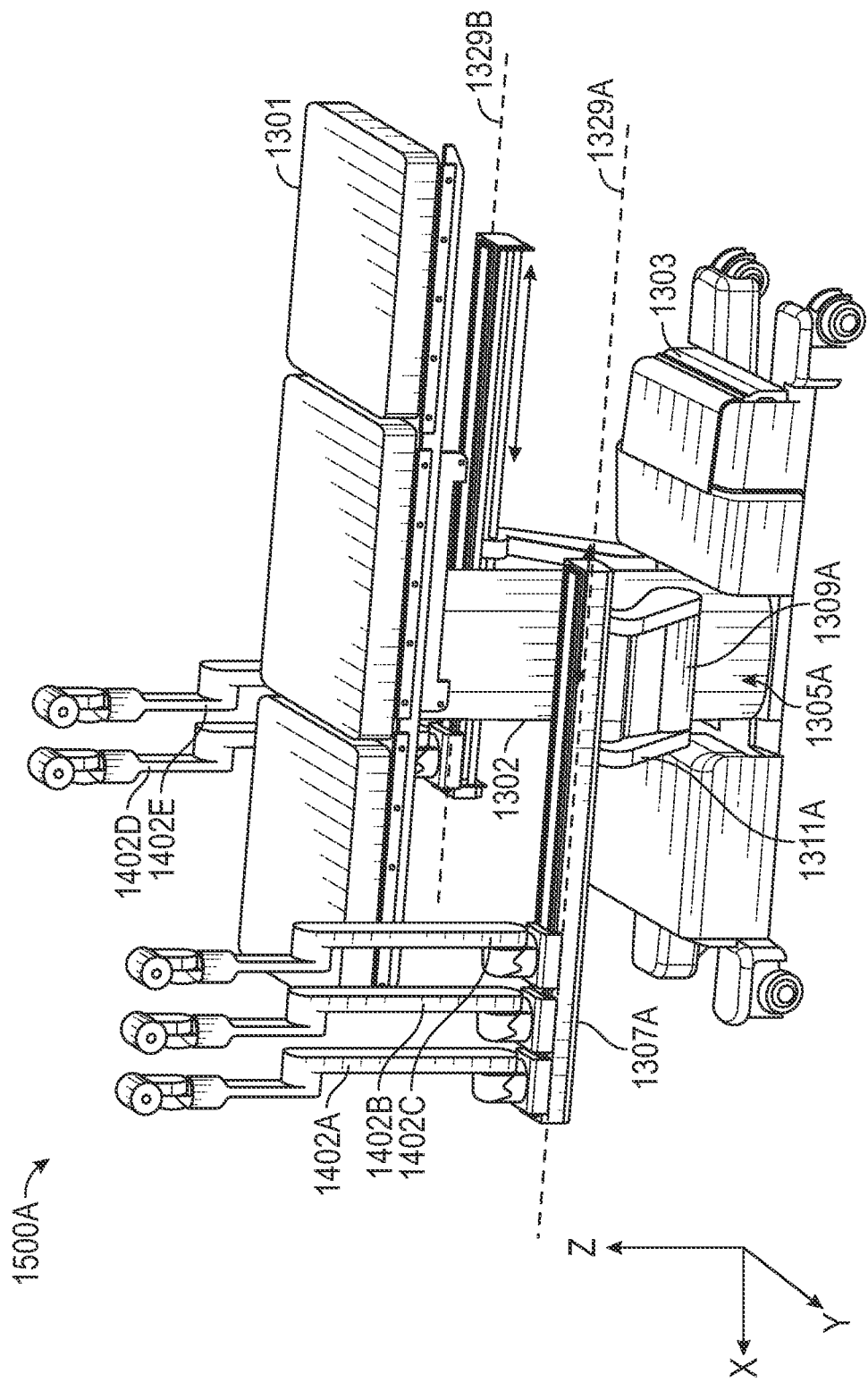
FIG. 15A is an isometric view of a surgical robotics systems with two adjustable arm supports that are configured to translate to adjust the position of the adjustable arm supports according to one embodiment.

FIG. 15A is an isometric view of a surgical robotics systems with two adjustable arm supports 1305A, 1305B that are configured to translate to adjust the position of the adjustable arm supports 1305A, 1305B according to one embodiment. As described previously, the adjustable arm support 1305 can include a fourth joint 1321 configured to allow the rail 1307 to translate along the fourth axis 1329 relative to the base 1302, column 1302, table 1301, carriage 1309, and/or rail connector 1311. FIG. 15A illustrates that, in embodiments that include two adjustable arm supports 1305A, 1305B, the rail 1307A, 1307B of each adjustable arm support 1305A, 1305B can be translated along its corresponding axis 1329A, 1329B, independently of the other rail. For example, in FIG. 15A, the rail 1307A can translate back and forth along the axis 1329A, independently from the rail 1307B, which can also translate back and forth along the axis 1329B.

In other embodiments, rails 1307 are not configured to translate along the axis 1329. For example, in some embodiments, longer rails 1307 can be used in lieu of translating rails. In some embodiments, translation of the rails 1307 permits shorter rails 1307 to be used while still maintaining the overall versatility and flexibility of the system. In some embodiments, shorter rails 1307 (with or without translation) can improved the ability of system to be stowed below the table 1301 (see FIG. 18B).

Figure 15B:
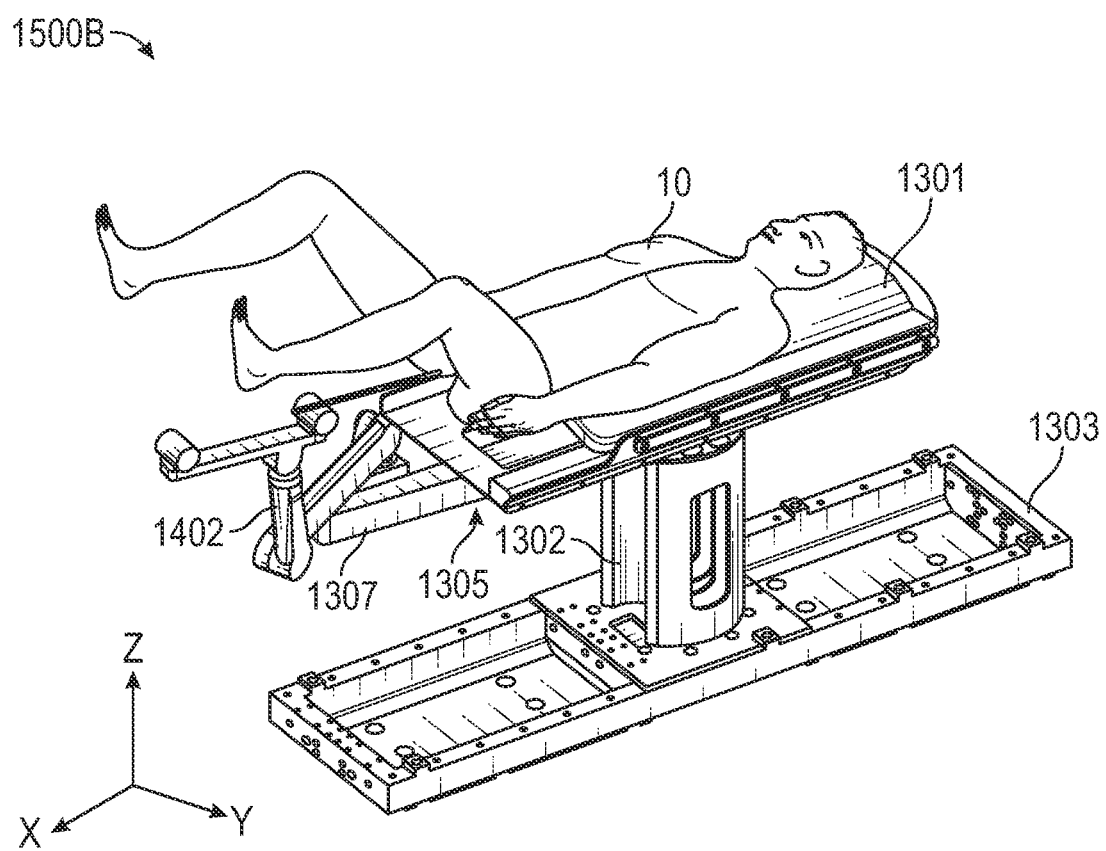
FIG. 15B is an isometric view of a surgical robotics system with an adjustable arm support and robotic arm configured for an endoscopic procedure according to one embodiment.

FIG. 15B is an isometric view of a surgical robotics system 1500B with an adjustable arm support 1305 and robotic arm 1402 configured for an endoscopic procedure according to one embodiment. FIG. 15B illustrates that, in some embodiments, a system including an adjustable arm support 1305 can be configured to provide a long longitudinal range of motion that can be useful, for example, in an endoscopic procedure, such as a ureteroscopy, wherein an endoscope is inserted into the patient through the groin area. For example, as shown in FIG. 15B, the rail 1307 can be translated all the way toward the foot of the table 1301. From there, the arm 1402 can further extend longitudinally to position an instrument between the legs of the patient 10 for access to the groin area. Although only one robotic arm 1402 is illustrated in FIG. 15B, in other embodiments, multiple robotic arms, either mounted on the same adjustable arm support 1305 or an additional arm support 1305 can be configured for use in an endoscopic procedure. FIG. 15B provides only one example of an endoscopic procedure. Systems including adjustable arm supports 1305 can be used in other types of endoscopic procedures, such as bronchoscopy, for example.

Figure 16:
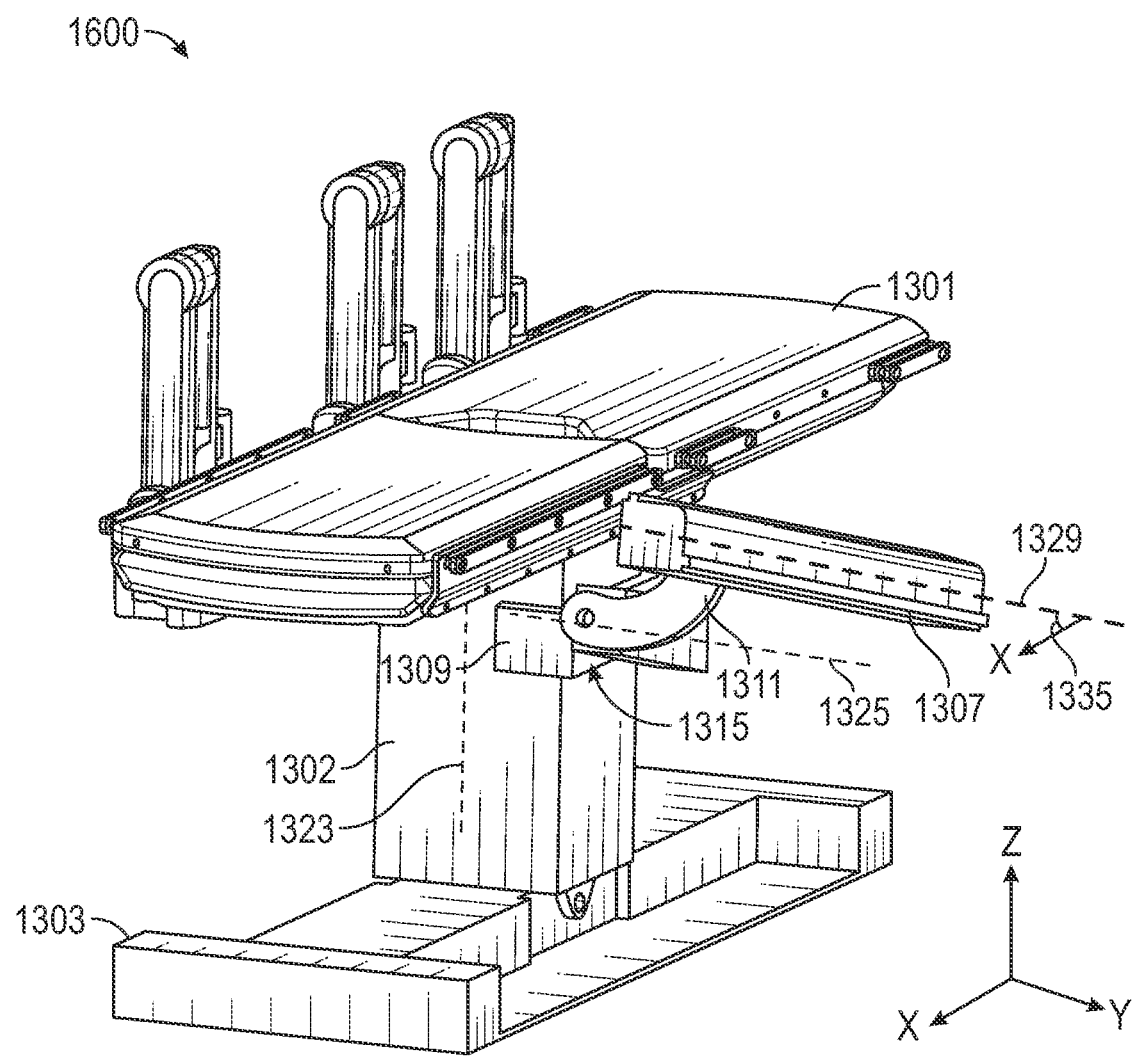
FIG. 16 is an isometric view of a surgical robotics system with an adjustable arm support configured with a rail capable of tilting according to one embodiment.

FIG. 16 is an isometric view of a surgical robotics system 1600 with an adjustable arm support 1305 configured with a rail 1307 capable of tilting according to one embodiment. As discussed previously, an arm support can include a second joint 1315 configured to allow the arm support 1305 to tilt. In the illustrated embodiment of FIG. 16, the second joint 1315 is positioned between the carriage 1309 and the rail connector 1311, although, as discussed previously, other positions for the second joint 1315 are possible. The second joint 1315 can be rotational joint configured to rotate or provide adjustment of the arm support 1305 about the second axis 1325. As shown in FIG. 16, by rotating or providing adjustment of the arm support 1305 about the second axis 1325, a tilt angle 1335 of the axis 1329 can be adjusted. The tilt angle 1335 can be measured between, for example, the axis 1329 (of the rail 1307) and the x-axis, the support surface plane 1331, or the table surface plane 1333.

In some embodiments, the second joint 1315 permits tilting of the rail relative to the table 1301. In some embodiments, the table 1301 can also pivot or tilt (for example to a Trendelenburg position), and the second joint 1315 can allow the adjustable arm support 1305 to follow the pivoting or tilting of the table 1301. This can allow surgical arms 1402 to remain in position a relative to the patient 10 and/or table 1301 as the table 1301 pivots or tilts. This may be advantageous as a surgeon or clinician may desire to pivot or tilt the table 1301 intraoperatively. In some embodiments, the second joint 1315 pivots or tilts to allow the rail 1307 to remain parallel with the table 1301 as the table tilts. In some embodiments, the rail 1307 need not remain parallel with the table 1301.

Figure 17A:
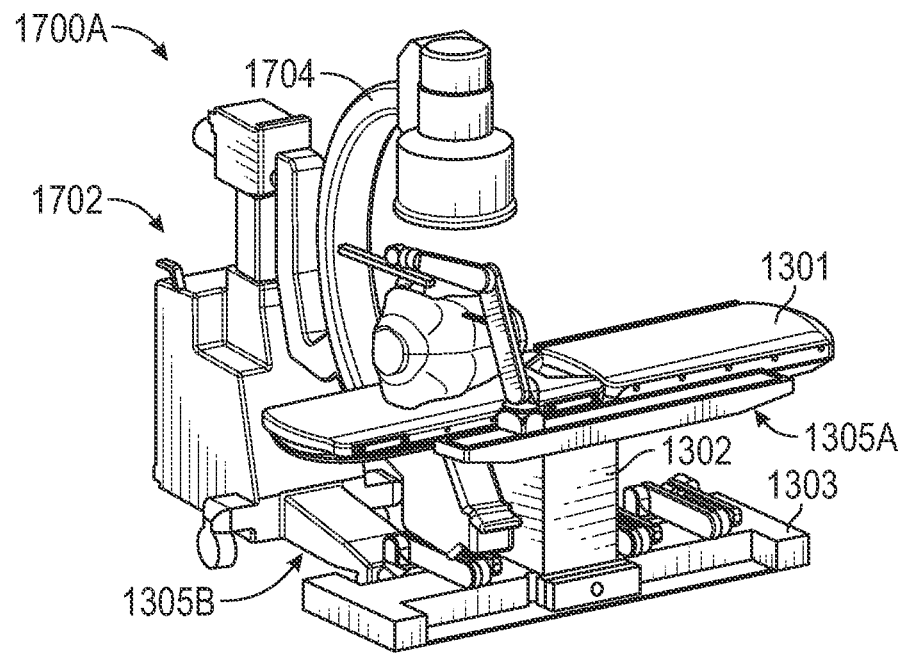
FIG. 17A is an isometric view of a surgical robotics system with adjustable arm supports positioned to allow access for a C-arm of a medical imaging device according to one embodiment.
Figure 17B:
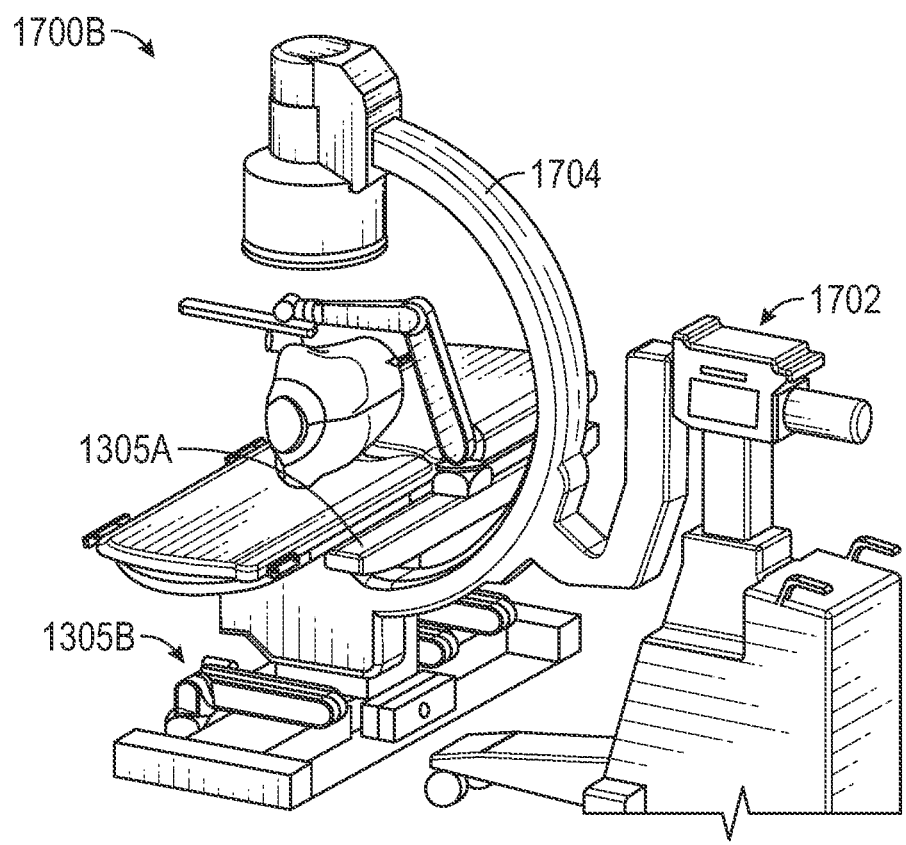
FIG. 17B is an isometric view of the surgical robotics system of FIG. 17A with the adjustable arm supports positioned to allow access for the C-arm of the medical imaging device according to another embodiment.

FIGS. 17A and 17B illustrate that systems including adjustable arm supports 1305 may provide improved access for medical imaging devices. As described above, the position of the adjustable arm support 1305 can be adjusted so as to allow access to or accommodate a medical imaging device, such as a C-arm. In addition to providing improved access for medical imaging devices, the adjustable arm supports also provide improved access for clinicians.

FIG. 17A is an isometric view of a surgical robotics system 1700A with adjustable arm supports 1305A, 1305B positioned to allow access for a C-arm 1704 of a medical imaging device 1702 according to one embodiment. As shown, the second adjustable arm support 1305B is positioned near the floor, so as to be positioned below the C-arm 1704 of the medical imaging device. The first adjustable arm support 1305A is positioned near the table 1301 such that the robotic arm can access the patient.

FIG. 17B is an isometric view of the surgical robotics system 1700B with the adjustable arm supports 1305A, 1305B positioned to allow access for the C-arm 1704 of the medical imaging device 1702 according to another embodiment. In the illustrated embodiment, the first adjustable arm support 1305A is positioned near the table 1301, such that the C-arm 1704 partially surrounds the first adjustable arm support 1305A.

The adjustability of the adjustable arm supports 1305 can advantageously allow the systems to work with will other types of medical imaging devices as well.

Figure 18A:
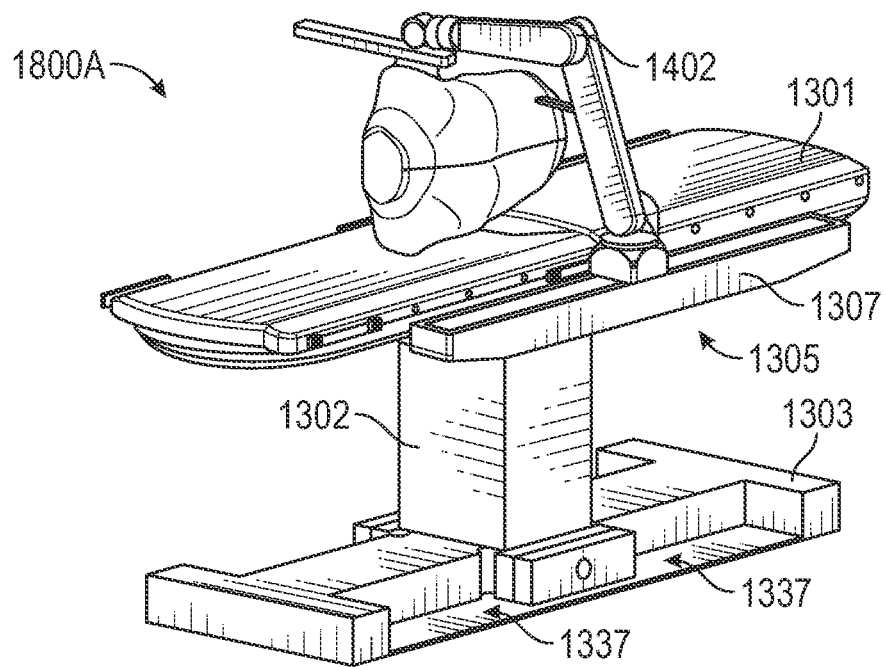
FIG. 18A is an isometric view of a surgical robotics system with adjustable arm supports positioned in a deployed configuration according to one embodiment.
Figure 18B:
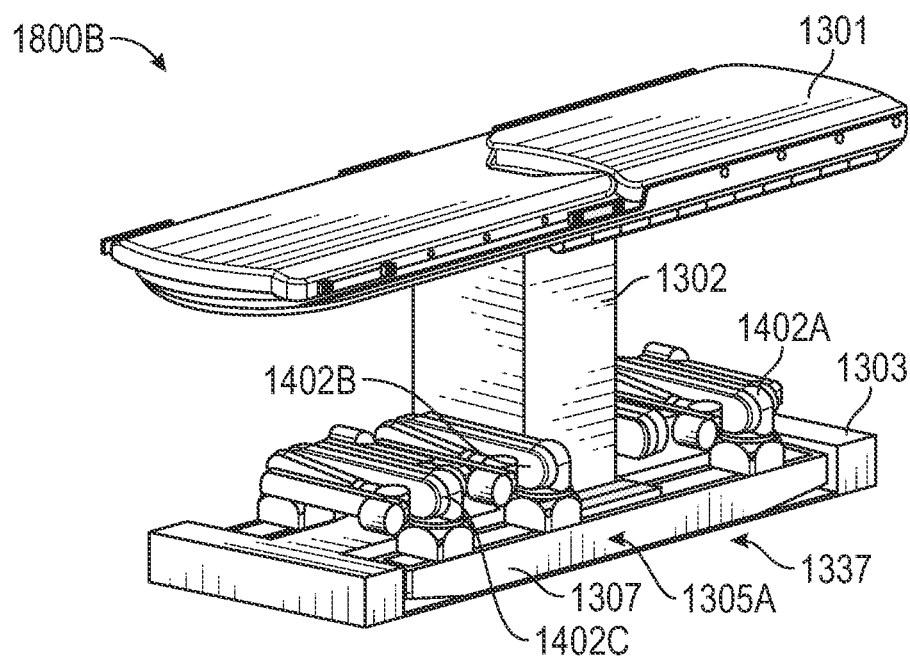
FIG. 18B is an isometric view of a surgical robotics system with adjustable arm supports positioned in a stowed configuration according to one embodiment.

FIGS. 18A and 18B illustrate that systems including adjustable arm supports 1305 can be configured to allow the adjustable arm supports 1305 and corresponding robotic arms 1402 to stow conveniently below the table 1301. This may advantageously provide that the systems are less bulky and cumbersome than some surgical robotics systems. The adjustable arm supports 1305 can transition between a stowed configuration (FIG. 18B) and a deployed configuration (FIG. 18A).

FIG. 18A is an isometric view of a surgical robotics system 1800A with an adjustable arm support 1305 positioned in a deployed configuration according to one embodiment. As shown, the adjustable arm support 1305 has been adjusted such that the rail 1307 is positioned adjacent to a side of the table 1301, and a robotic arm 1402 has been deployed so as to access the patient 10. FIG. 18A also illustrates that the base 1303 can include a recess 1337. The recess 1337 can be configured to receive the arm support 1305 in the stowed configuration, as shown for example, in FIG. 18B.

FIG. 18B is an isometric view of a surgical robotics system 1800B with adjustable arm supports 1305A, 1305B positioned in a stowed configuration according to one embodiment. As shown, bar or rails 1307A, 1307B of each arm support are received into recesses 1337 in the base 1303. In some embodiments, the robotic arms 1402A, 1402B, 1402C can fold over the arm supports 1305A, 1305B as shown. A stowed configuration, for example, with the arm supports 1305A, 1305B stored in recesses 1337 below the table 1301, as shown in FIG. 18B, can advantageously make the system less bulky and cumbersome. In other embodiments, both the arm supports and robotic arms can be stored into recesses in the base 1303. While embodiments described herein illustrate an arm support in a low position relative to the table, in other embodiments, adjustable arm supports can be provided from an elevated or suspended position above the table. These adjustable arm supports in a suspended position can have attributes similar to those that are positioned lower, including independent adjustability, height differential relative to one another, tilt, and longitudinal translation.

In some embodiments, systems including adjustable arm supports 1305 can be configured to be mobile. For example, in some embodiments, the base 1301 can include wheels to allow the system to be easily repositioned (see, e.g., FIG. 14A). For example, the system could have a separate transport cart that lifts it off the floor and moves it. In some embodiments, the system is not permanently affixed in the operating room.

Figure 19:
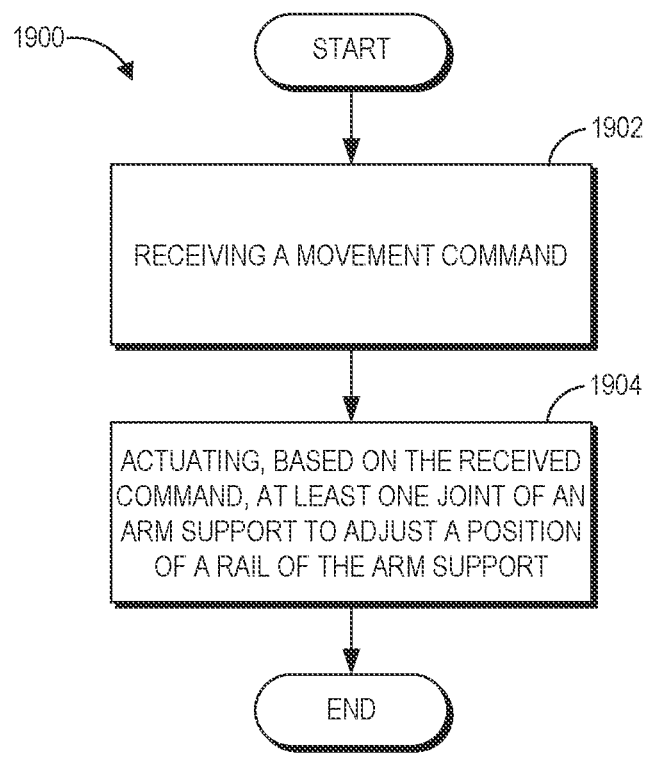
FIG. 19 is a flow chart illustrating a method for operating a surgical robotics system with adjustable arm supports according to one embodiment.

FIG. 19 is a flow chart illustrating a method 1900 for operating a surgical robotics system with adjustable arm supports according to one embodiment. For example, the method 1900 can be used to operate any of the systems described above with reference to FIGS. 13A-18B. In some embodiments, the method 1900 can be stored as computer readable instructions stored in a memory. A processor can access the memory and execute the computer readable instructions to perform the method 1900.

The method 1900 begins at block 1902 which involves receiving a command. In some embodiments, the command is received from a physician, nurse, physician assistant, surgeon staff, etc. The command may relate to the positioning of at least one of a first robotic arm, a medical instrument coupled to an end effector of the robotic first arm, and/or an arm support coupled to a base of the first robotic arm. In some embodiments, the command may be a command to stow or deploy the system.

In some embodiments, a first command actuates the at least one joint to adjust the position of the arm support along a vertical axis of the column, a second command actuates a second joint for pivoting up the arm support, a third command actuates a third joint for tilting the arm support and a fourth command causes longitudinal translation of the arm support.

At block 1904, the method 1900 involves actuating at least one joint of an adjustable arm support to adjust a position of a bar or rail of the arm support based on the received command. For example, the method 1900 may actuate one or more of the first joint, the second joint, the third joint, and/or the fourth joint. This may cause the arm support to move in one or more of its degrees of freedom.

The method 1900 may further include raising the arm support, the first robotic arm, and the second robotic arm from a stowed position below the table; positioning the arm support, the first robotic arm and the second robotic arm adjacent the table; adjusting a position of the arm support relative to the table via at least one of the first command, second command, third command, or fourth command, and adjusting a position of the first robotic arm relative to the second robotic arm along the rail of the support joint in preparation for a surgical procedure. In some embodiments, the arm support is positioned below an upper surface of the table.

In some embodiments, the method 1900 is executed by a controller for executing one or more commands based on a kinematics model, wherein the one or more commands control the positioning of one or more of the first robotic arm, the medical instrument coupled to an end effector of the robotic first arm; and an arm support coupled to a base of the first robotic arm and to a column supporting a patient-support table, wherein the arm support comprises at least one joint and a rail configured to support the first robotic arm.

Figure 20:
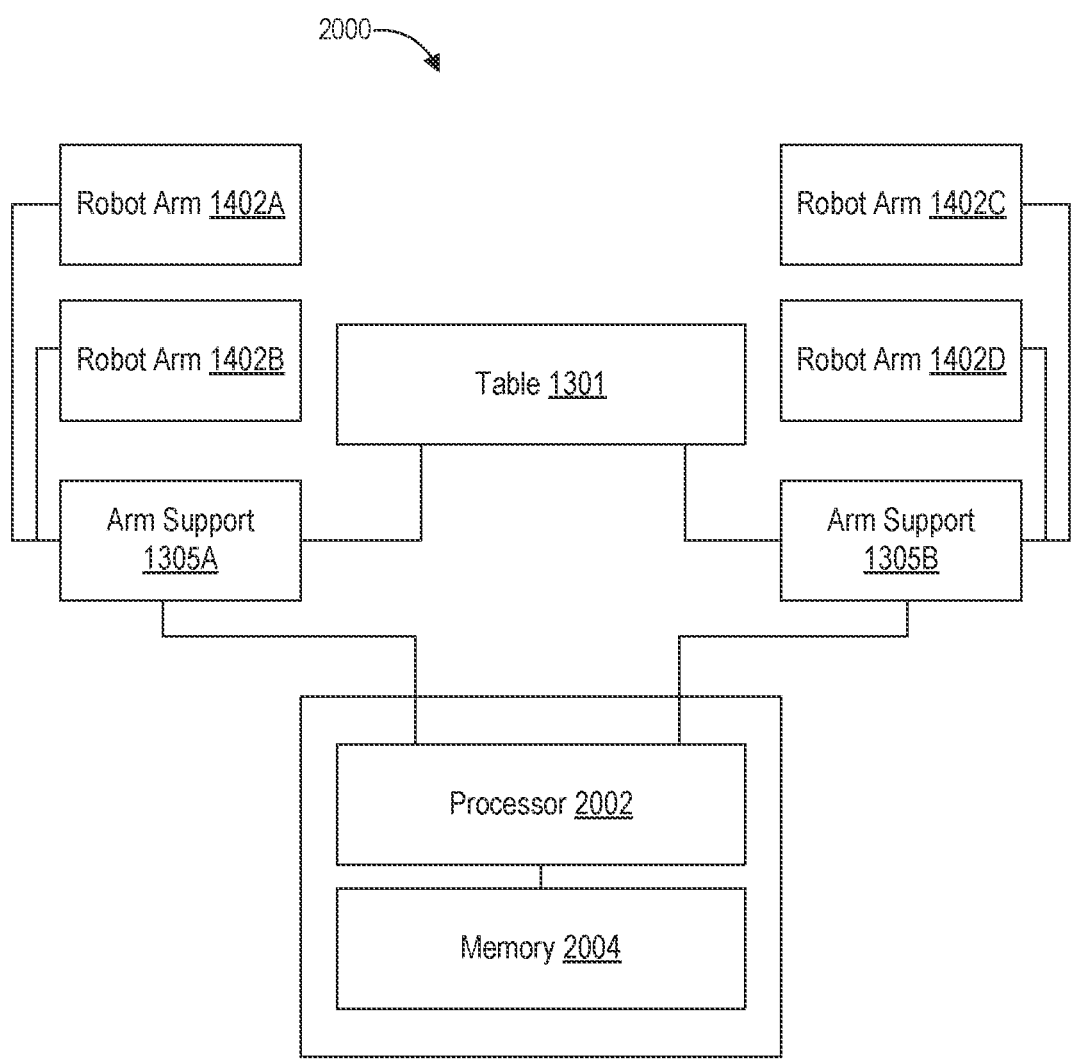
FIG. 20 is a block diagram of a surgical robotics system with adjustable arm supports according to one embodiment.

FIG. 20 is a block diagram of a surgical robotics system 2000 with adjustable arm supports 1305A, 1305B according to one embodiment. As shown, the system 2000 includes a processor 2002 in communication with a memory 2004. The processor 2002 and memory 2004 can be configured to execute, for example, the method 1900 described above.

The system also includes the table 1301. In the illustrated embodiments, two adjustable arm supports 1305A, 1305B are coupled to the table 1301. The adjustable arm supports 1305A, 1305B can be coupled to the table 1301, a column 1302 supporting a table, or a base 1303 supporting the column. Each of the adjustable arm supports 1305A, 1305B is in communication with the processor 2002 such that the process can adjust the position of the adjustable arm supports 1305A, 1305B.

In the illustrated embodiment, a set of robotic arms is attached to each of the adjustable arm supports 1305A, 1305B. For example, robotic arms 1402A, 1402B are coupled to adjustable arm support 1305A, and robotic arms 1402C, 1402D are coupled to adjustable arm support 1305B. In other embodiments, other numbers of robotic arms (e.g., one, three, four, etc.) can be coupled to each arm support 1305A, 1305B. Example robotic arms are described in section XIII below. In some embodiments, as the arm supports support multiple robotic arms, the stiffness of the arm supports can be increased. This increased stiffness provides an added benefit of stability when used with multiple arms, as this can reduce the shaking of the robotic arms during a surgical process.

In some embodiments, the processor 2002 is configured to execute instructions stored in the memory 2004 to adjust a position of the bar or rail along the first axis in response to receiving a command. The command can comprise a command to adjust a position of a robotic medical tool coupled to a robotic arm coupled to the arm support. In some embodiments, the processor 2002 is further configured to execute the instructions to cause the system to at least adjust a position of a rail or the arm supports 1305A, 1305B in response to a physician selected procedure. In some embodiments, the processor 2002 is further configured to execute the instructions to cause the system 2000 to at least adjust a position of the rail to avoid a collision between the robotic arm and at least one of: the table, a patient, an additional robotic arm, and a medical imaging device. The system 2000 may further be configured to avoid collision with other items in the environment of the system, such as, pendants, stirrups, things that clip onto the bed rail, a nurse, etc.). In addition to collision avoidance, the processor 2002 can further be configured to adjust the position of the arm supports 1305A, 1305B to optimize pose or improve manipulability of the robotic arms 1402A, 1402B, 1402C, 1402D.

XIII. Robot Arms Associated with Adjustable Arm Supports

The adjustable arm supports described above can be configured to mount to the table, the column, or the base, and are adjustable (moveable in various degrees of freedom) to support robotic arms positioned on the adjustable arm supports. As the adjustable arm supports can be configured to mount below the surface of the table in accordance with some embodiments, it can be advantageous to employ certain types of robotic arms with the adjustable arm supports. In particular, robot arms that have increased movement and flexibility may be desirable, as the robot arms may have to "work up" from a lower position and avoid collisions (e.g., with the table). This section outlines certain features of robotic arms configured for use with adjustable arm supports.

For example, in some embodiments, robotic arms configured for use with the adjustable arm supports differ from parallelogram remote center robotic arms. In one example, a robotic arm configured for use with the adjustable arm supports can comprise a shoulder with at least two degrees of freedom, an elbow with at least one degree of freedom, and a wrist with at least two degrees of freedom. The kinematics associated with such an arm allow the arm base to be positioned arbitrarily relative to the workspace, allowing for setups that would be challenging for a parallelogram remote center robot mounted alongside a bed.

Further, in some embodiments, a robotic arm configured for use with the adjustable arm supports may include a semi-spherical or spherical wrist configured with at least three degrees of freedom. Such a wrist can allow the robotic arm to roll its wrist joint such that an instrument drive mechanism positioned at the distal end of the robotic arm can be below the arm wrist. This can enable procedures where target workspaces are far above ports.

Some surgical robotic arms include a mechanically constrained remote center with no redundant degrees of freedom (e.g., parallelogram robotic arms). That is, for any remote center position, the distance to the base is mechanically constrained. Robotic arms coming from below the bed, as is the case with robotic arm mounted on the adjustable arm supports described above, can be limited by their mount structures and cannot reach the optimal configurations to make parallelogram robot arms excel. To address this issue, robotic arms configured for use with the adjustable arm supports described above can include one or more redundant degrees of freedom. The redundant degrees of freedom can allow the arms to be jogged within their null space without moving the tool tip, allowing for intraoperative collision avoidance that is not possible previously known surgical robotic arms.

Figure 21:
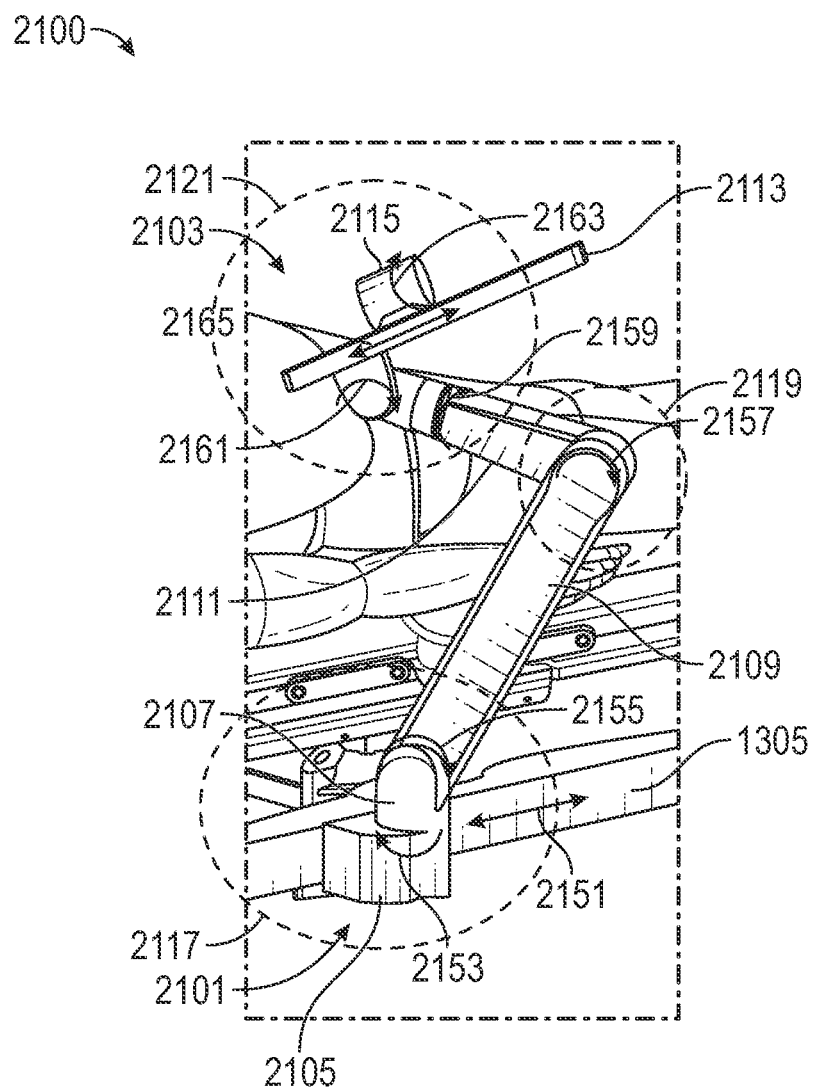
FIG. 21 is an isometric view of a robotic arm according to one embodiment.

FIG. 21 is an isometric view of a robotic arm 2100, according to one embodiment, which may be configured to provide one or more of the features or advantages described above. The robotic arm 2100 can be configured for use with the adjustable arm support(s) 1305 described above. The robotic arm 2100 may comprise a plurality of components arranged serially. The components can be connected by one or more joints (e.g., motorized or hydraulic joints) configured to allow movement or articulation of the robotic arm 2100. As illustrated, for some embodiments, the joints can be grouped into the shoulder 2117, the elbow 2119, and the wrist 2121.

In the illustrated example, the shoulder 2117 includes three joints, the elbow 2119 includes one joint, and the wrist 2121 includes two joints. Stated another way, in some embodiments, one or more of the shoulder 2117, the elbow 2119, or the wrist 2121 can provide more than one degree of freedom for the robotic arm 2100. In the illustrated embodiment, the shoulder 2117 is configured to provide three degrees of freedom, the elbow 2119 is configured to provide one degree of freedom, and the wrist 2121 is configured to provide two degrees of freedom. In other embodiments, the shoulder 2117, the elbow 2119, or the wrist 2121 can be configured with other numbers of joints and/or to provide other numbers of degrees of freedom.

The shoulder 2117 can be located generally at a proximal portion 2101 of the robotic arm 2100. The wrist 2121 can be located generally at a distal portion 2103 of the robotic arm 2100. The elbow 2119 can be located generally between the proximal portion 2101 and the distal portion 2103. In some embodiments, the elbow 2119 is located between a proximal link 2109 and a distal link 2111. In some embodiments, the robotic arm 2100 can include other joints or regions of joints than those illustrated in FIG. 21. For example, the robotic arm 211 could include a second elbow (comprising one or more joints) between the elbow 2119 and the wrist 2121 and/or between the elbow 2110 and the shoulder 2117.

The shoulder 2117, elbow 2119, and wrist 2121 (and/or other joints or components of or associated with the robotic arm) can provide various degrees of freedom. For the illustrated embodiment, the degrees of freedom are illustrated with arrows. The arrows are intended to indicate the motions provided by each degree of freedom. The illustrated embodiment includes the following degrees of freedom. Not all degrees of freedom need be included in all embodiments, and in some embodiments, additional degrees of freedom can be included. The joints providing the various degrees of freedom can be powered joints, such as motorized joints or hydraulically powered joints, for example.

As illustrated, the robotic arm 2100 includes a degree of freedom permitting shoulder translation. The robotic arm 2100 can also include a degree of freedom permitting shoulder yaw. The robotic arm 2100 can also include a degree of freedom permitting shoulder pitch. The robotic arm 2100 can also include a degree of freedom permitting elbow pitch. The robotic arm 2100 can also include a degree of freedom permitting wrist yaw. The robotic arm 2100 can also include a degree of freedom permitting wrist pitch. The robotic arm 2100 can also include a degree of freedom permitting instrument driver roll. This degree of freedom can be configured allow an instrument attached to the instrument driver (or the instrument driver itself) to be rolled around its axis.

An insertion degree of freedom can also be associated with the robotic arm 2100. The insertion degree of freedom can be configured to permit insertion (or retraction) of the instrument (or tool) attached to an instrument driver mechanism 2115 along an axis of the instrument or an axis of the instrument driver 2115.

These and other features of robotic arms configured for use with the adjustable arms supports 1305 described above are described in greater detail in the application entitled "Surgical Robotics System" filed on even date herewith.

XIV. Software

In some embodiments, one or more aspects of a system including adjustable arm supports and corresponding robotic arms can be controlled via software. For example, the system can be designed so that all actuations are robotically controlled by the system, and the system knows the position of all end effectors relative to the tabletop. This may provide a unique advantage that existing robotic surgery systems do not have. Further, this may allow for advantageous workflows including: adjusting the table top intraoperatively (e.g., tilt, Trendelenburg, height, flexure, etc.) while arms and arm positioning platforms move in sync; moving the robotic arms can move away from the operative field for draping or patient loading; after a clinician tells the system the type of procedure, the robotic arms can move to approximate positions near where ports are typically placed (Surgeons could modify and set port selection "presets" for how they like to do surgery); and performing "last mile" docking with cameras on the end effectors and vision targets on cannulas (other non-optical sensors around the end effector could provide similar functionality).

Further, some incarnations of robotic arm joints may require applying high forces to the arm to back-drive the motors and transmissions. This can be reduced with torque sensors in arm joints or a force sensor or joystick at the end effector to allow the robot to know where the clinician is trying to push it and move accordingly (admittance control) to lower back-drive forces felt at the output. Such back-drive regulation can be accomplished in software in some embodiments.

XV. Additional Considerations

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A system, comprising:
a table configured to support a patient;
a column extending along a first axis between a first end and a second end, the first end coupled to the table;

a base coupled to the second end of the column; and a first arm support coupled to at least one of the table, column or the base by at least a first joint configured to allow adjustment along the first axis relative to the table, the first arm support comprising a first bar having a proximal portion and a distal portion extending along a second axis different from the first axis, the first bar configured to support at least one robotic arm, the first bar being capable of translation along a length of the table such that the first bar can extend beyond an end of the table.

2. The system of claim 1, wherein the first axis is a vertical axis and the first joint is configured to allow adjustment of the first bar in a vertical direction.

3. The system of claim 1, wherein the first joint comprises a motorized linear joint configured to move along the first axis.

4. The system of claim 1, further comprising a first robotic arm mounted to the first bar, the first robotic arm configured to translate along the second axis.

5. The system of claim 4, further comprising a second robotic arm mounted to the first bar, the second robotic arm configured to translate along the second axis.

6. The system of claim 5, wherein the second robotic arm is configured to translate along the second axis independently of the first robotic arm.

7. The system of claim 5, further comprising a third robotic arm mounted to the first bar.

8. The system of claim 7, wherein at least one of the first robotic arm, second robotic arm or third robotic arm holds a camera.

9. The system of claim 1, wherein the first arm support comprises a second joint configured to adjust a tilt angle of the first bar.

10. A system, comprising:
a table configured to support a patient;
a column extending along a first axis between a first end and a second end, the first end coupled to the table;
a base coupled to the second end of the column;
a first arm support comprising a first bar having a proximal portion and a distal portion extending along a second axis, the first bar coupled to at least one of the table, column or base by at least a first joint configured to allow adjustment of the first bar along the first axis, the first arm support configured to support at least one robotic arm; and
a second arm support comprising a second bar having a proximal portion and a distal portion extending along a third axis coupled to the column by at least a second joint configured to allow adjustment of the second bar along the first axis, the second arm support configured to support at least another robotic arm,
wherein the first arm support and the second arm support are configured such that a position of the first bar and the second bar along the first axis can be adjusted independently, and wherein the first arm support is configured to be positioned on a first side of the table, and the second arm support is configured to be positioned on a second side of the table.

11. The system of claim 10, wherein the first axis is a vertical axis, the first joint is configured to allow adjustment of the first bar in a vertical direction, the second joint is configured to allow adjustment of the second bar in the vertical direction, and wherein the first bar and the second bar can be adjusted to different heights.

12. The system of claim 10, wherein the second side is opposite the first side.

13. The system of claim 10, wherein:
the first arm support comprises a third joint configured to adjust a tilt angle of the second axis of the first bar relative to a surface of the table; and
the second arm support comprises a fourth joint configured to adjust a tilt angle of the third axis of the second bar relative to the surface of the table.

14. The system of claim 13, wherein the tilt angle of the second axis of the first bar and the tilt angle of the third axis of the second bar can be adjusted independently.

15. The system of claim 10, wherein the first and second arm supports are configured to be stored below the table.

16. The system of claim 10, wherein one or more of the first joint and the second joint, are motorized or controlled by hydraulics.

17. The system of claim 10, wherein the first arm support supports at least two robotic arms that are linearly translatable relative to one another.

18. The system of claim 10, further comprising multiple robotic arms on the first arm support and multiple arms on the second arm support, wherein a number of arms on the first arm support is equal to a number of arms on the second arm support.

19. A system, comprising:
a table configured to support a patient;
a column extending along a first axis between a first end and a second end, the first end coupled to the table;
a base coupled to the second end of the column;
an arm support coupled to at least one of the table, column or the base by at least a first joint configured to allow adjustment along the first axis relative to the table, the arm support comprising a bar having a proximal portion and a distal portion extending along a second axis different from the first axis;
a first robotic arm mounted to the bar, the first robotic arm configured to translate along the second axis;
a second robotic arm mounted to the bar, the second robotic arm configured to translate along the second axis; and
a third robotic arm mounted to the bar.

20. The system of claim 19, wherein at least one of the first robotic arm, second robotic arm or third robotic arm holds a camera.

* * * * *